United States Patent
Howell et al.

(10) Patent No.: US 7,935,080 B2
(45) Date of Patent: May 3, 2011

(54) CATHETER AND INTRODUCER NEEDLE ASSEMBLY WITH NEEDLE SHIELD

(76) Inventors: Glade H. Howell, Sandy, UT (US); Weston F. Harding, Lehi, UT (US); Christopher N. Cindrich, Draper, UT (US); Ralph Sonderegger, Farmington, UT (US); Joseph Frodsham, Kaysville, UT (US)

( * ) Notice: Subject to any disclaimer, the term of this patent is extended or adjusted under 35 U.S.C. 154(b) by 68 days.

(21) Appl. No.: 10/477,438

(22) PCT Filed: Jun. 20, 2003

(86) PCT No.: PCT/US03/19670
§ 371 (c)(1),
(2), (4) Date: Nov. 7, 2003

(87) PCT Pub. No.: WO04/000408
PCT Pub. Date: Dec. 31, 2003

(65) Prior Publication Data
US 2004/0236288 A1    Nov. 25, 2004

Related U.S. Application Data

(63) Continuation-in-part of application No. 10/320,960, filed on Dec. 17, 2002, now Pat. No. 6,652,490, which is a continuation of application No. 09/499,331, filed on Feb. 4, 2000, now abandoned, which is a continuation-in-part of application No. 09/312,335, filed on May 14, 1999, now Pat. No. 6,379,333, which is a continuation-in-part of application No. 09/057,718, filed on Apr. 9, 1998, now Pat. No. 6,004,294, said application No. 10/477,438 is a continuation-in-part of application No. 09/717,148, filed on Nov. 21, 2000, which is a continuation-in-part of application No. 09/590,600, filed on Jun. 9, 2000, now abandoned.

(60) Provisional application No. 60/390,499, filed on Jun. 20, 2002.

(51) Int. Cl.
*A61M 5/00* (2006.01)
*A61M 5/32* (2006.01)
(52) U.S. Cl. .......... 604/110; 604/192; 604/198
(58) Field of Classification Search ............ 604/164.08, 604/110, 192, 198, 263, 164.01
See application file for complete search history.

(56) References Cited

U.S. PATENT DOCUMENTS
4,755,170 A    7/1988  Golden .......... 604/52
(Continued)

FOREIGN PATENT DOCUMENTS
EP    0 750 916 A2    1/1997
(Continued)

*Primary Examiner* — Nicholas D Lucchesi
*Assistant Examiner* — Andrew M Gilbert
(74) *Attorney, Agent, or Firm* — Mark Lindsey

(57) ABSTRACT

A needle shield assembly with a needle having a distal tip and a static feature is provided. The needle shield assembly includes an adapter having an open distal terminus and an open proximal terminus to allow passage of the needle and a needle shield slidably associated with the adapter having an open distal end and an open proximal end where the open proximal end is sufficiently narrow to restrict proximal movement of the needle static feature causing the shield to move in a proximal direction when the needle is pulled proximally after the static feature has established contact with the needle shield proximal end. The assembly includes a canting plate having an unactivated first position and an activated second position that restricts needle movement. The canting plate is activated via a canting plate retention system in communication with the canting plate and responsive to proximal movement of the needle.

15 Claims, 53 Drawing Sheets

U.S. PATENT DOCUMENTS

| | | | |
|---|---|---|---|
| 4,810,248 A | 3/1989 | Masters et al. | 604/192 |
| 4,816,024 A | 3/1989 | Sitar et al. | 604/192 |
| 4,832,696 A | 5/1989 | Luther et al. | 604/164 |
| 4,834,718 A | 5/1989 | McDonald | 604/195 |
| 4,846,811 A | 7/1989 | Vanderhoof | 604/263 |
| 4,917,669 A | 4/1990 | Bonaldo | 604/164 |
| 4,929,241 A | 5/1990 | Kulli | 604/263 |
| 4,944,725 A | 7/1990 | McDonald | 604/164 |
| 4,964,854 A | 10/1990 | Luther | 604/166 |
| 4,978,344 A | 12/1990 | Dombrowski et al. | 604/198 |
| 4,994,041 A | 2/1991 | Dombrowski et al. | 604/164 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,085,648 A | 2/1992 | Purdy et al. | 604/198 |
| 5,135,504 A | 8/1992 | McLees | 604/164 |
| 5,147,327 A | 9/1992 | Johnson | 604/198 |
| 5,176,655 A | 1/1993 | McCormick et al. | 604/198 |
| 5,186,712 A | 2/1993 | Kelso et al. | 604/165 |
| 5,215,525 A | 6/1993 | Sturman | 604/164 |
| 5,215,528 A * | 6/1993 | Purdy et al. | 604/164.08 |
| RE34,416 E | 10/1993 | Lemieux | 604/164 |
| 5,279,591 A | 1/1994 | Simon | 604/263 |
| 5,300,045 A | 4/1994 | Plassche, Jr. | 604/263 |
| 5,312,359 A | 5/1994 | Wallace | 604/164 |
| 5,322,517 A * | 6/1994 | Sircom et al. | 604/198 |
| 5,328,482 A | 7/1994 | Sircom et al. | 604/164 |
| 5,344,408 A * | 9/1994 | Partika | 604/192 |
| 5,395,347 A | 3/1995 | Blecher et al. | 604/198 |
| 5,409,461 A * | 4/1995 | Steinman | 604/110 |
| 5,458,658 A | 10/1995 | Sircom | 604/192 |
| 5,558,651 A | 9/1996 | Crawford et al. | 604/263 |
| 5,562,633 A | 10/1996 | Wozencroft | 604/171 |
| 5,573,510 A | 11/1996 | Isaacson | 604/158 |
| 5,584,809 A | 12/1996 | Gaba | 604/164 |
| 5,599,310 A | 2/1997 | Bogert | 604/164 |
| 5,601,536 A | 2/1997 | Crawford et al. | 604/263 |
| 5,611,781 A | 3/1997 | Sircom et al. | 604/164 |
| 5,613,952 A | 3/1997 | Pressly, Sr. et al. | 604/110 |
| 5,662,610 A | 9/1997 | Sircom | 604/110 |
| 5,676,658 A | 10/1997 | Erskine | 604/263 |
| 5,683,365 A * | 11/1997 | Brown et al. | 604/110 |
| 5,695,474 A | 12/1997 | Daugherty | 604/162 |
| 5,697,907 A | 12/1997 | Gaba | 604/110 |
| 5,704,919 A | 1/1998 | Kraus et al. | 604/192 |
| 5,713,876 A | 2/1998 | Bogert et al. | 604/243 |
| 5,718,688 A * | 2/1998 | Wozencroft | 604/164.07 |
| 5,833,670 A | 11/1998 | Dillon et al. | 604/263 |
| 5,853,393 A | 12/1998 | Bogert | 604/165 |
| 5,865,806 A | 2/1999 | Howell | 604/164 |
| 5,879,337 A | 3/1999 | Kuracina et al. | 604/192 |
| 5,882,337 A * | 3/1999 | Bogert et al. | 604/110 |
| 5,911,705 A | 6/1999 | Howell | 604/110 |
| 5,935,109 A | 8/1999 | Donnan | 604/164 |
| 5,951,515 A | 9/1999 | Osterlind | 604/110 |
| 6,001,080 A | 12/1999 | Kuracina et al. | 604/171 |
| 6,004,294 A * | 12/1999 | Brimhall et al. | 604/164.08 |
| 6,012,213 A | 1/2000 | Chang et al. | 29/447 |
| 6,132,401 A * | 10/2000 | Van Der Meyden et al. | 604/195 |
| 6,280,419 B1 * | 8/2001 | Vojtasek | 604/192 |
| 6,287,278 B1 * | 9/2001 | Woehr et al. | 604/110 |
| 6,379,333 B1 * | 4/2002 | Brimhall et al. | 604/164.11 |
| 6,406,459 B1 * | 6/2002 | Allmon | 604/192 |
| 6,595,955 B2 * | 7/2003 | Ferguson et al. | 604/110 |
| 6,749,588 B1 * | 6/2004 | Howell et al. | 604/164.08 |
| 2004/0049163 A1 * | 3/2004 | Murashita | 604/263 |
| 2004/0186434 A1 * | 9/2004 | Harding et al. | 604/164.08 |

FOREIGN PATENT DOCUMENTS

| | | |
|---|---|---|
| EP | 0750916 A2 | 1/1997 |
| EP | 0 747 083 A3 | 4/1997 |
| EP | 0 747 085 A3 | 4/1997 |
| EP | 0747083 A3 | 4/1997 |
| EP | 0747085 A3 | 4/1997 |
| GB | 2 343 118 A | 5/2000 |
| GB | 2343118 A | 5/2000 |
| WO | 9819725 | 5/1998 |
| WO | WO 98/19725 | 5/1998 |
| WO | 9908742 | 2/1999 |
| WO | WO 99/08742 | 2/1999 |

* cited by examiner

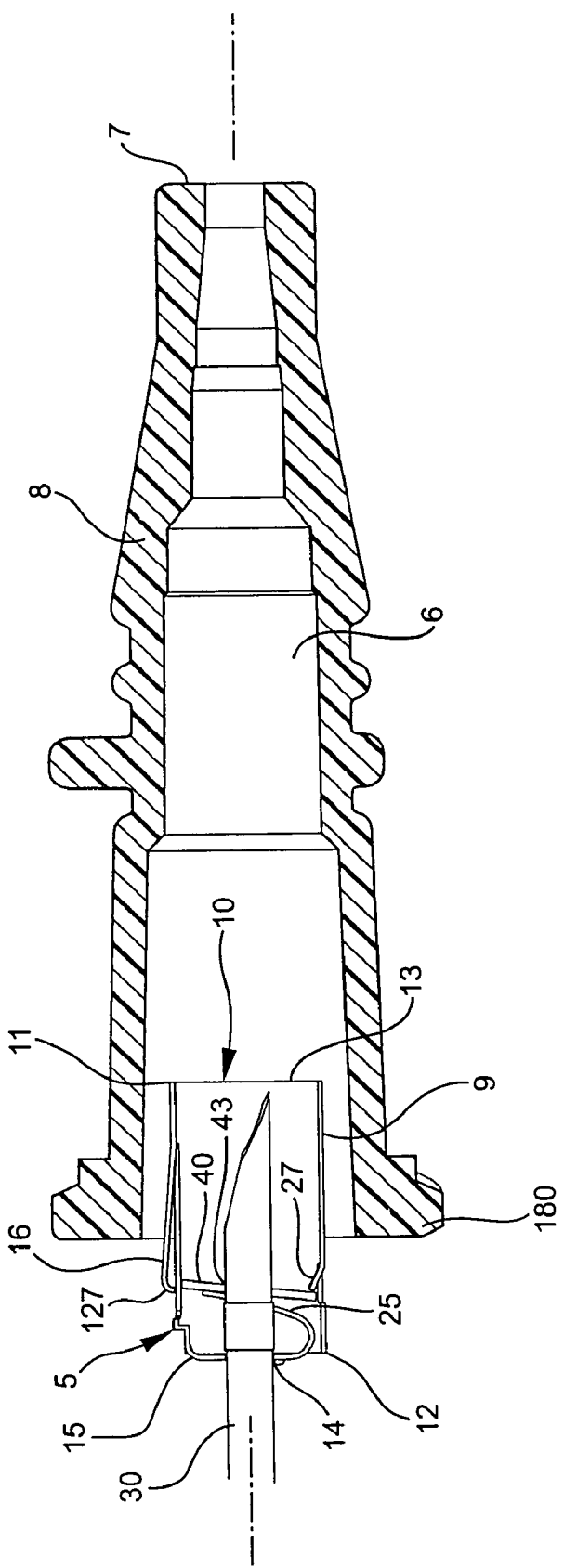

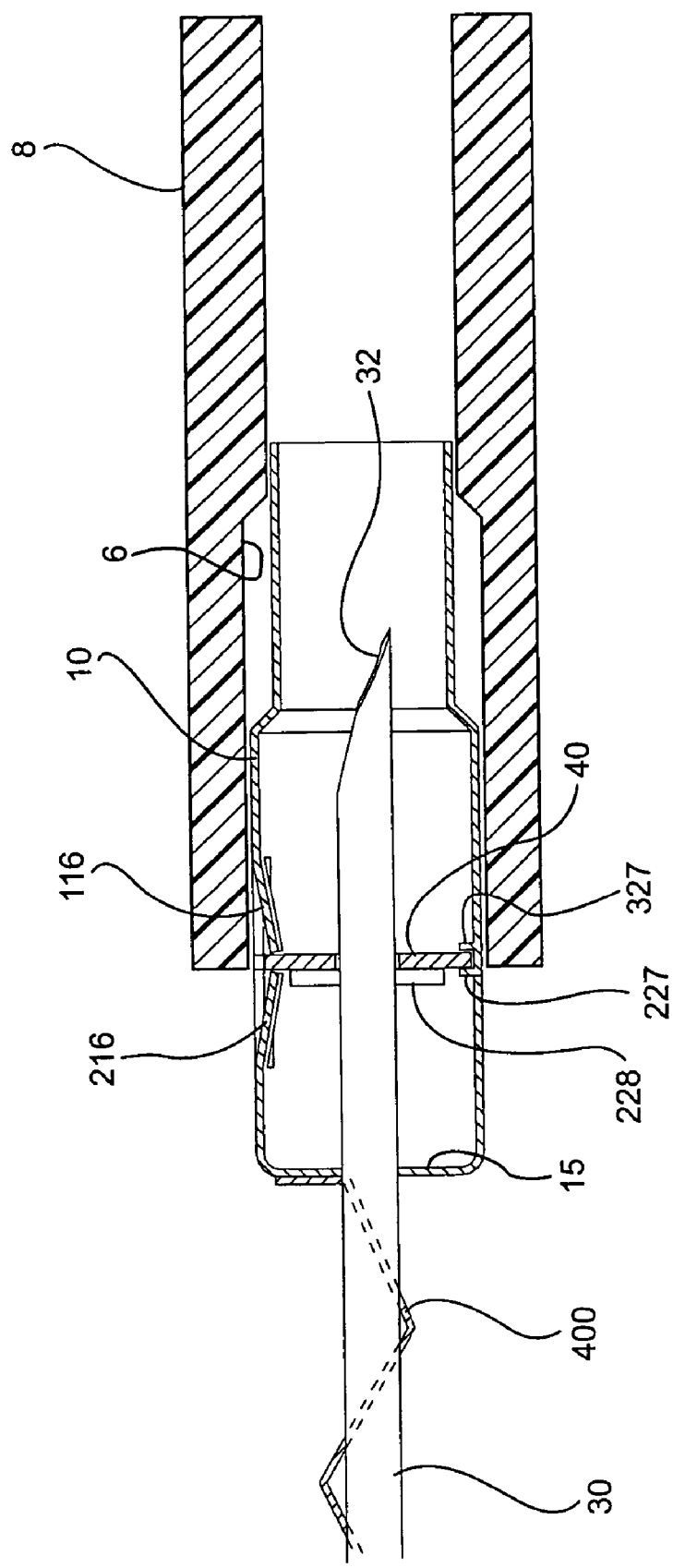

CATHETER AND INTRODUCER NEEDLE ASSEMBLY WITH NEEDLE SHIELD

RELATED APPLICATIONS

This application claims the benefit under 35 U.S.C. 119(e) of U.S. Provisional Application Ser. No. 60/390,499 filed Jun. 20, 2002.

This application is related to the following previously filed applications, each of which is incorporated by reference: This application is a continuation-in-part of Ser. No. 10/320,960, filed Dec. 17, 2002, now U.S. Pat. No. 6,652,490, which is a continuation of Ser. No. 09/499,331, filed Feb. 4, 2000, now abandoned, which is a continuation-in-part of Ser. No. 09/312,335, filed May 14, 1999, now U.S. Pat. No. 6,379,333, which is a continuation-in-part of application Ser. No. 09/057,718, filed Apr. 9, 1998, now U.S. Pat. No. 6,004,294.

This application is also a continuation-in-part of Ser. No. 09/717,148, filed Nov. 21, 2000, which is a continuation-in-part of Ser. No. 09/590,600 filed Jun. 9, 2000, now abandoned which is a continuation-in-part of Ser. No. 09/312,335, filed May 14, 1999, now U.S. Pat. No. 6,379,333, which is a continuation-in-part of application Ser. No. 09/057,718, filed Apr. 9, 1998, now U.S. Pat. No. 6,004,294.

BACKGROUND OF THE INVENTION

1. Field of the Invention

The subject invention relates to a needle shield assembly constructed to safely shield the sharp distal tip of a needle, and restrict distal movement of the needle tip via a tilting or "canting" plate after the tip is shielded.

2. Background of the Invention

Intravenous (IV) catheters are used for infusing fluid, such as normal saline solution, various medicaments and total parenteral nutrition, into a patient or withdrawing blood from a patient. Peripheral IV catheters tend to be relatively short, and are on the order of about one and one-half inches in length. A common type of IV catheter is an over the needle peripheral IV catheter. As its name implies, an over the needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly are inserted at a shallow angle through the patient's skin into a peripheral blood vessel (i.e., a smaller blood vessel that is not connected directly to the heart but is one of the branches of the central blood vessels that is directly connected to the heart). In order to verify proper placement of the assembly in the blood vessel, the clinician confirms that there is flashback of blood in the needle and in a flashback chamber located at the proximal end of the needle. Typically, the flashback chamber is formed as part of the needle hub. Once proper placement is confirmed, the clinician applies pressure to the blood vessel by pressing down on the patient's skin near the distal tip of the introducer needle and the catheter. This finger pressure occludes further blood flow through the introducer needle. The clinician withdraws the introducer needle, leaving the catheter in place, and attaches a fluid-handling device to the catheter hub. Once the introducer needle is withdrawn from the catheter, it is deemed a "blood contaminated sharp" and must be properly handled.

In recent years, there has been great concern over the contamination of clinicians with a patient's blood and a recognition that "blood contaminated sharps" must be immediately disposed. This concern has arisen, in part, to reduce the risks associated with spreading diseases that can be transmitted by the exchange of body fluids from an infected person to another person. Thus, it is desirable to avoid contact with the body fluid of an infected person. Various needle shields have been developed. Generally, such needle shields work for their intended purpose but could be improved. For example, some needle shields are bulky, difficult to use or require special features or techniques to be operative.

SUMMARY OF THE INVENTION

In accord with one aspect of the invention, an over the needle catheter assembly includes a catheter adapter and a needle. The needle has a diameter and a distal tip, slidingly disposed within the catheter adapter. A needle shield assembly is slidably mounted on the needle. The needle shield assembly has an open distal end and an open proximal end though which the needle passes. A rigid plate, referred to as a "canting plate," is disposed within the needle shield assembly and has an unactivated first position and an activated second position. In the second position, the canting plate restricts needle movement. Means for retaining the canting plate are provided. The canting plate retention means is in communication with the canting plate and responsive to proximal movement of the needle, whereby, when the needle tip is housed within the needle shield assembly, the canting plate retention means is actuated, causing distal movement of the needle to urge the canting plate from the unactivated first position to the activated second position.

In accord with certain implementations of this aspect of the invention, the canting plate retention means comprises a spring, a retention arm, and a retention washer. The spring may be selected from the group consisting of a coil spring, a wave washer, and a leaf spring or the like. The needle shield assembly may have a plurality of canting plates responsive to the canting plate retention means. The canting plate retention means may include a canting plate retention arm and a retention washer attached to the canting plate and having a built-in spring. The retention washer may be housed entirely within the shield. The canting plate retention means may include an elastomeric washer and an alignment arm. The elastomeric washer may have a truncated distal end. The catheter adapter and the shield may be held together by an interlock. A static feature may be provided on the needle, wherein said interlock is released prior to or substantially simultaneous with the static feature on the needle contacting the shield proximal end. The length between the needle tip and the static feature is such that when said static feature contacts the shield proximal end, the needle tip is housed within the shield. The canting plate may contain a hole for passage of the needle and be located distally of the proximal end of the shield. The canting plate may be returned to an unactivated position when the needle is no longer urged in a distal direction.

In accord with another aspect of the invention, the over the needle catheter, discussed above, may be used in accord with a method including pulling the needle proximally until the static feature contacts the needle shield's proximal end, confirming that the needle tip is within the shield, and urging the needle distally to cause the canting plate to lock to prevent further distal movement.

In accord with one aspect of the invention, an apparatus is provided for shielding a needle including a housing. A needle shield assembly is movable from an unlocked position within the housing and a locked position outside the housing. The needle shield assembly includes a shield body having a sidewall, a proximal end and a distal end. A canting member is disposed within the shield body for movement from an aligned condition to an off-alignment condition. A spring is operably engaged to the shield body and the canting member, urging the canting member to the off-alignment condition. A retention arm is engaged to the shield body and is displaceable from an engaged position to a disengaged position. When the needle shield assembly is within the housing, the housing displaces the retention arm to the engaged position in which the retention arm engages the canting member and maintains the canting member in the aligned condition. When the needle shield is outside the housing, the retention arm moves to the disengaged position in which the retention arm disengages the canting member, and the canting member is displaced to the off-alignment condition by the spring.

Certain implementations of this aspect of the invention provide the canting member is a canting plate. The spring may be a leaf spring integrally formed with the canting member. The shield body, canting plate and spring may be integrally formed. The shield body may include a retention washer disposed at the proximal end of the shield body, and the retention washer defines an opening through which the needle passes.

The apparatus discussed above may be used with a needle including a feature having a diameter greater than the body of the needle. The opening in the retention washer is sized to permit the needle body to pass but to prevent the feature from passing therethrough. The shield body may include a retention arm that, when the needle shield assembly is within the housing, is biased radially inward to engage the canting member and, when the needle shield assembly is outside the housing, moves radially outward to disengage the canting member. The shield body may include a ledge, disposed opposite the retention arm, and abutting the canting member. The ledge may be integrally formed with the sidewall.

In accord with another aspect of the invention, a needle shield assembly includes a shield body having a sidewall, a proximal end and a distal end. A member, such as an elastomeric washer, is disposed within the shield body and has a central cavity. The cavity is sized to frictionally engage the needle. A canting member is disposed within the shield body and movable between an aligned condition and an off-alignment condition. The member is selectively engaged to the canting member such that, as the needle is moved in a proximal direction with respect to the shield body, the needle displaces the member which, in turn, displaces the canting member to the off-alignment condition.

Certain implementations of this aspect of the invention provide that the member is an elastomeric member and the canting member is a canting plate. Means may be provided for retaining the canting member in the aligned condition. An alignment arm is mounted to the shield body and abuts the canting member. The member is an elastomeric washer abutting the canting member and the proximal end of the shield body. The member is attached permanently and directly to the canting member. A ledge may be fixedly attached to the shield body, disposed distal to the canting member and abutting the canting member. An interlocking flange may be mounted at the distal end of the shield body and an adapter release may be slidably disposed within the shield body. The adapter release includes a release pin that engages the interlocking flange when the canting plate is in the aligned condition and biases the interlocking flange into engagement with a catheter adapter.

In accord with another aspect of the invention, a catheter assembly is provided including a catheter adapter and a needle having a tip. A feature is attached to the needle at a selected distance from the tip. A needle shield assembly is slidably disposed about the needle. The needle shield assembly includes a sidewall, a proximal end and a distal end. An interlocking flange is mounted at the distal end of the shield body and biased radially outward. An adapter release is slidably disposed within the shield body for movement from a distal position to a proximal position. The adapter release includes a release pin that engages the interlocking flange when the adapter release is in the distal position. A canting plate is secured within the housing and includes an opening defined by an edge. The needle is slidably disposed within the opening. The canting plate is movable from an aligned position, in which the needle passes without interference from the edge, to an off alignment position, in which the edge binds the needle. A friction member is moveably disposed within the housing and frictionally engaged to the needle. When the adapter release is in the distal position, it biases the interlocking flange into engagement with the catheter adapter. Conversely, when the adapter release is in the proximal position, the interlocking flange is released from engagement with the catheter adapter. When the needle is displaced proximally with respect to the needle shield assembly, the friction member is displaced, causing the canting plate to move to the off alignment position.

In accord with another aspect of the invention, a needle shield assembly is provided for a needle having a tip and a needle axis. Specifically, a housing has a proximal end and a distal end. A friction member is disposed within the housing and is frictionally engaged to the needle. A canting member is disposed within the housing and includes an edge that defines a member opening. The canting member is displaceable from a first position, in which the member opening is aligned with the needle axis, to a second position, in which the edge lockingly engages the needle. The friction member is operably engaged to the canting member such that movement of the friction member displaces the canting member to the second position.

Certain implementations of this aspect of the invention provide that a retention washer is positioned at the proximal end of the housing and a hole having a selected hole size is disposed in the retention washer.

In accord with another aspect of the invention, a method is provided for shielding a needle. A canting member is in operational engagement with a needle. The canting member is displaceable with respect to the needle, from a first position in which the canting member does not engage the needle, to a second position in which the canting member binds the needle. An actuating member is in frictional engagement with the needle. The needle is displaced with respect to the canting member such that the actuating member is displaced. The canting member is moved to the second position by the actuating member as it is displaced. Certain implementations of this aspect of the invention provide that the friction between the actuating member and the needle causes the actuating member to be displaced with the needle, or that the actuating member acts directly on the canting member.

BRIEF DESCRIPTION OF THE DRAWINGS

The preferred embodiments are illustrated in the drawings in which like reference numerals refer to like elements and in which:

FIG. 2B is a cross-sectional view of the embodiment of the needle shield in FIG. 2A in an actuated condition where the sharp distal tip of the introducer needle has been withdrawn proximally into the needle shield assembly;

FIG. 16B is a cross-sectional view of the embodiment in FIG. 17A where the sharp distal tip of the introducer needle has been withdrawn proximally into the needle shield assembly;

DETAILED DESCRIPTION

As used herein, the term "proximal" refers to a location on the catheter and needle shield assembly of this invention closest to the clinician using the device and farthest from the patient in connection with whom the device is used when the device is used in its normal operation. Conversely, the term "distal" refers to a location on the catheter and needle shield assembly of this invention farthest from the clinician using the device and closest to the patient in connection with whom the device is used when the device is used in its normal operation.

Figure 1:
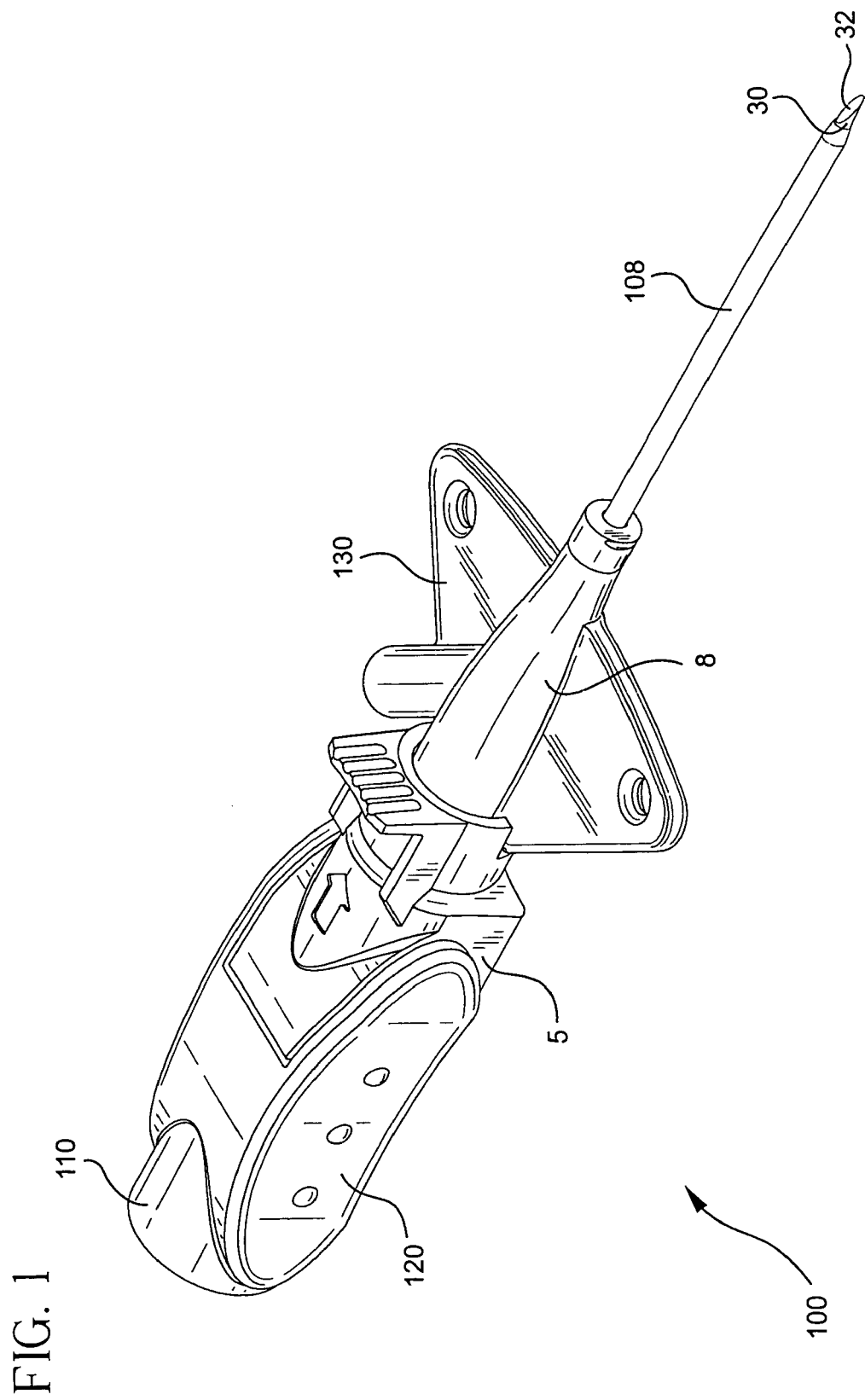
FIG. 1 is a perspective view of an over the needle catheter assembly for use in accord with an aspect of the invention.

A catheter assembly 100 may include a catheter adapter 8 having a catheter 108 attached at its distal end. Wings 130 may be provided on the adapter 8. Before use and during insertion (as depicted in FIG. 1), a needle 30 is disposed within the catheter such that the tip or distal point 32 that extends out of the distal end of the catheter. The proximal end of the needle is attached to a needle hub 110. A finger grip 120 may be incorporated into the needle hub 110. Such a structure, in conjunction with the wings 130, permits the caregiver to employ various technique for catheter insertion, as discussed in U.S. patent application Ser. No. 09/865,915, filed May 25, 2001, incorporated herein by reference.

A needle shield assembly 5 is disposed about the needle, between the needle hub 110 and the catheter adapter 8, as shown in FIG. 1. Alternatively, as shown in, inter alia, FIGS. 2A and 2B, the needle shield assembly 5 may be disposed completely within the catheter adapter and still practice aspects of the invention. It will be appreciated that embodiments of the invention may be implemented with either a needle shield assembly within the catheter adapter, or with a needle shield assembly disposed between the needle hub and the catheter adapter, or at other locations along the needle. Further, implementations of the invention may be employed with needles and sharps used in other devices, such as syringes and blood collection sets.

As discussed more fully below, implementations of the needle shield assembly 5 are designed such that, after insertion of the over the needle catheter 108 into the patient, when the needle 30 is withdrawn, the tip 32 of the needle enters the needle shield assembly. At that point, the needle shield assembly locks onto the needle tip, preventing further displacement of the shield assembly along the needle. As such, the needle shield assembly cannot simply be slipped off the tip of the needle and removed. Additionally, when the needle shield assembly locks onto the needle, it prevents reemergence of the tip from the distal end of the needle shield assembly.

To achieve this locking between the needle shield assembly 5 and the needle 30, the needle shield assembly includes a tilting member or canting plate 40 whose movement is constrained with respect to the needle shield assembly. Preferably, the tilting member is a rigid plate contained within the needle shield assembly. A hole 42 in the canting plate is defined by an edge 43. The needle passes through the hole 42 in the canting plate. In the unlocked condition (seen, e.g., in FIG. 2A), the canting plate is retained in an aligned position with the needle by a retention system or canting plate retention means such that the needle passes through the canting plate without substantial interference. As discussed more fully below, the canting plate retention means may include combinations of fixed structures and movable elements, springs and/or friction members that cooperate to control the position of the canting plate. As the tip 32 of the needle is withdrawn into the needle shield assembly, the canting plate retention means is triggered, causing the canting plate to come "off alignment" or be "actuated." The canting plate is tilted such that it binds against the exterior of the needle, preventing relative movement of the needle to the canting plate. Since the canting plate is also constrained with respect to the needle shield assembly, the needle and its tip are also constrained with respect to the needle shield assembly—thereby locking the needle tip within the needle shield assembly. A feature 35 may be provided on the needle to further prevent the needle shield assembly from slipping off the needle tip. A tether 400 may also be provided to prevent the needle shield assembly from slipping off the needle tip. As discussed below, the feature and the tether can also serve to withdraw the needle shield assembly from the catheter adapter 8 as the needle hub 110 is moved proximally. Once locked in place, the shielded needle may be disposed of.

Retention Washer with Integral Spring

Figure 2A:
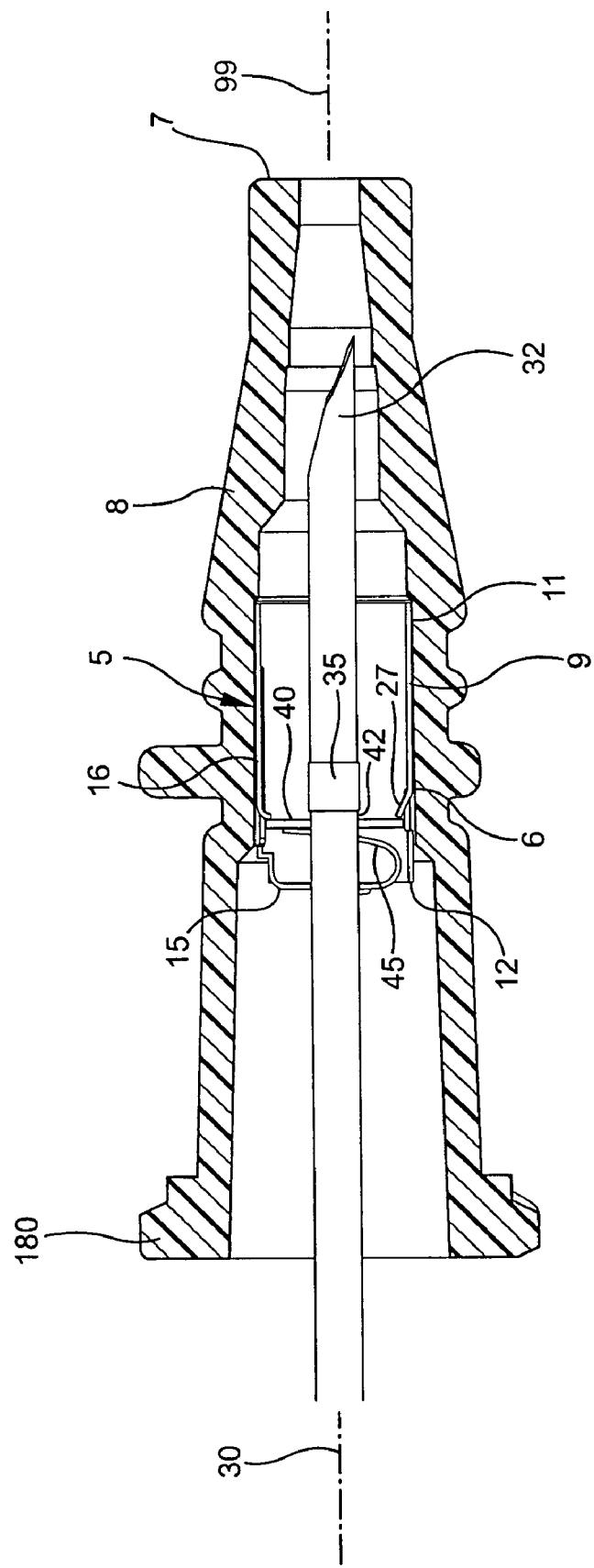
FIG. 2A is a cross-sectional view of one embodiment of the invention shown in an unactuated condition, where the needle has been partly withdrawn through the catheter but the sharp distal tip of the introducer needle has yet to be withdrawn into the needle shield.
Figure 3A:
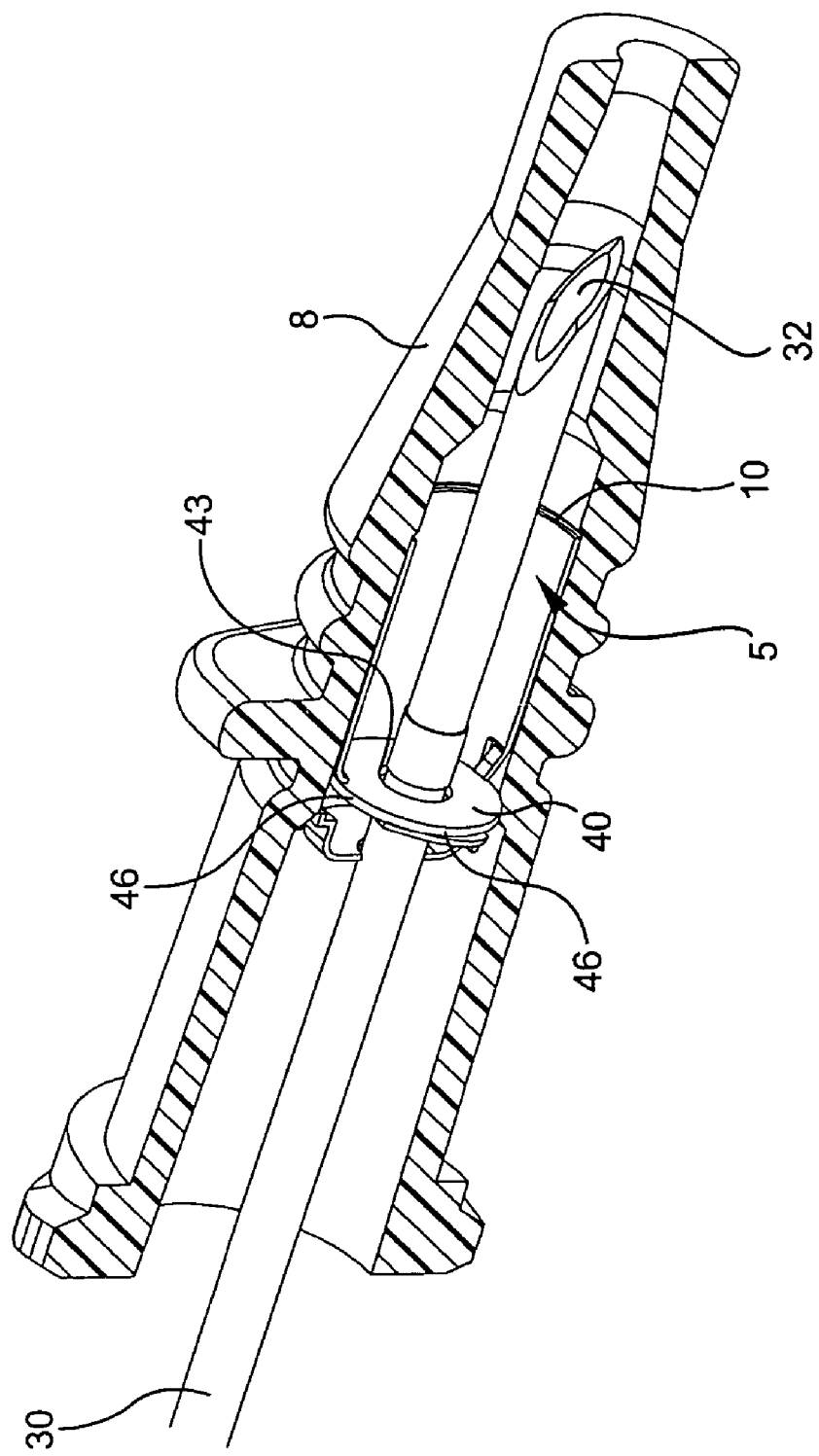
FIG. 3A is a perspective view of the needle shield as depicted in FIG. 2A in partial cross section.
Figure 3B:
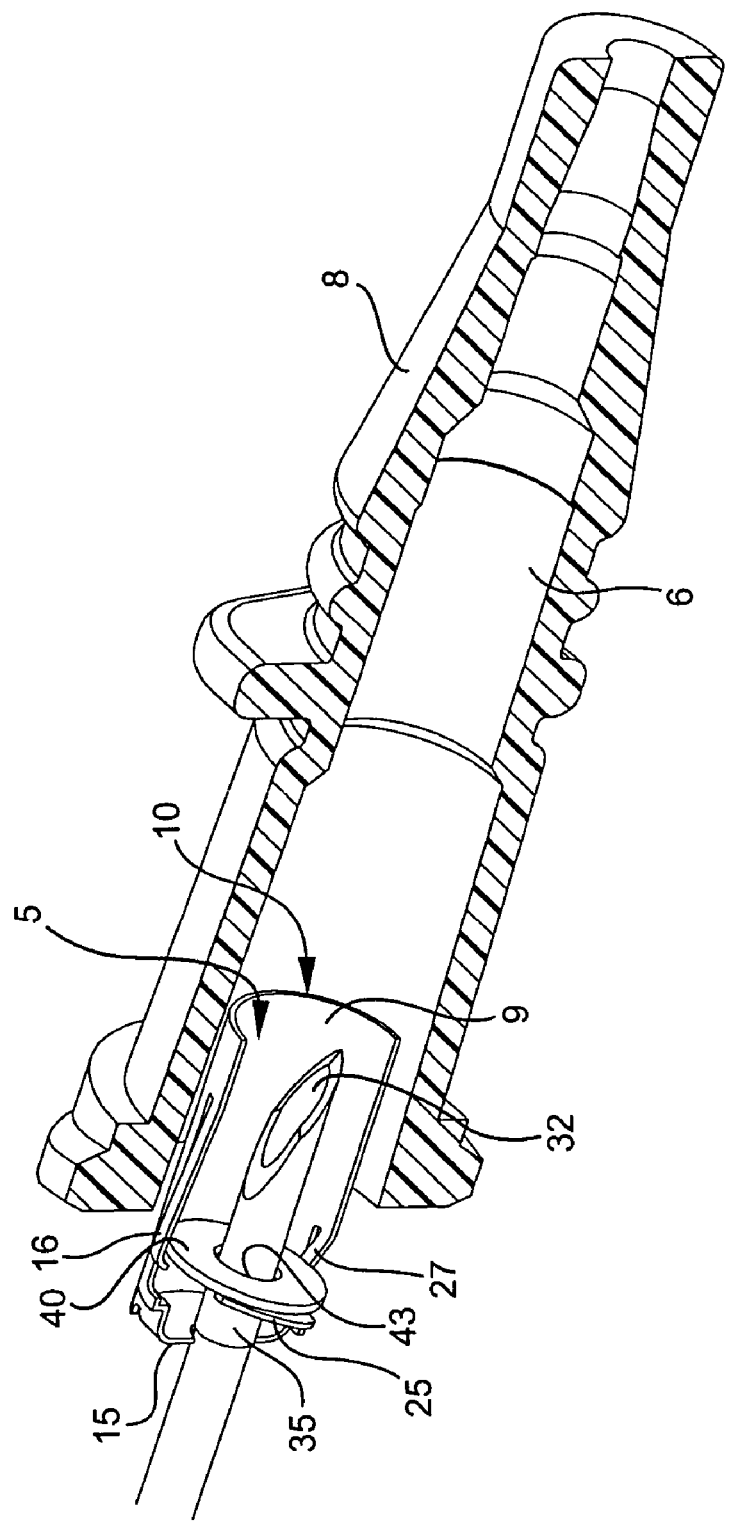
FIG. 3B is a perspective view of the needle shield as depicted in FIG. 2B in partial cross section.

Referring now to FIGS. 2A-3B, one implementation of the invention is shown. FIGS. 2A and 3A depict the needle 30 partially withdrawn into the needle shield assembly 5, but before the needle shield assembly is actuated, or locked, onto the needle. FIGS. 2B and 3B depict the needle shield assembly after actuation, locked onto the needle. In the unlocked or unactuated condition (FIGS. 2A and 3A), the needle shield assembly 5 is positioned within the catheter adapter (or simply "adapter") 8. For the sake of clarity, the catheter 108 has been omitted. It will be appreciated that the catheter is secured to the distal end of the catheter adapter and the needle extends coaxially through the catheter before use, as seen in FIG. 1. The adapter 8 includes an internal chamber forming a shield housing 6 in which the needle shield assembly 5 sits. The shield housing may also be a structure distinct from the adapter. The needle shield assembly has a shield body 10 that includes a sidewall 9 and a distal end 11 and proximal end 12. Typically, the sidewall is cylindrical to fit snugly within the shield housing. The sidewall may have other shapes to achieve a fit within the catheter adapter. The shield ends 11, 12 include a distal opening 13 at the distal end and a proximal opening 14 at the proximal end.

The needle 30 has a distal needle point or tip 32 and an axis 99 and is disposed within the adapter 8, extending through the shield assembly 5 before use. Specifically, the needle passes through the shield openings 13, 14, and extends out of the distal end 7 of adapter 8, through an over-the-needle catheter 108 (not shown in FIGS. 2A-3B for the sake of clarity). The needle diameter is sized to pass through the distal opening 13 and the proximal opening 14 of the shield body 10 without interference.

In accord with certain implementations of the invention, a static feature 35 is also provided on the needle 30 at a selected distance from the tip 32. The static feature 35 is designed such that it is not capable of passage through the proximal opening 14 of shield body 10, such as disclosed in U.S. Pat. Nos. 5,558,651 and 5,215,528, both incorporated herein by reference. The static feature could be an increased diameter portion on the needle 30 (that is, an enlarged dimension, such as formed by a crimp, collar, enlarged diameter sleeve or ferrule), or a roughened surface that locks onto proximal end 12 of the needle shield assembly 5. Other structures can be employed to restrict movement of the needle tip out of the proximal end of the shield (such as a tether, discussed below) and still practice aspects of the invention.

The needle shield assembly 5 contains a shielding mechanism including a canting plate 40 to restrict axial movement of the needle 30 within the shield body 10. The canting plate includes a hole 42 defined by an edge 43 through which the needle passes. The proximal end 12 of the needle shield assembly forms a retention washer 15. The retention washer is attached at one end (the top as seen in FIG. 2A) to the sidewall 9. A spring 45 is attached at the other end of the retention washer. The spring engages canting plate, urging it to an off alignment position (that is, the actuated or locked position), as shown in FIGS. 2B and 3B. As shown, the retention washer and spring are integrally formed. It will be appreciated that these pieces could be separately formed and attached such as by welding or the like.

The needle shield assembly 5 also includes a retention arm 16. Preferably, the retention arm is a leaf spring, integrally formed with the sidewall 9 and including a lip 127 at its proximal end. Of course, other structures could be employed and practice aspects of the invention. The retention arm is biased radially outward from the needle shield assembly, as seen in FIG. 2B. When the needle shield assembly is disposed in the shield housing 6, the shield housing forces the retention arm radially inward, as seen in FIG. 2A. As discussed below, the retention arm helps maintain the canting plate 40 in a needle aligned position (that is, the unactuated or unlocked position) while the needle shield assembly is in the shield housing.

The needle shield assembly 5 includes a ledge 27 formed in the sidewall 9, remote from the retention arm 16. As shown, the ledge is formed by deforming a portion of the sidewall such that it projects radially inwardly. It will be appreciated that the ledge could be formed in other manners (such as by adhering a distinct ledge structure to the inside of the side wall, or by crimping or otherwise creating a bulge in the sidewall). Importantly, the ledge forms a stop that prevents a portion of the canting plate from moving with respect to the needle shield assembly.

The operation of the needle shield assembly 5 of FIGS. 2A-3B will now be discussed. Referring to FIG. 2A, in the aligned or unlocked condition, the canting plate 40 is held in place by a retention system, specifically by the cooperation of the spring 45, the lip 127 of the retention arm 16 and the ledge 27. The spring urges the top of the canting plate in the distal direction (to the right in FIG. 2A). When the needle shield assembly is positioned in the shield housing 6 of the catheter adapter 8, the canting plate is prevented from rotating or displacing by the lip of the retention arm, which engages the top of the canting plate, and the ledge, which engages the bottom of the canting plate. The canting plate thus is maintained in the aligned condition and the needle may pass freely through the hole 42 in the canting plate without substantially engaging the edge 43.

After insertion into a patient's vein, the needle 30 is withdrawn through the catheter 108 and the catheter adapter 8. The feature 35 on the needle engages the proximal end 12 of the needle shield assembly 5. As shown in FIGS. 2B and 3B, the feature 35 on the needle does not fit through the hole 14 in the retention washer 15. Consequently, as the caregiver pulls the needle through the catheter adapter 8, the entire needle shield assembly 5 is pulled out of the shield housing 6. Upon removal of the needle shield assembly, the retention arm 16 succumbs to its natural bias, moving radially outward such that the lip 127 disengages the top of the canting plate 40. Once disengaged, the canting plate is free to rotate under the urging of the spring 45. As the canting plate rotates, edge 43 of the hole 42 binds onto the exterior surface of the needle 30. The canting plate is held in this locked condition by the cooperation of the needle, the ledge 127 and the spring 45. Should the needle be pushed distally in an effort to cause the needle tip to reemerge from the needle shield assembly, the friction on the needle (urging the canting plate distally) and the ledge (preventing movement of the bottom of the canting plate) will cause the canting plate to tilt more severely with respect to the needle, increasing the binding force between the canting plate and the needle, thereby resisting such movement. It will also be appreciated that the feature 35 may be sized so that it does not fit through the hole 42 in the canting plate when the canting plate is off alignment. This will provide further resistance to re-emergence of the needle tip.

As readily seen in FIG. 3A, the canting plate 40 may be a rigid disk with a hole 42 through the middle of it. As shown, the canting plate 40 is substantially circular in shape but could be any of various other shapes including square, rectangular, triangular, oval, symmetrical, asymmetrical, etc. The hole 42 in the center of the canting plate 40 is preferably substantially the same shape as the needle 30 that goes through it. However, other hole shapes could be employed, such as rectangular, triangular or oval shape or any of a variety of other shapes, and still practice aspects of the invention. Further, the canting plate need not be flat. It can be curved or stepped or otherwise shaped for any given application.

The hole 42 in the canting plate 40 is sized to achieve adequate binding force on the needle 30 in view of the geometry of the needle and the geometry of the canting plate. Specifically, the hole should be at least larger than the largest diameter of the feature 35 (when the feature is an enlarged portion of the needle) and, in certain implementations, may increase to be around 100% larger than the diameter of the static feature 35 on the needle 30. In certain other applications, it is preferred that the hole 42 is sized between just larger than the largest diameter of the static feature 35 on the needle 30 to a hole 42 about 10-30% larger than the largest diameter of the static feature 35 on the needle 30. In yet other implementations, it is desirable that the hole be sized, in view of the geometry of the needle shield assembly, such that it engages the needle when the canting plate is tilted between 0° and 45° from perpendicular to the axis 99. It will be appreciated that the canting angle may be selected based on the geometry and materials of the canting plate, the needle shield assembly and the needle and the desired binding force.

When the needle shield assembly 5 is in the unlocked condition (and the canting plate is therefore aligned with the needle), the hole 42 in the canting plate 40 is aligned concentrically to the perimeter circular shape 46 of the body of the canting plate 40. The plate 40 could also be designed to have an eccentric center hole 42 or a hole in any location on the canting plate 40 to achieve desirable binding forces. Further, the hole 42 may be positioned at the exterior or outer edge 46 of the canting plate such that it breaks the outer edge 46. Such a structure will create a "slotted" style of canting plate 40 in accord with certain implementations of the invention. Such may be particularly desirable to permit side loading of the needle into the plate or for use with a guide-wire.

The plate 40 has a thickness suitable for use in providing edges 43 to bind down on the needle surface 31 when the plate 40 is canted or off alignment. This thickness 43, however, may vary depending on other parameters, such as the materials used, the specific geometry of the other parts of the needle shield assembly and the binding force desired.

The canting plate 40 could be entirely housed within the shield body 10 or could be partially within and partially without the shield body 10. A single canting plate 40 or a plurality of canting plates, could be used. In the case of a plurality of canting plates, they could be disposed immediately adjacent to each other, separated by a gap between them, or a combination of both.

Canting Plate and Spring Integral to the Shield

Turning to the implementation of the invention shown in FIGS. 4A-5B, the operation of the structure is similar to that depicted in FIGS. 2A-3B. In this implementation, however, the canting plate or member 40 and the retention washer 15 are integrally formed from the same piece of material as the shield body 10 of the needle shield assembly 5. The canting plate is preferably made of stainless steel, or like material. The material that connects the canting plate 40 to the retention washer 15 serves as the spring 45, urging the canting plate into an off alignment condition. Again, during and after actuation, proximal motion of the needle 30 with respect to the needle shield assembly 5 is halted by the interference between the static feature 35 on the needle 30 and the retention washer 15. After actuation, distal motion of the needle 30 with respect to the needle shield assembly 5 is halted by the engagement of the canting plate 40 to the needle, as discussed above. It will be appreciated that no ledge 27 is required because the spring 45, and its connection with the retention washer 15, restrain the bottom edge of the canting plate from moving with respect to the needle shield assembly. Further, a tether could be employed instead of feature 35 to limit the relative movement of the needle hub and the catheter adapter.

Canting Plate, Spring and Retention Washer Integral to Each Other

Turning to the implementation of the invention shown in FIGS. 6A-7B, the canting plate 40, the spring 45 and the retention washer 15 are integral to each other, but separate from the proximal end 12 of the needle shield assembly 5. The retention washer is attached to the shield body 10 at the proximal end such as by welding, gluing or the like. As depicted, the retention washer is attached on the inner surface of the proximal end of the shield body, but it will be appreciated that the retention washer may be attached at the exterior surface as well. The operation of this implementation is otherwise similar to the prior implementations.

Canting Plate with Friction Member

Referring to FIGS. 8A-C and 9A-C, this implementation of the invention employs a member 28, frictionally engaged to the needle 30, to retain the canting plate 40 in the aligned condition and to move the canting plate to an off-alignment condition when the needle is moved distally with respect to the needle shield assembly 5. Specifically, the needle shield assembly 5 includes a canting plate 40 and a friction member 28, such as an elastomeric washer. Other structures could be employed that frictionally engage the needle and contact the canting plate and still practice aspects of the invention. The elastomeric washer is preferably designed to fit slidably within the shield body 10. The elastomeric washer 28 has a central cavity 29 extending from the proximal end 36 to the distal end 37. The needle 30 passes through the cavity 29 with the washer 28 engaged in a frictional fit on the needle 30. As the needle 30 moves distally and proximally through the elastomeric washer 28, the friction between them causes the elastomeric washer 28 to want to move in concert with the needle 30.

The shield body 10 of the needle shield assembly 5 includes a proximal portion 12 defining a retention washer 15. The shield body has a distal opening 13 and the retention washer has a proximal opening 14. The proximal opening 14 is designed to be just larger than the diameter of the shaft of the needle 30, but not large enough to permit the static feature 35 on the needle 30 to pass through. The retention washer 15 also serves as a backstop for the elastomeric washer 28, securing it within the shield body behind the canting plate 40. As the elastomeric washer 28 is being dragged proximally by the needle 30, it will eventually bottom out on the retention washer 15 and will not be allowed further movement relative to the needle shield assembly see FIG. 8B).

The canting plate 40 is positioned distal of the elastomeric washer 28 and is contained axially by the needle 30. Protruding inwardly from the shield body 10 is an alignment arm 19. The alignment arm 19 defines a positive stop restricting the canting plate 40 from moving in a distal direction at that point. The opposing internal surface of the sidewall 9 of shield body 10 is smooth and offers no resistance to the potential distal motion of the canting plate 40. Hence the alignment arm 19 defines a point at which the canting plate 40 will rotate. As with other implementations of the invention, when the canting plate is rotated far enough it will begin to bind on the needle shaft 30 in a manner similar to that previously described. In this instance, the alignment arm 19 and elastomeric washer 28 therefore serve as the canting plate retention means or retention system.

Figure 8A:
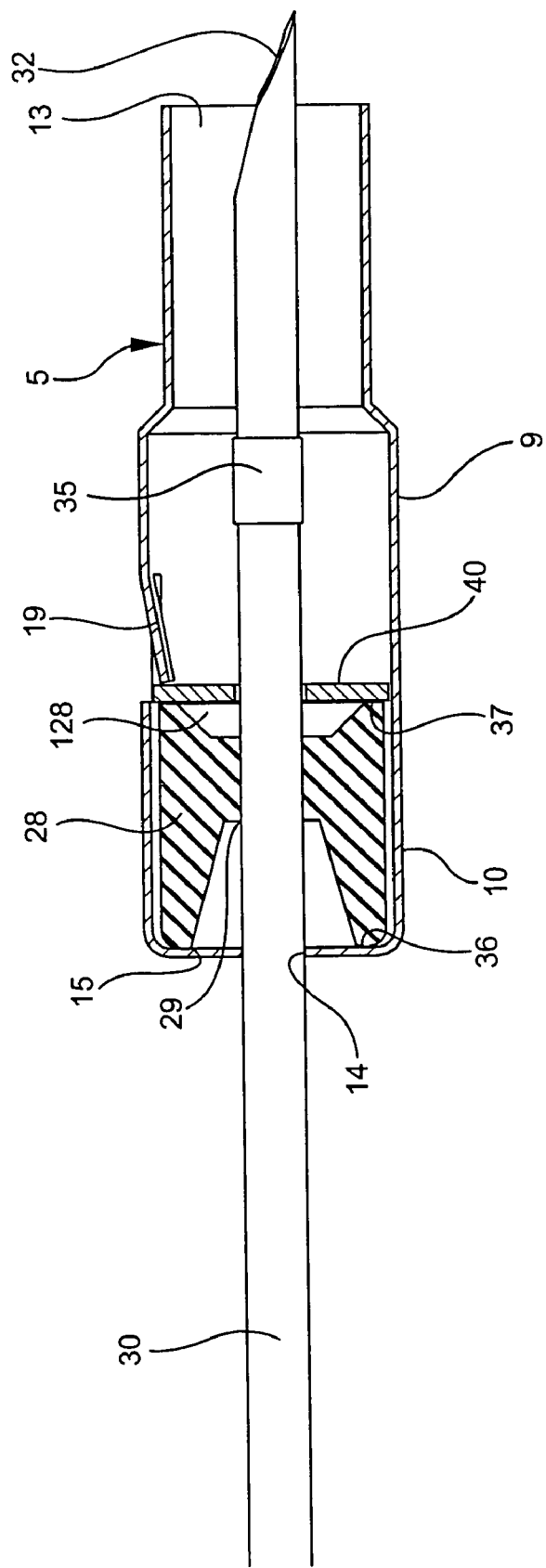
FIG. 8A is a cross-sectional view of another embodiment of the invention in which the canting plate is actuated by friction on the needle, shown in an unactuated condition, where the needle has been partly withdrawn through the catheter but the sharp distal tip of the introducer needle has yet to be withdrawn into the needle shield.
Figure 8B:
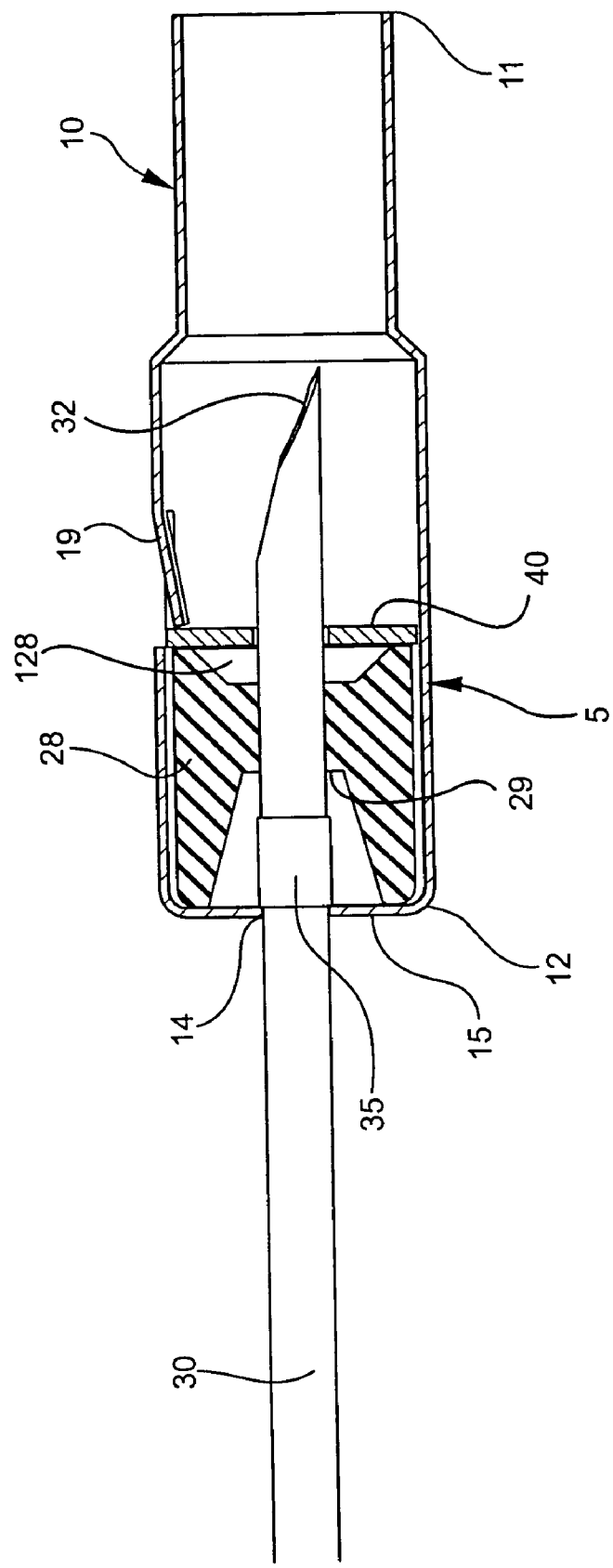
FIG. 8B is a cross-sectional view of the embodiment in FIG. 8A where the sharp distal tip of the introducer needle has been withdrawn proximally into the needle shield assembly.
Figure 8C:
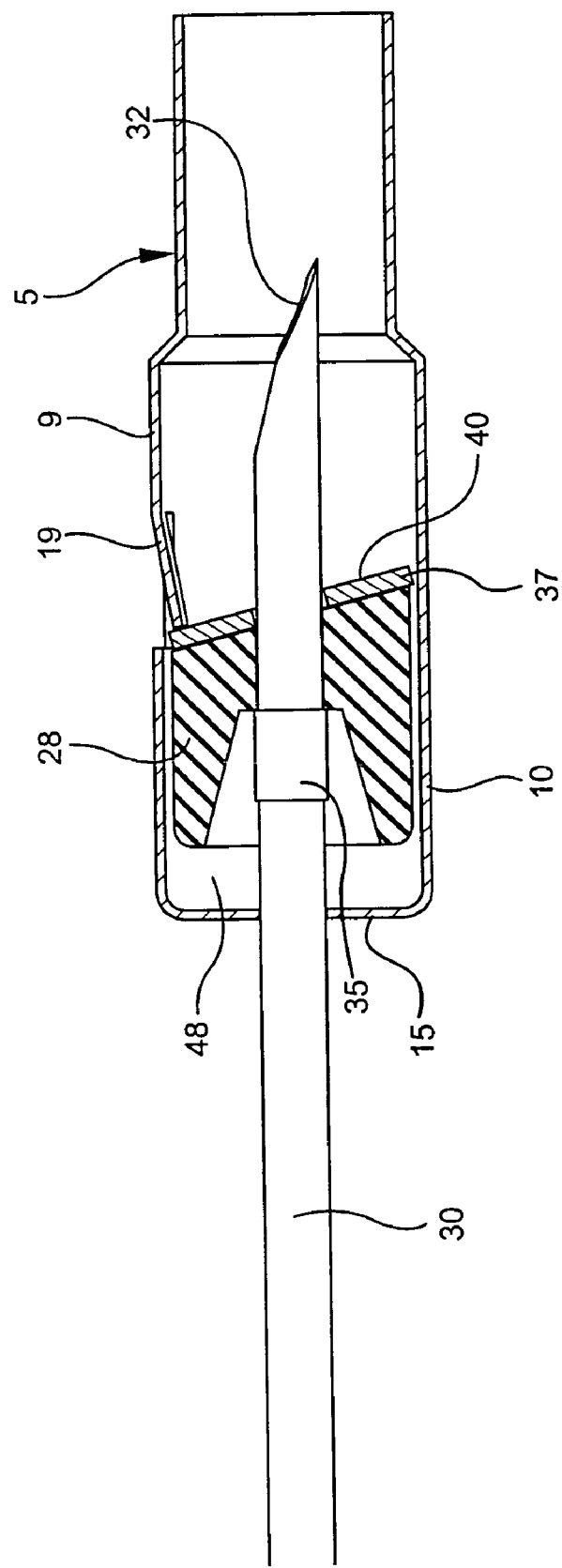
FIG. 8C is a cross-sectional view of the embodiment in FIG. 8A where the sharp distal tip of the introducer needle is being urged distally and the canting plate is tilted to an actuated condition.

The elastomeric washer 28, in cooperation with the alignment arm 19, induces the tilt or actuation of the canting plate 40. Since the elastomeric washer 28 is frictionally fit to the needle shaft 30, when the needle shaft 30 is driven distally with respect to the needle shield assembly 5, the elastomeric washer 28 is dragged with it. As shown in FIG. 8C, the elastomeric washer 28 will bear on the canting plate 40 urging it distally as well. Since the canting plate is restrained only on one side (by retention arm 19), it will tilt and bind on the needle 30. A cavity 128 is formed at the distal end of the washer 128 to deliver force from the washer to the periphery of the canting plate, encouraging the tilting.

The elastomeric washer 28 could be a variety of lengths or shapes and still practice aspects of the invention. As shown in FIGS. 8A-C through 9A-C, the washer has an hourglass shape. The washer could also be a simple flat disc, donut-shaped ring or the like. The particular shape of the washer can be selected by one skilled in the art based on the particular application. While the washer depicted in FIG. 8A is not attached to the canting plate 40, it will be appreciated that the washer could be attached to the canting plate and still function.

The cavity 48 created between the retention washer 15 and the alignment arm 19 can be any length suitable for permitting the elastomeric washer 28 to reside within the shield body 10. The inner diameter of the elastomeric washer 28 (that is, the surface which is in contact with the needle shaft 30) can be smooth or textured. It can also have an array of fins or ribs or any of an assortment of features designed to regulate the friction created against the needle 30. The elastomeric washer 28 can be cylindrical in nature and in contact with the entire surface of the canting plate 40. The washer 28 could be truncated on its distal end 37 and aligned specifically to have its most distal portion in contact against the canting plate 40 in a position directly opposite of the alignment arm 19 to facilitate a more undiluted force against the canting plate 40 during distal motion of the needle 30.

In use, the needle tip 32 of the catheter assembly 100 is inserted into the patient's vein, positioning the catheter in the vein as well. The needle 30 is then withdrawn through the catheter 108. The needle exerts a friction force on the elastomeric washer 28, urging it proximally as the needle is drawn through the needle shield assembly 5. As shown in FIGS. 8A-C, the elastomeric washer abuts the proximal end 12 of the needle shield assembly, stopping the friction member as the needle slides through the central cavity 29. When the feature 35 on the needle contacts the proximal end 12 of the needle shield assembly (for example, the retention washer 15), the feature engages the proximal end, preventing further proximal movement of the needle with respect to the needle shield assembly. As the needle 30 is withdrawn further through the catheter adapter 8, the needle shield assembly 5 is pulled out of the shield housing 6, as shown in FIG. 8B (referred to as "bottoming out").

Figure 9A:
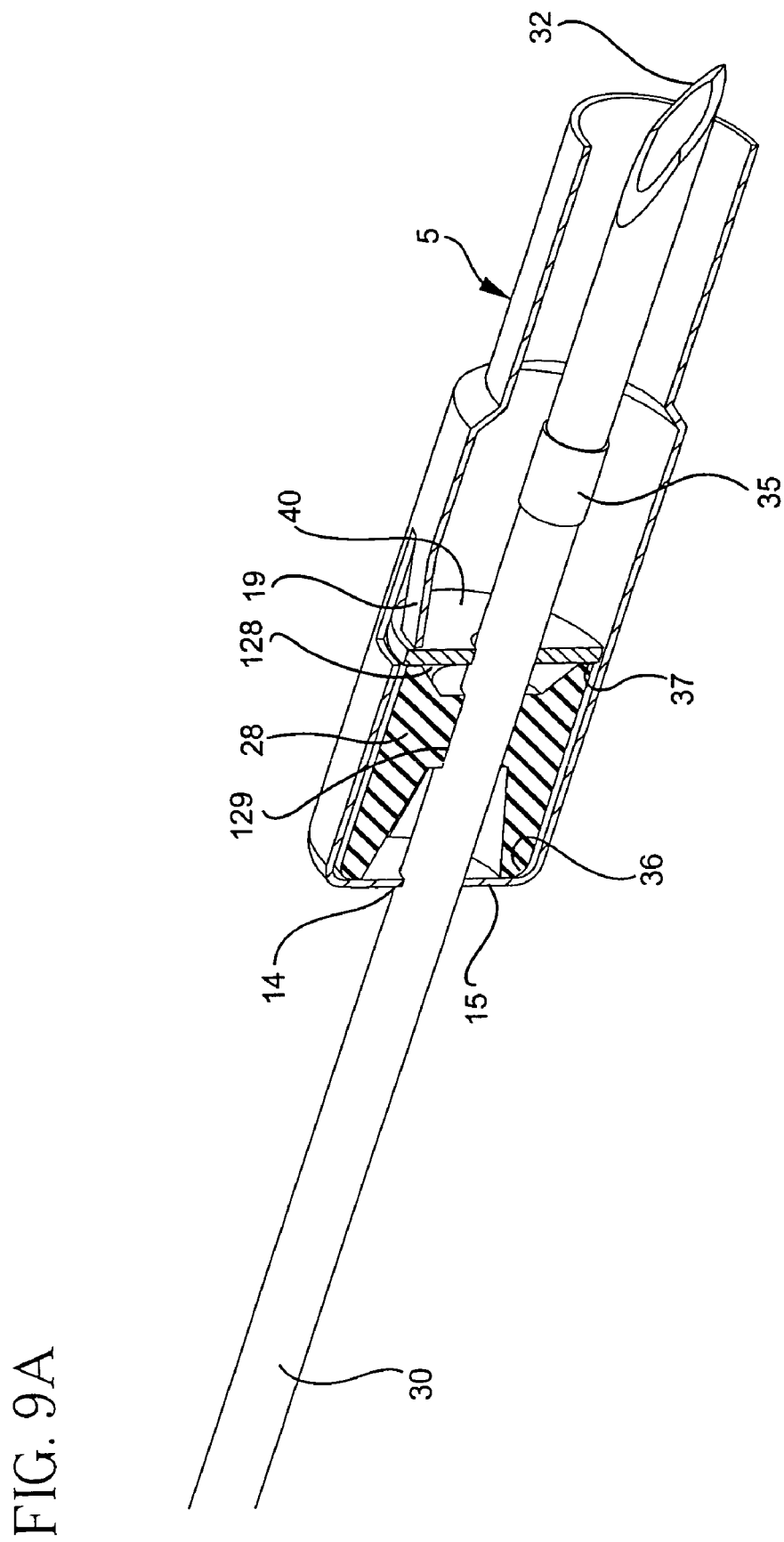
FIG. 9A is a perspective view of the needle shield assembly depicted in FIG. 8A in partial cross section.
Figure 9B:
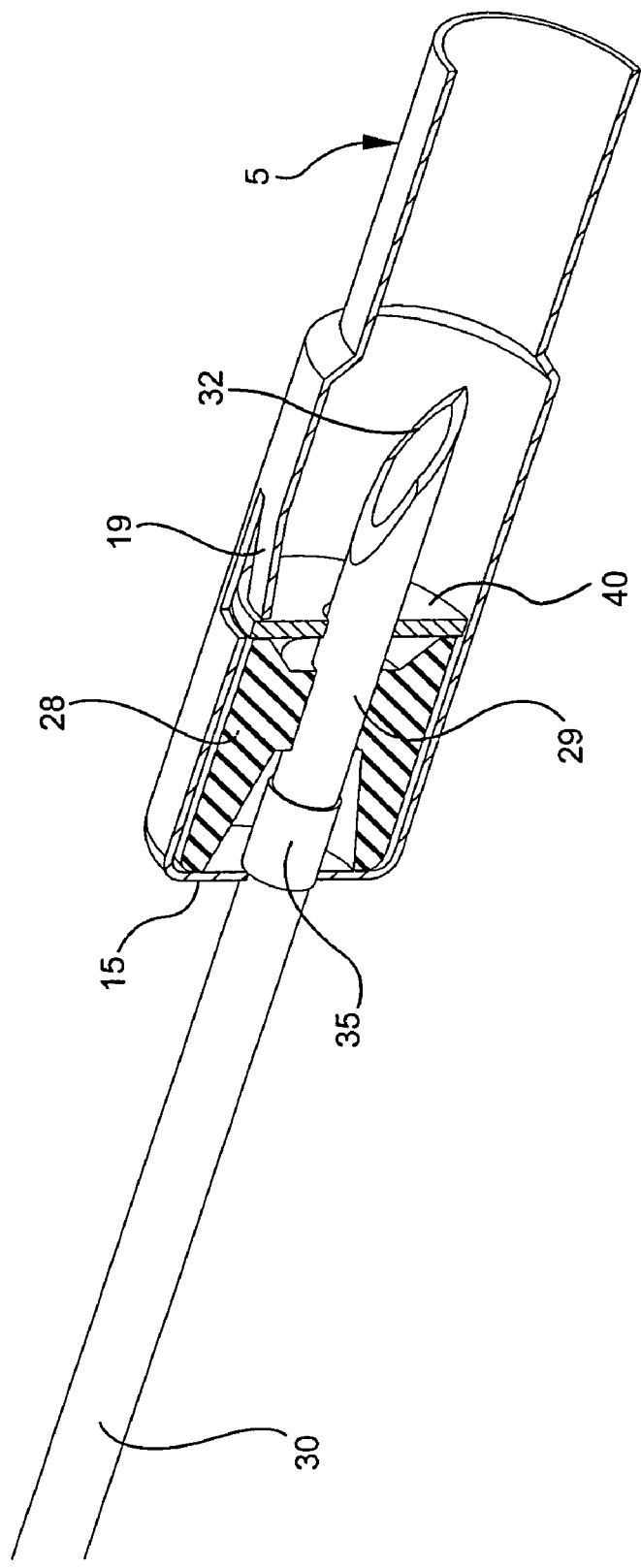
FIG. 9B is a perspective view of the needle shield assembly depicted in FIG. 8B in partial cross section.
Figure 9C:
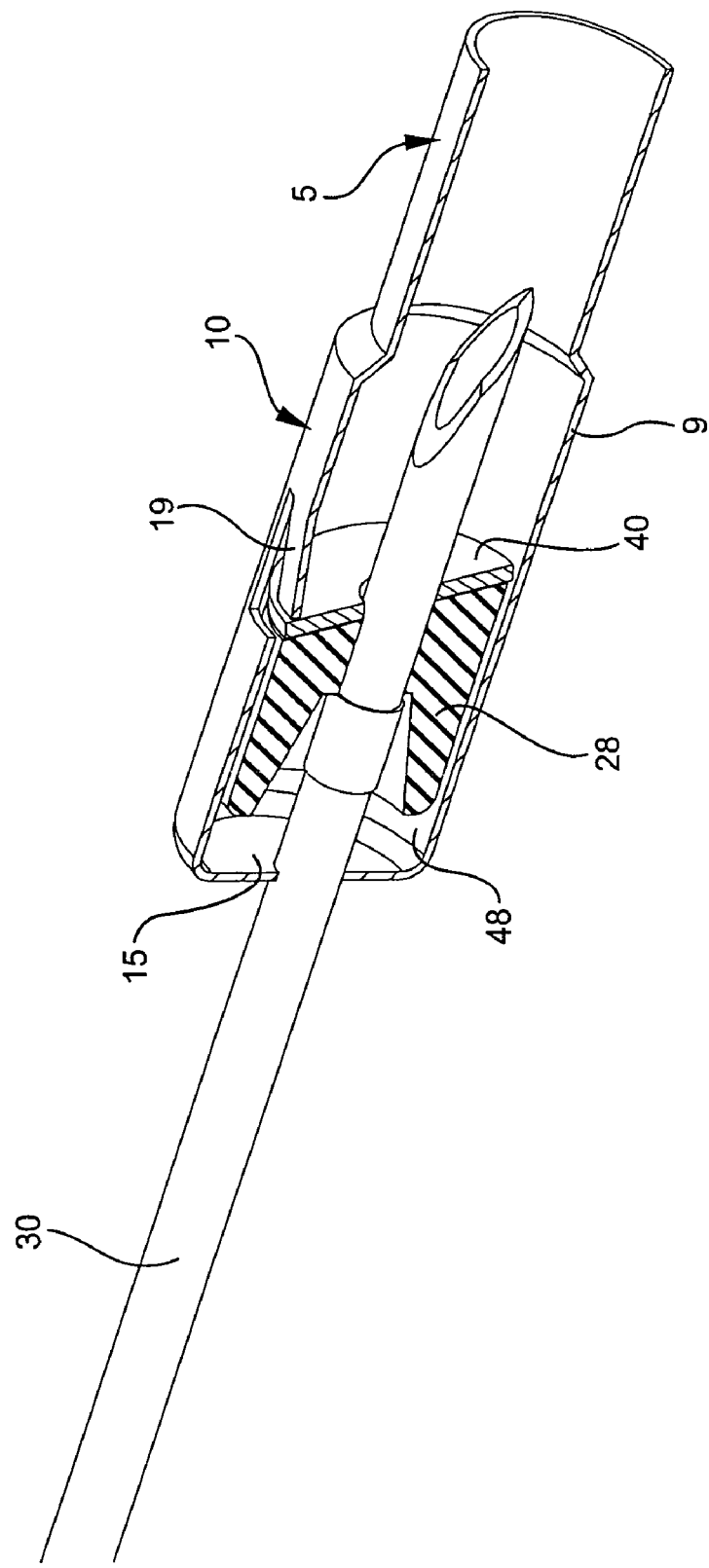
FIG. 9C is a perspective view of the needle shield assembly depicted in FIG. 8C in partial cross section.
Figure 11A:
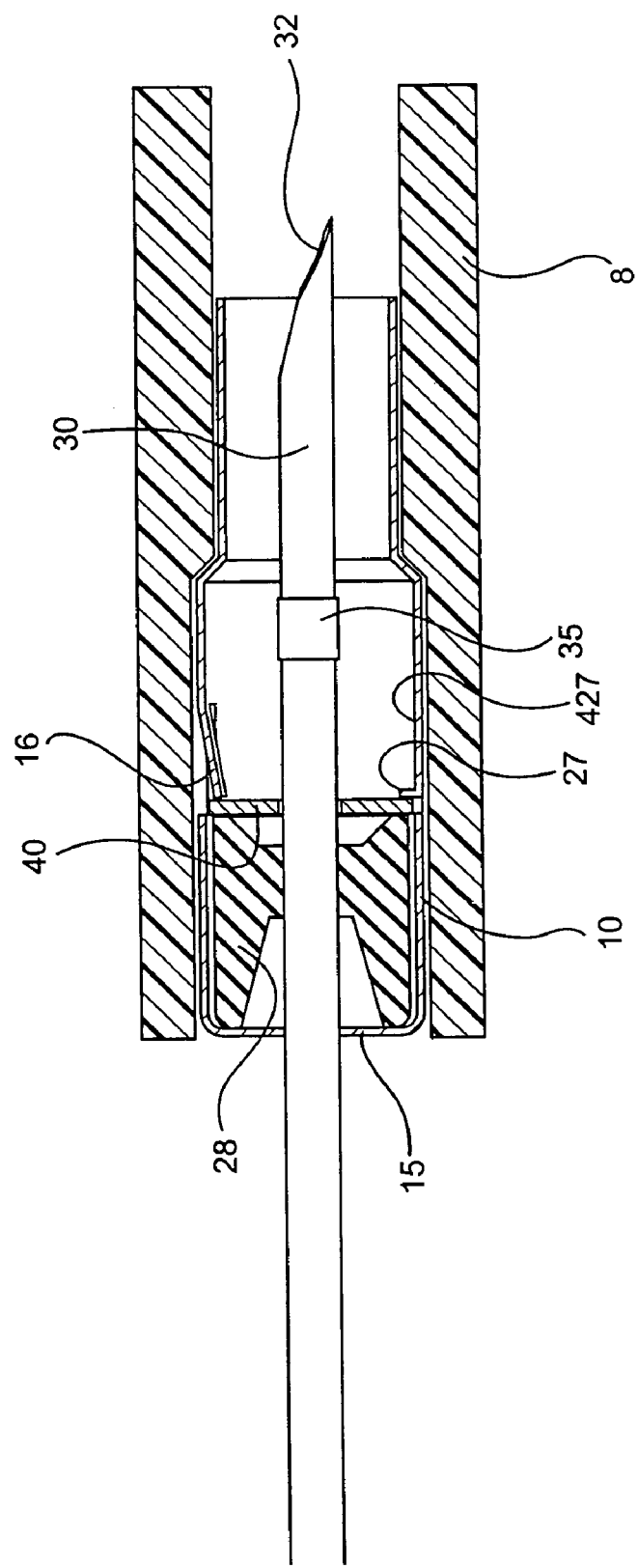
FIG. 11A is a cross-sectional view of another embodiment of the invention in which the canting plate is actuated by friction on the needle, shown in an unactuated condition, where the needle has been partly withdrawn through the catheter but the sharp distal tip of the introducer needle has yet to be withdrawn into the shield.
Figure 11B:
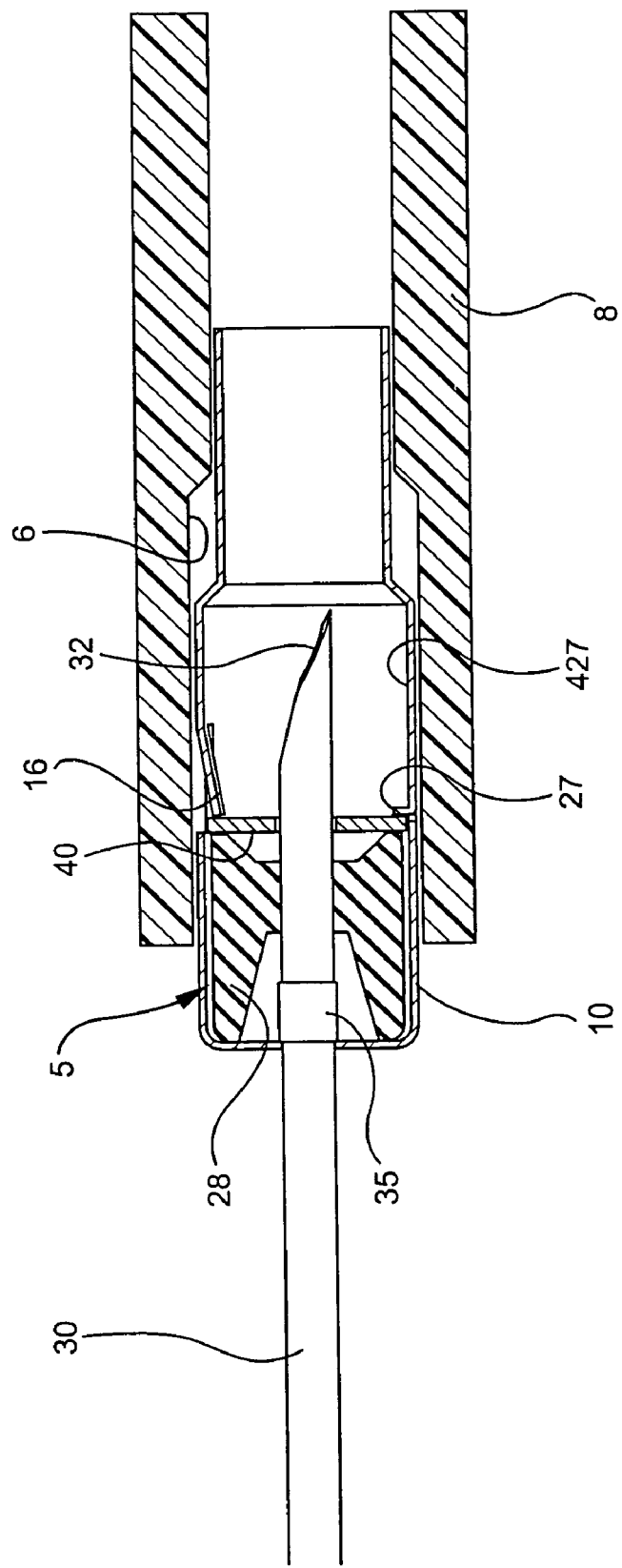
FIG. 11B is a cross-sectional view of the embodiment in FIG. 11A where the sharp distal tip of the introducer needle has been withdrawn proximally into the needle shield.
Figure 11C:
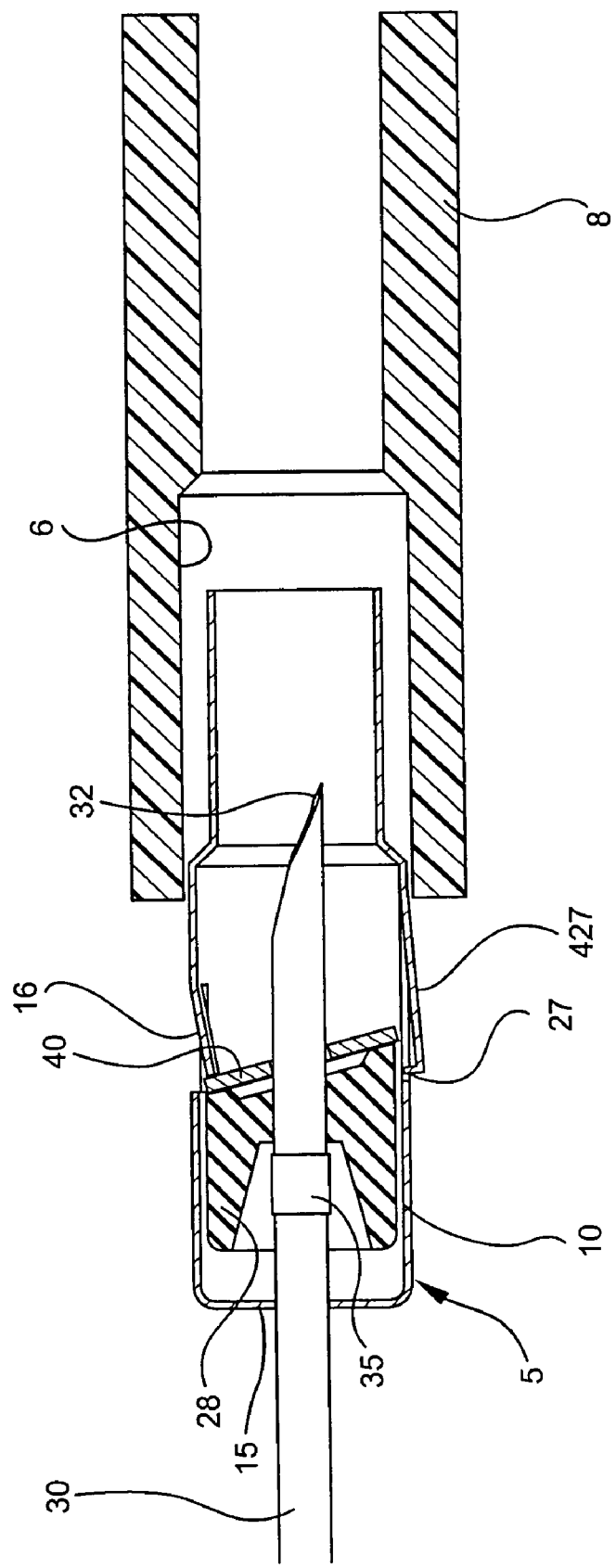
FIG. 11C is a cross-sectional view of the embodiment of FIG. 11A where the sharp distal tip of the introducer needle is being urged distally and the canting plate is tilted to an actuated condition.
Figure 12A:
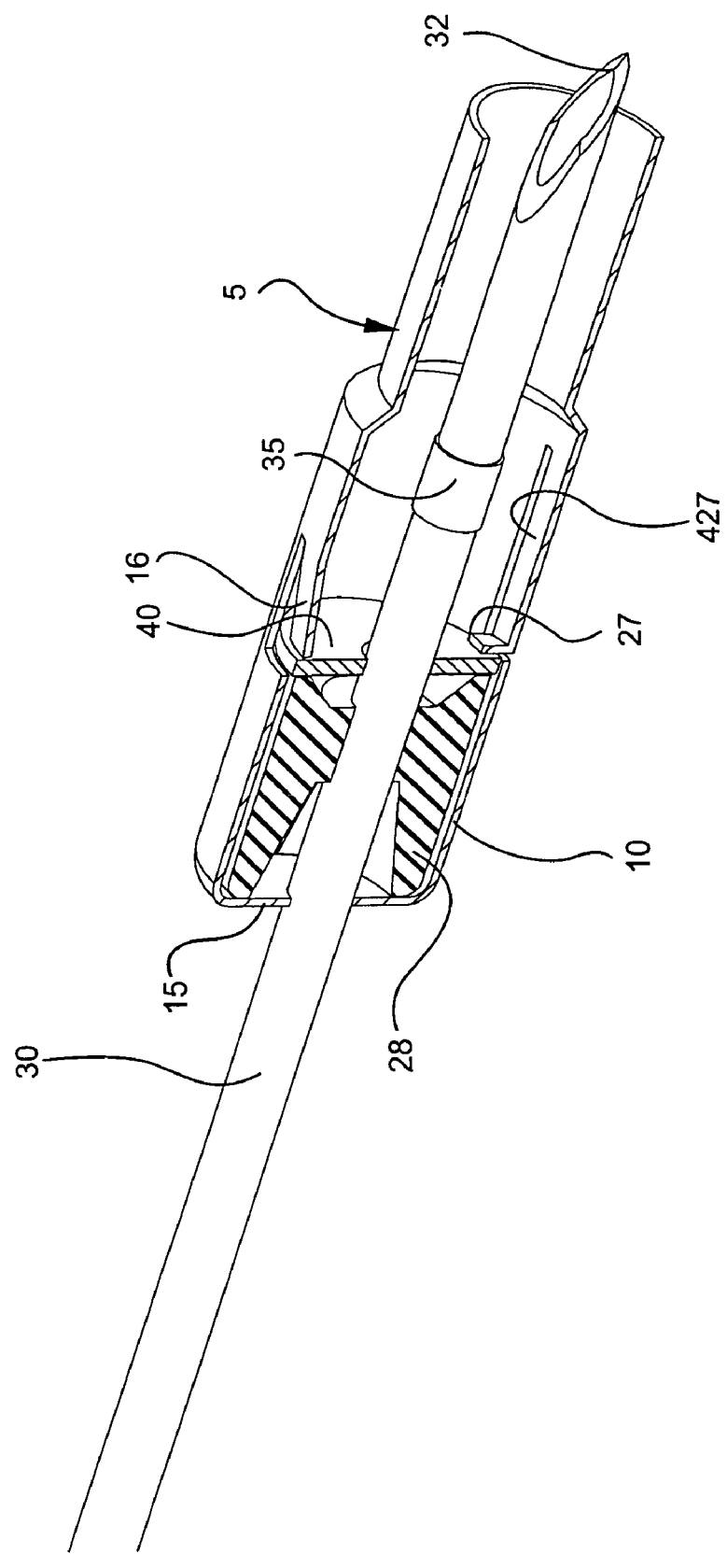
FIG. 12A is a perspective view of a needle shield assembly depicted in FIG. 11A in partial cross-section.
Figure 12B:
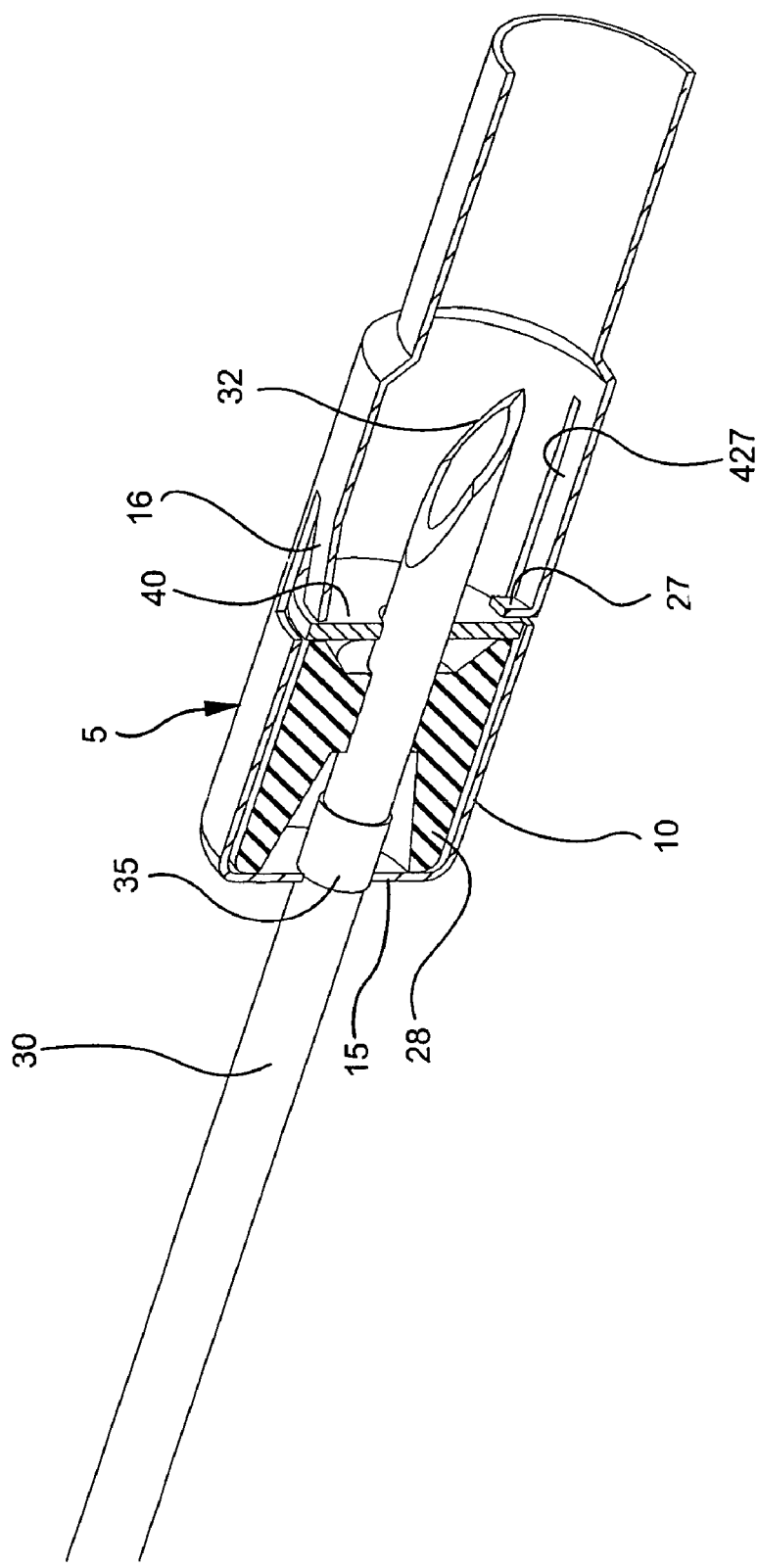
FIG. 12B is a perspective view of the needle shield assembly depicted in FIG. 11B in partial cross-section.
Figure 12C:
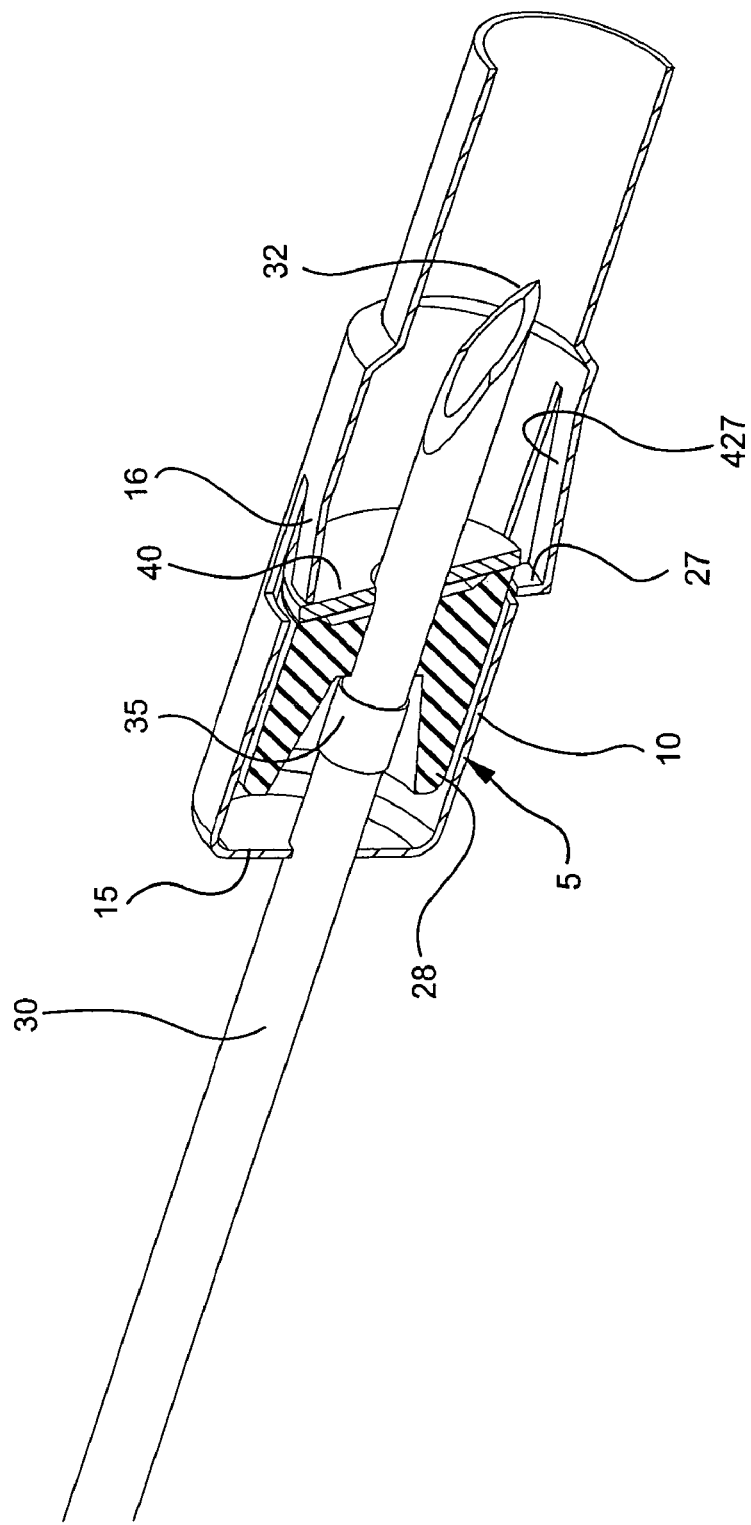
FIG. 12C is a perspective view of the needle shield assembly depicted in FIG. 11C in partial cross-section.

As the needle 30 is displaced distally with respect to the needle shield assembly 5, the friction member 28 is urged by friction with the needle 30 in the distal direction. As the friction member engages the canting plate 40, the canting plate is also urged distally. The alignment arm 19, which abuts a portion of the canting plate, restrains that portion, causing the canting plate to tilt to an off alignment, or actuated, condition, as seen in FIG. 8C. As depicted in FIGS. 8C and 9C, the feature 35 engages the friction member, causing it to move distally and engage the canting plate. As seen in FIGS. 11C and 12C, the friction member can be more tightly fit on the needle such that it moves with the needle whether the feature engages the friction member or not. In either case, when the canting plate 40 is tilted, the edge 43 of the hole 42 in the canting plate then binds on the exterior of the needle, preventing further displacement of the needle 30 with respect to the canting plate 40 (and thus the needle shield assembly 5). The shield body 10 of the needle shield assembly is long enough to ensure that the tip 32 of the needle 30 does not reemerge from the distal end 11 of the needle shield assembly when the canting plate is actuated.

Canting Plate with Rubber Washer and Interlock

Figure 10A:
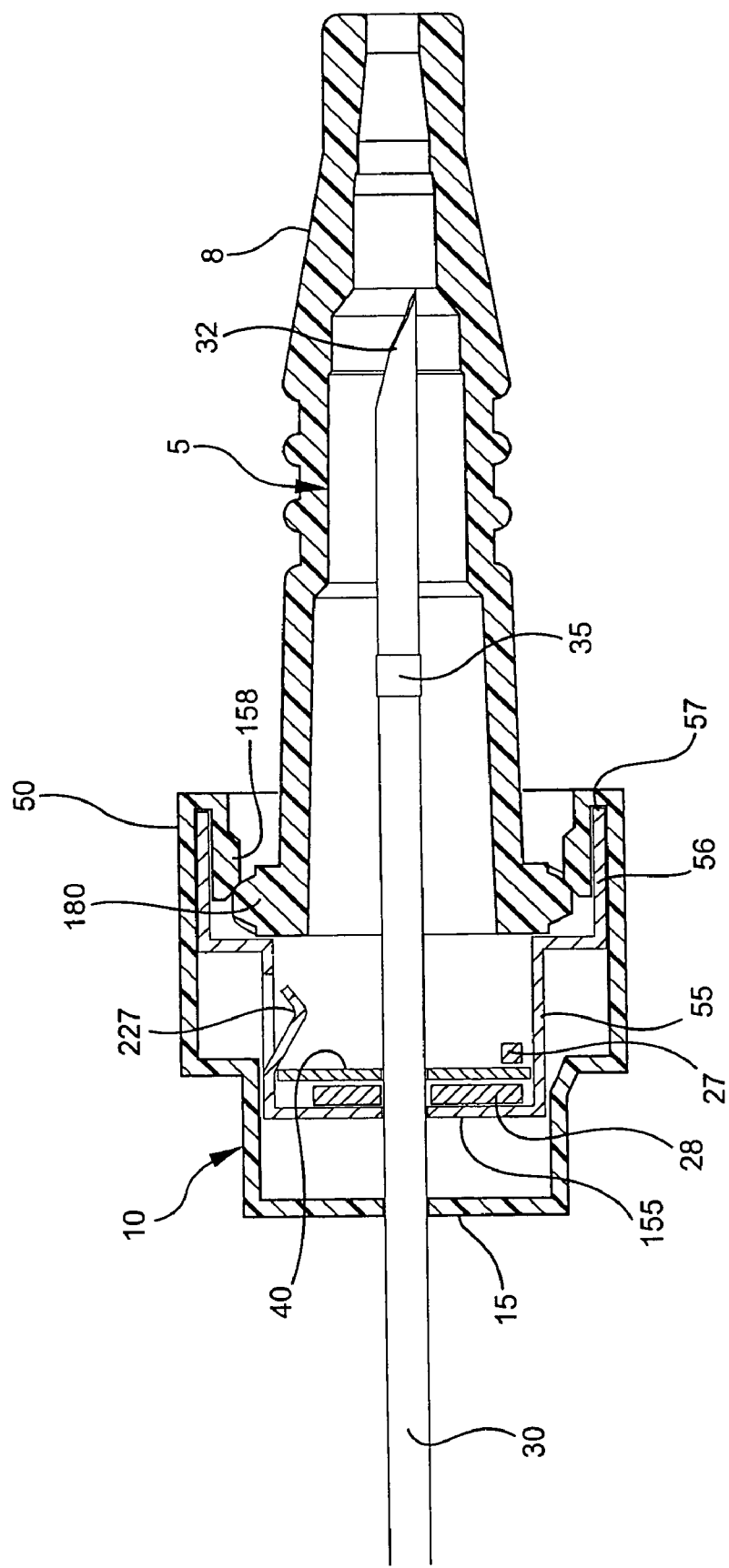
FIG. 10A is a cross-sectional view of another embodiment of the invention in which the canting plate is actuated by friction on the needle and including an interlock, shown in an unactuated condition, where the needle has been partly withdrawn through the catheter but the sharp distal tip of the introducer needle has yet to be withdrawn into the needle shield.
Figure 10B:
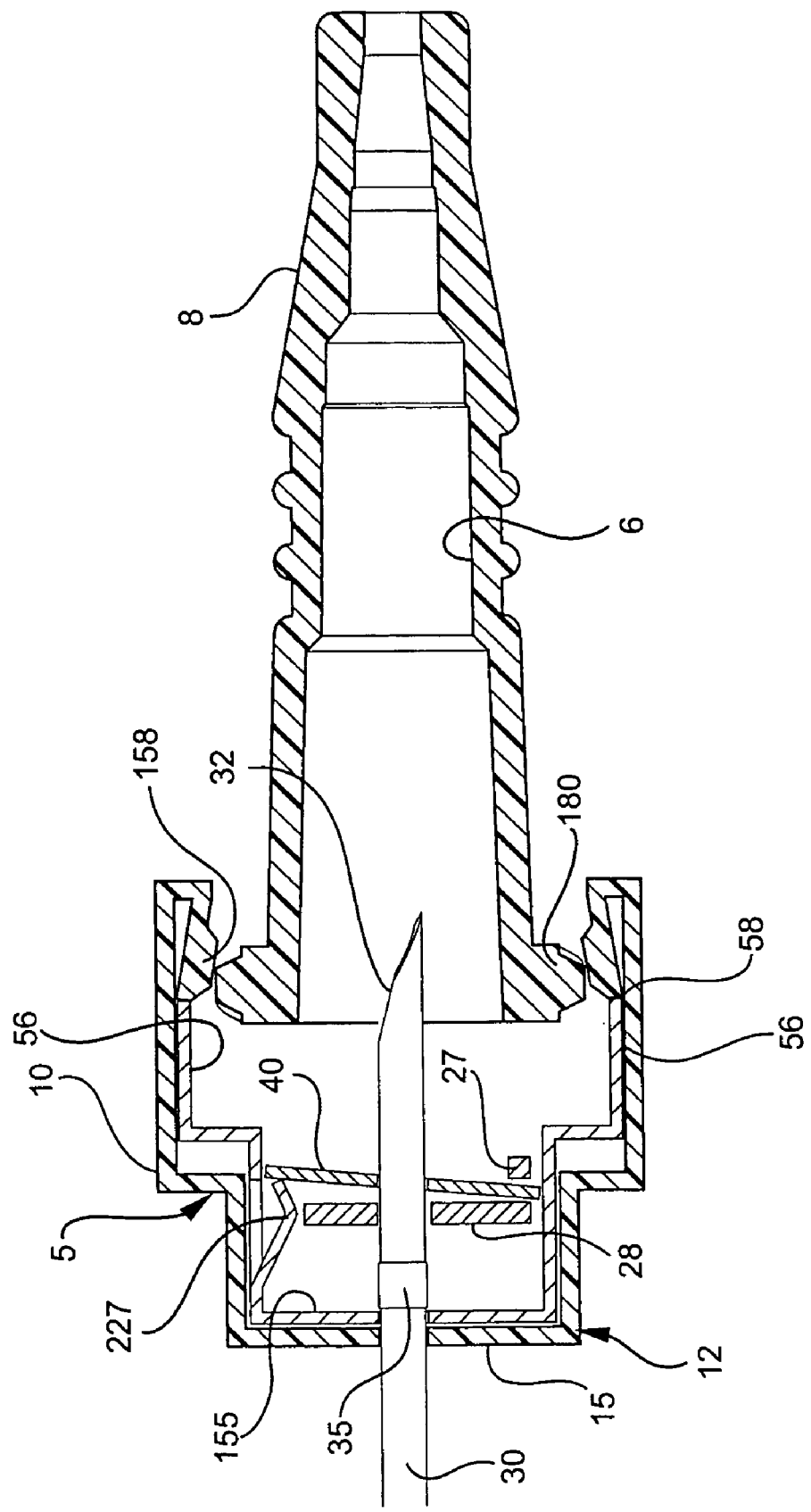
FIG. 10B is a cross-sectional view of the embodiment in FIG. 10A where the sharp distal tip of the introducer needle has been withdrawn proximally into the needle shield assembly and the catheter adapter has been partially removed.

A further implementation of an aspect of the instant invention is illustrated in FIGS. 10A-B. An interlock 50 is included to lock the catheter adapter 8 to the shield body 10 until the needle 30 is in a shielded position. The static feature 35 on the needle is employed to activate an adapter release 55, thereby disengaging the needle shield assembly 5 from the catheter adapter. The canting plate 40 is maintained in the aligned position by the elastomeric washer 28, the ledge 27 and an alignment arm 227. The ledge is fixedly attached to the needle shield assembly 5. The alignment arm may be in the form of a leaf spring attached to the adapter release 55.

Figure 10C:
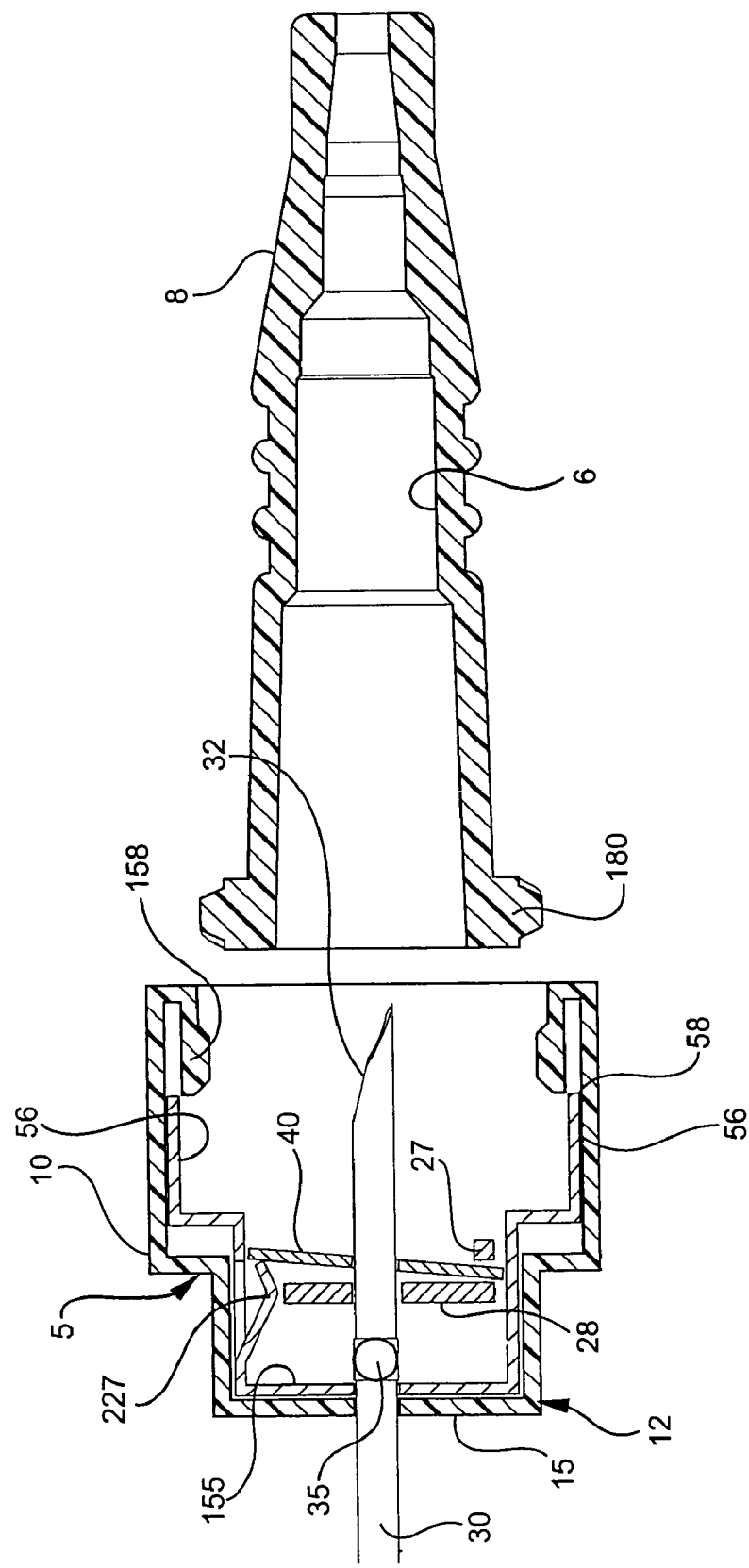
FIG. 10C is a cross sectional view of the embodiment of FIG. 10A where the sharp distal tip of the introducer needle has been withdrawn proximally into the needle shield assembly and the catheter adapter has been completely removed.

As shown in FIG. 10B, the static feature 35 on the needle 30, prior to bottoming out on the proximal end 12 of the shield body or the retention washer 15, engages the proximal wall 155 of a release pin 56, dragging it from a distal position 57 to a proximal position 58 (compare FIGS. 10A and 10B). The needle shield assembly 5 includes locking flanges 158 in the form of leaf springs attached near the distal end of the needle shield assembly and extending proximally. In their original, undeformed condition, the flanges extend relatively straight (that is, parallel to the axis of the needle shield assembly 5) (FIG. 10C). When assembled, the locking flanges 158 engage the collar 180 of the adapter 8, preventing the collar (and thus the adapter) from coming out of the needle shield assembly. See FIG. 10A. When it is in the distal position 57 shown in FIG. 10A, the release pin 56 prevents the locking flanges 158 from displacing radially inward. As the release pin is moved to the proximal position 58, it disengages the flanges 158 such that they are free to flex radially outwardly. Thus, as the catheter adapter 8 is displaced distally with respect to the needle shield assembly, the collar forces the locking flanges radially outwardly, as seen in FIG. 10B, thereby allowing the collar to slide passed the locking flanges. Consequently, the needle shield assembly 5 may slide off the adapter 8. As depicted in the drawings, the distal opening 13 of the needle shield assembly 5 is open, even after the needle tip 32 is shielded. It will be appreciated that the length of the needle shield clips or other such mechanisms further may be employed to create a transverse barrier to further prevent reemergence. Further, static feature 35 is employed to resist slipping the needle shield assembly 5 off the tip 32 of the needle 30. It will be appreciated that other structures, such as a tether, may be employed to prevent such removal.

In use, the needle tip 32 of the catheter assembly 100 is inserted into the patient's vein, positioning the catheter 108 in the vein as well. The needle 30 is withdrawn through the catheter 108 and the catheter adapter 8. The needle exerts a friction force on the washer 28. The washer is retained in position by the proximal wall 155 of the adapter release 55. When the feature 35 on the needle engages the proximal wall, it cannot fit through the opening in the wall, and pulls the adapter release proximally with respect to the shield body 10. As the adapter release moves proximally, the alignment arm 227 deflects over the canting plate 40. The alignment arm has an angled shape such that, when it is moved distally, it then tilts the canting plate to an off alignment condition. The adapter release continues to move within the shield body until the proximal wall 155 contacts the proximal end 12 of the shield body. At that point, further distal movement of the needle with respect to the needle shield assembly is prevented (see FIG. 10B).

As the adapter release 55 is moved from its distal position 57 to its proximal position 58, the release pin 56 is withdrawn from engagement with the locking flange 158. The locking flange is then free to displace radially outwardly as the collar 180 forces its way out of the needle shield assembly. As such, the needle shield assembly 5 can be separated from the adapter 8.

As the needle 30 is urged distally with respect to the needle shield assembly 5, friction between washer 28 and the needle urges the washer distally as well. The washer engages the canting plate 40, urging it distally. The canting plate is restrained at one edge by the ledge 27. Consequently, as the needle is moved distally, the canting plate is tilted more, binding more firmly on the needle and preventing further movement of the needle with respect to the needle shield assembly 5.

Canting Plate with Spring Arm Retention

Referring to FIGS. 11A-C and 12A-C, this implementation of the invention is similar in operation to that depicted in FIGS. 8A-C and 9A-C. However, in this implementation, a spring arm 427 is compressed radially inward before actuation to assist in maintaining the canting plate 40 in alignment before use. See FIG. 11A. The canting plate 40 is maintained in alignment before actuation by the cooperation of elastomeric washer 28 with retention arm 16 and ledge 27. Before the needle shield assembly 5 is actuated, the needle 30 can be moved proximally and distally within the assembly. In use, the needle is withdrawn until the feature 35 contacts the retention washer 15. Further movement of the needle causes the needle shield assembly 5 to pull out of the shield housing 6 in the adapter 8. See FIG. 11C. At that point, the spring arm 427 moves radially outward to an unstressed condition. The ledge 27 therefore disengages the bottom edge of the canting plate 40, allowing it to rotate. As the needle is urged distally with respect to the needle shield assembly 5, it acts on the washer 28, urging it distally as well. The washer engages the canting plate, in turn, urging it distally. The top edge of the canting plate is prevented from moving by retention arm 16. Consequently, the canting plate is rotated onto and binds onto the needle 30, preventing further proximal movement. See FIG. 11C.

Single Bi-Directional Canting Plate

Figure 13A:
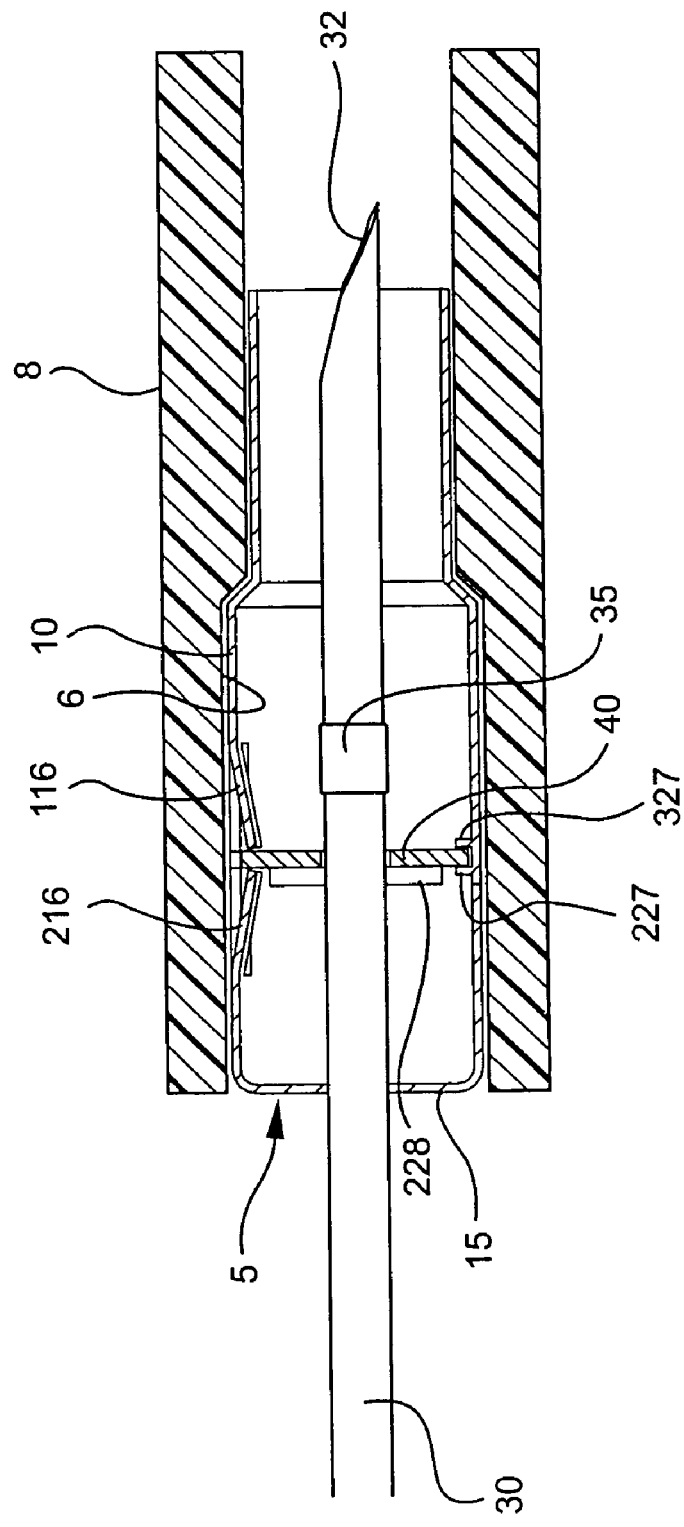
FIG. 13A is a cross-sectional view of another embodiment of the invention in which the canting plate is actuated by friction on the needle shown in an unactuated condition where the needle has been partly withdrawn through the catheter but the sharp distal tip of the introducer needle has yet to be withdrawn into the needle shield.
Figure 13B:
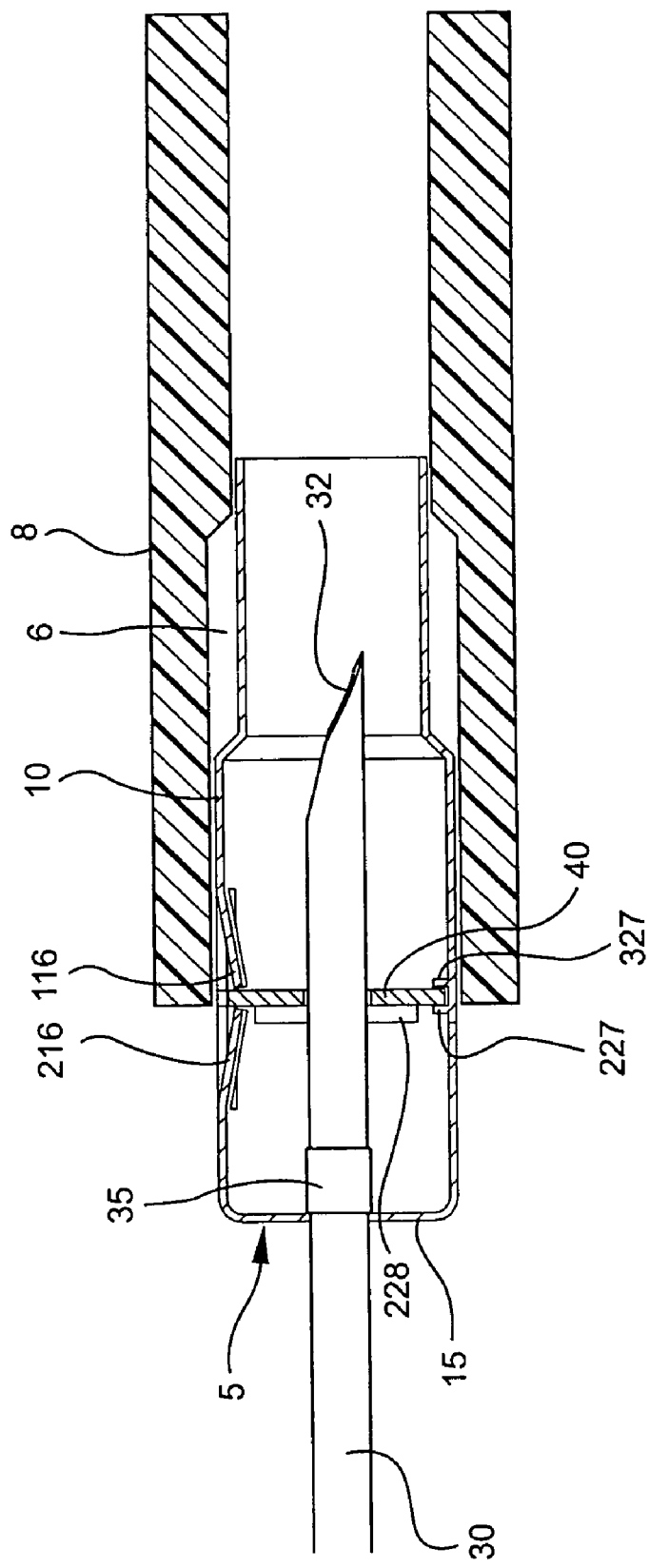
FIG. 13B is a cross-sectional view of the embodiment in FIG. 13A where the sharp distal tip of the introducer needle has been withdrawn proximally into the needle shield assembly.
Figure 13C:
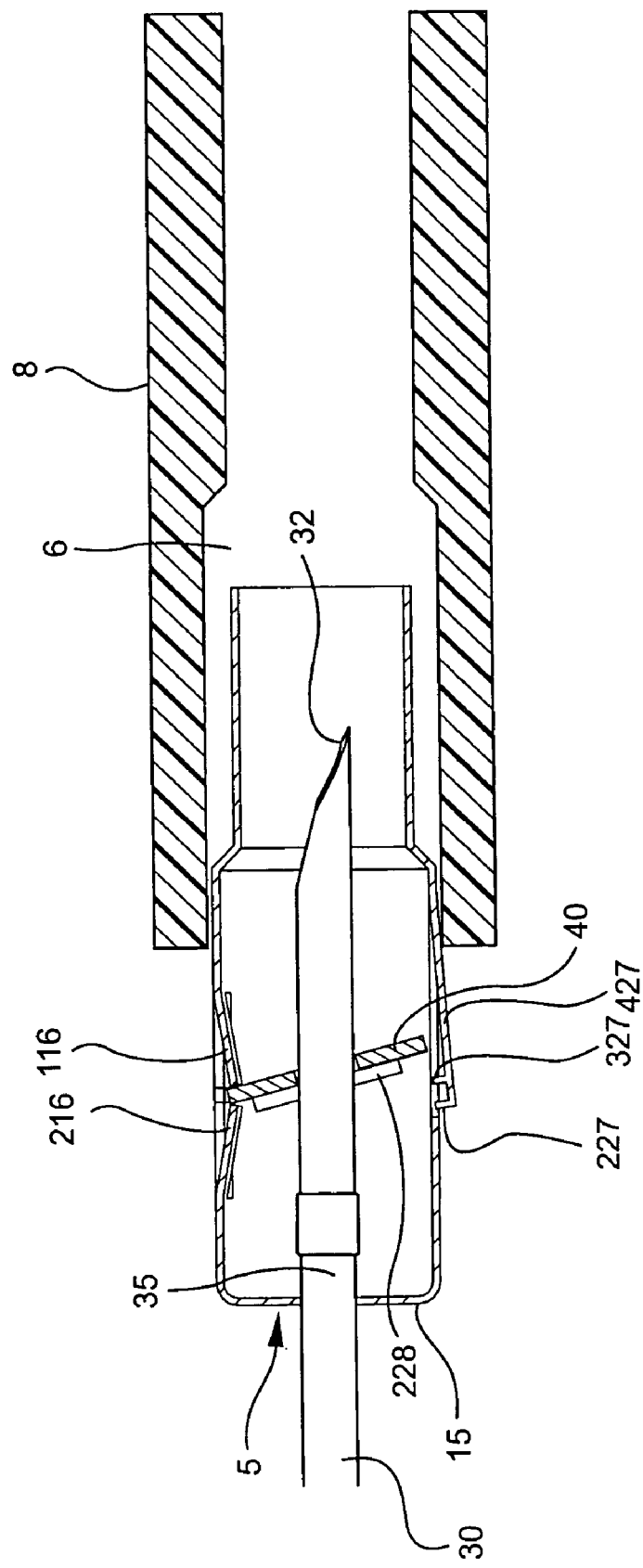
FIG. 13C is a cross-sectional view of the embodiment in FIG. 13A where the sharp distal tip of the introducer needle is being urged distally and the canting plate is tilted in an actuated condition.

FIGS. 13A through 13C depict another implementation of an aspect of the invention including a single canting plate 40 which binds onto the needle 30, thereby preventing movement of the needle with respect to the needle shield assembly 5 in both the proximal and distal directions. The needle shield assembly includes a proximal retention arm 216 and a distal retention arm 116 integrally formed with the shield body 10. A proximal ledge 227 and a distal ledge 327 are mounted on spring arm 427. As depicted in FIG. 13A, the shield housing 6 of the adapter 8 compresses or flexes the spring arm radially inwardly, and into engagement with the canting plate 40. An elastomeric washer 228 is attached to the canting plate and is frictionally engaged to the needle. A feature 35 is permanently attached to the needle. The retention washer 15 at the distal end of the needle shield assembly includes an opening 14 that is sized to permit movement of the needle therethrough but to prevent passage of the feature 35.

In use, the user inserts the needle tip 32 of the over-the-needle catheter assembly 10 into the patient's vein. Upon confirmation flashback, the user grasps the needle hub 110, pulling the needle hub away from the catheter adapter 8, thereby causing the needle 30 to be withdrawn through the catheter adapter 8 and the needle shield assembly 5. See FIG. 13A. The needle continues to be withdrawn through the needle shield assembly until the feature 35 contacts the retention washer 15. Further displacement of the needle causes the needle shield assembly 5 to be withdrawn from the shield housing 6 in the adapter 8. See FIG. 13B. As the needle shield assembly is fully withdrawn from the shield housing in the catheter adapter, the spring arm 427 is free to rotate radially outward from the needle shield assembly. Consequently, the proximal ledge 227 and the distal ledge 327 disengage the canting plate 40. See FIG. 13C. Consequently, the canting plate can be rotated. The upper edge of the canting plate is prevented from moving either distally or proximally by the retention arms 116, 216.

Double Canting Plate

Figure 14A:
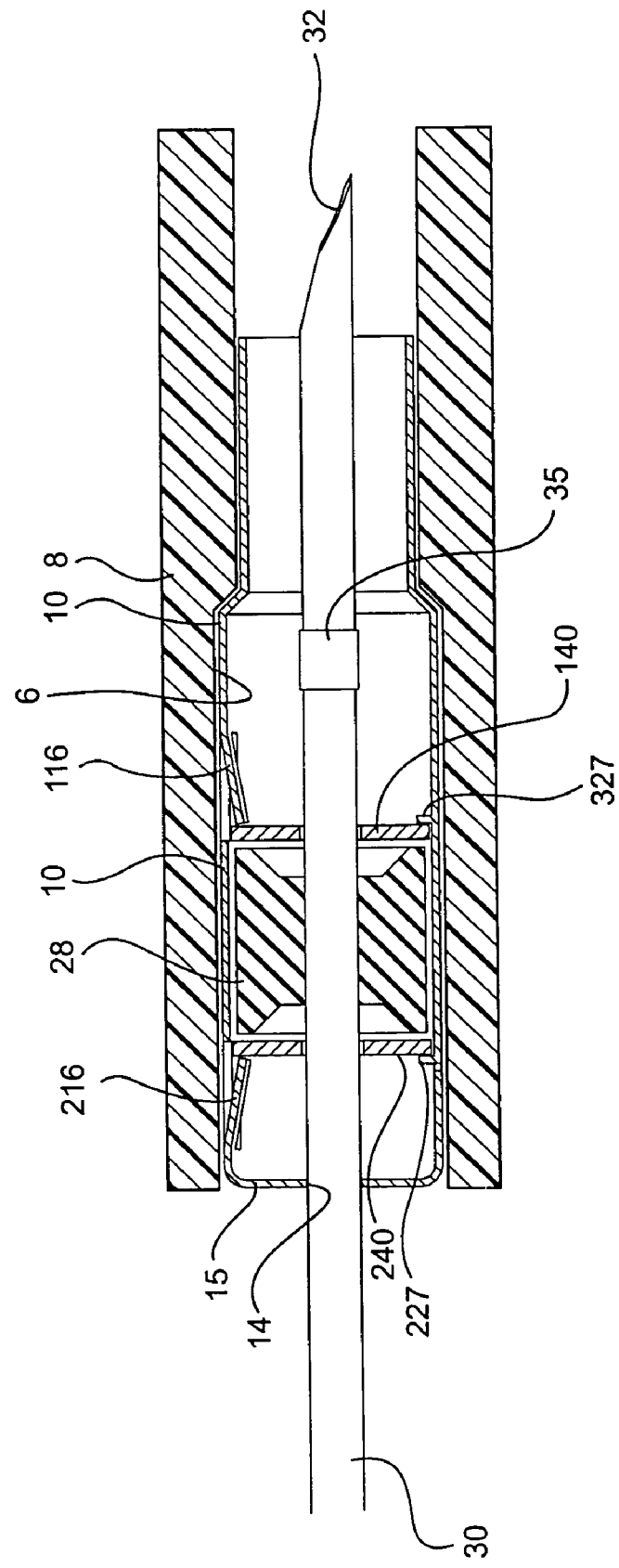
FIG. 14A is a cross-sectional view of another embodiment of the invention in which the canting plate is actuated by friction on the needle, shown in an unactuated condition, where the needle has been partly withdrawn through the catheter but the sharp distal tip of the introducer needle has yet to be withdrawn into the shield.
Figure 14B:
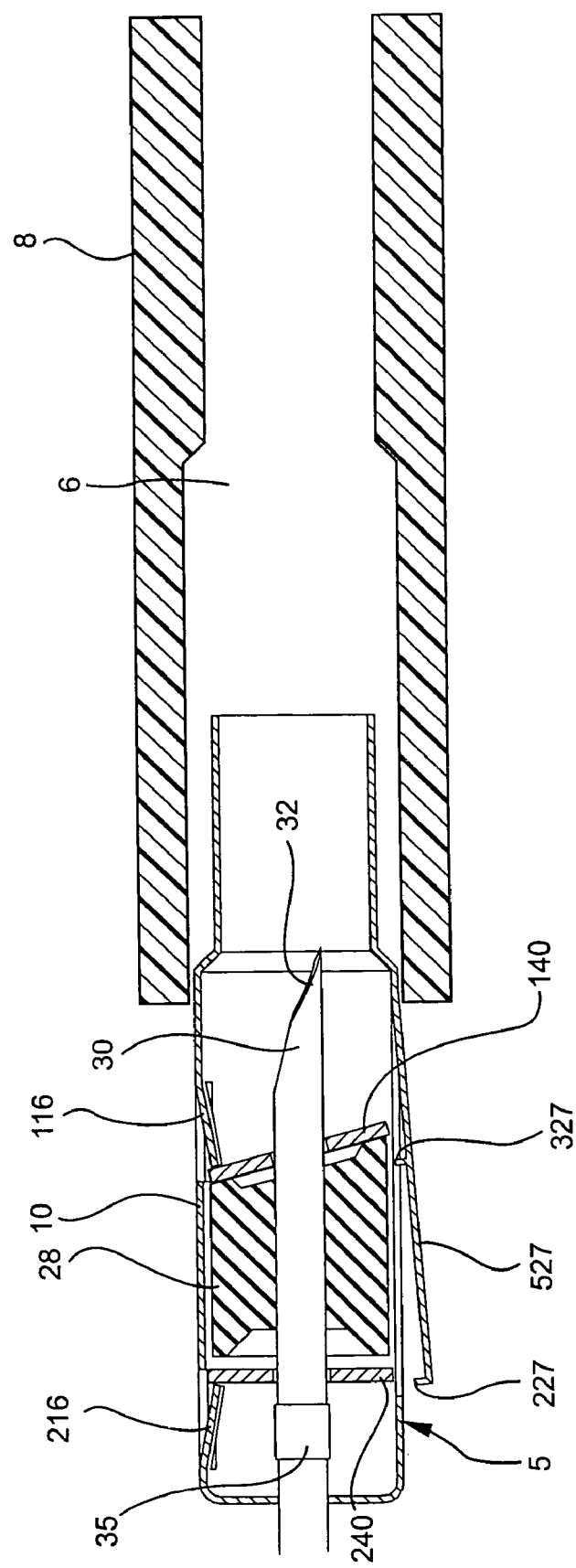
FIG. 14B is a cross-sectional view of the embodiment in FIG. 14A where the sharp distal tip of the introducer needle has been withdrawn proximally into the needle shield assembly.
Figure 14C:
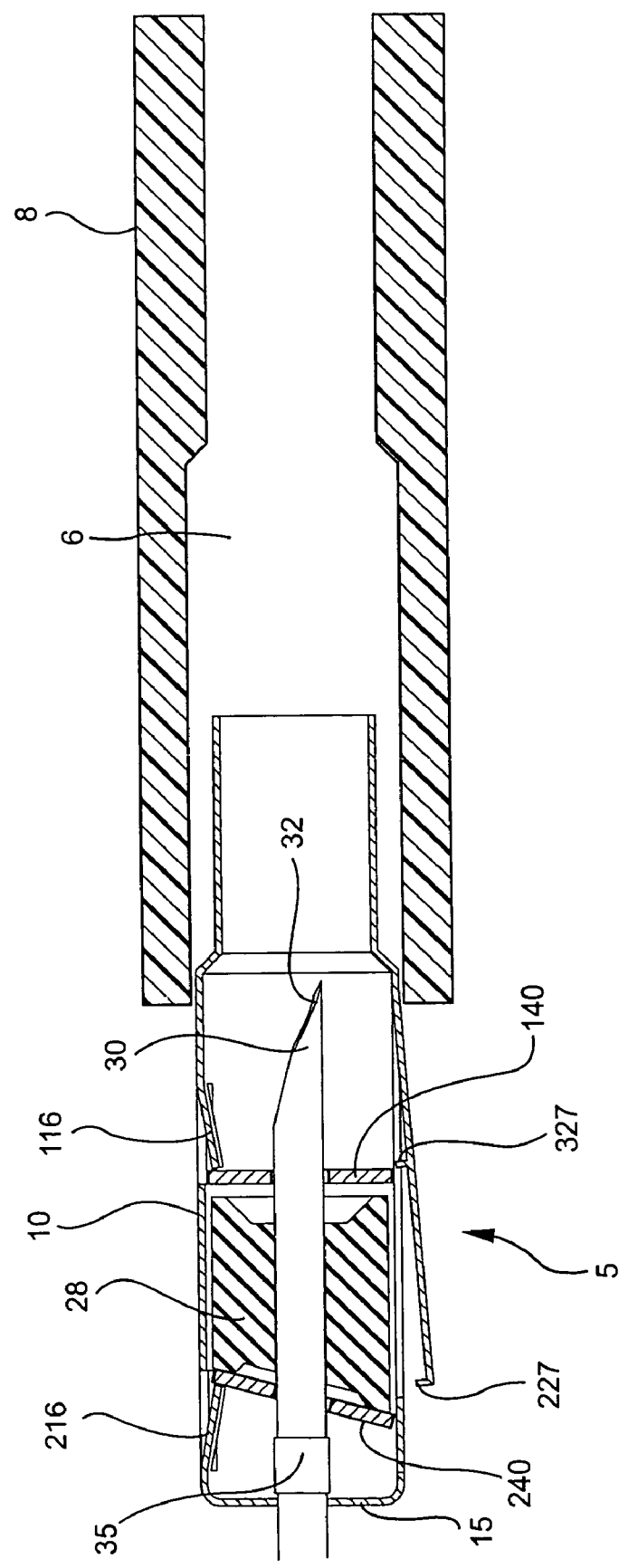
FIG. 14C is a cross-sectional view of the embodiment in FIG. 14A where the sharp distal tip of the introducer needle is being urged distally and the canting plate is tilted to an actuated condition.

Another implementation of the invention is disclosed in FIGS. 14A through 14C. The needle shield assembly 5 includes a distal retention arm 116 and a proximal retention arm 216 which are preferably integrally formed with the shield body 10. As depicted, the retention arms are deformed radially inward, such as by bending. A distal canting plate 140 and a proximal canting plate 240 are disposed within the shield body. The canting plates are maintained in an aligned condition by the cooperation of the retention arms with distal ledge 327 and proximal ledge 227 and the elastomeric washer 28, discussed below. The ledges 227, 327 are mounted to a spring arm 527. When the needle shield assembly is disposed within the shield housing 6 of adapter 8, the spring arm 527 is biased radially inward such that the ledges 227, 327 engage the canting plates 140, 240. A friction member, such as hourglass-shaped washer 28, is disposed between the distal canting plate 40 and the proximal canting plate 240 within the shield body 10. The elastomeric washer 28 is frictionally engaged to the needle. In certain implementations of this aspect of the invention, the elastomeric washer 28 may be compressed when disposed between the two canting plates as depicted in FIG. 14A. In such case, the washer is exerting a continuous biasing force on the canting plates which is resisted by the needle shield assembly.

In use, needle tip 32 of the over-the-needle catheter assembly 100 is inserted into the patient's vein. Upon confirmation flashback, the needle 30 is withdrawn through the catheter 108 such that the needle passes through the needle shield assembly 5. The distal canting plate 140 is maintained in alignment with the needle by the cooperation of the elastomeric washer 28, the distal retention arm 116 and the distal ledge 327. The proximal canting plate 240 is maintained in alignment by the cooperation of the elastomeric washer, the proximal retention arms 216 and the proximal ledge 227 despite urging of the washer 28 (which is seeking to follow the needle and, thus, being moved against the canting plates). Since the canting plates are in alignment with the needle, the needle passes freely through the openings in the canting plates. Upon further withdrawal of the needle, the feature 35 engages the retention washer 15, causing the needle shield assembly 5 to be pulled out of the shield housing 6 in the adapter 8. See FIG. 14B. Upon removal of the needle shield assembly from the catheter adapter, the spring arm 527 is free to expand radially outward from the shield body, such that the proximal ledge 227 disengages the proximal canting plate 240 and the distal ledge 327 disengages the distal canting plate 140. This disengagement permits the canting plate to rotate. If the washer had been compressed, it will be free to expand, thereby causing immediate tilting of the canting plates. As the needle 30 is urged proximally with respect to the needle shield assembly 5, the needle will urge the washer 28 distally which, in turn, will cause the proximal canting plate 240 to rotate, as seen in FIG. 14B. As the needle is urged distally with respect to the needle shield assembly, the washer 28 will move distally, urging the distal canting plate 140 to move distally. The distal retention arm 116 will prevent the distal canting plate 140 from translating distally within the needle shield body 10, resulting in tilting of the distal canting plate and binding on the needle. See FIG. 14C.

Dual Canting Plate with Tether

Figure 15A:
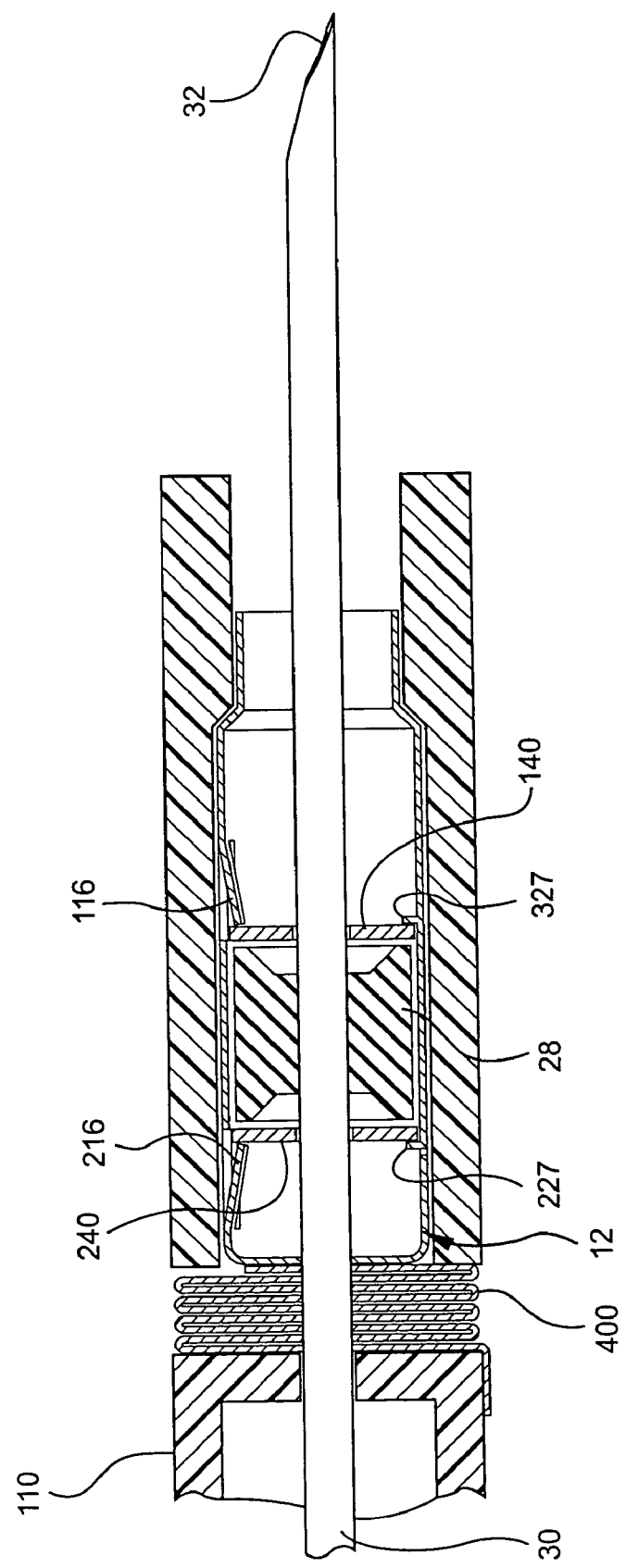
FIG. 15A is a cross-sectional view of another embodiment of the invention in which the canting plate is actuated by friction on the needle, and including a tether to connect a needle hub to the needle shield assembly, shown in an unactuated condition, where the needle has been partly withdrawn through the catheter but the sharp distal tip of the introducer needle has yet to be withdrawn completely into the needle shield.
Figure 15B:
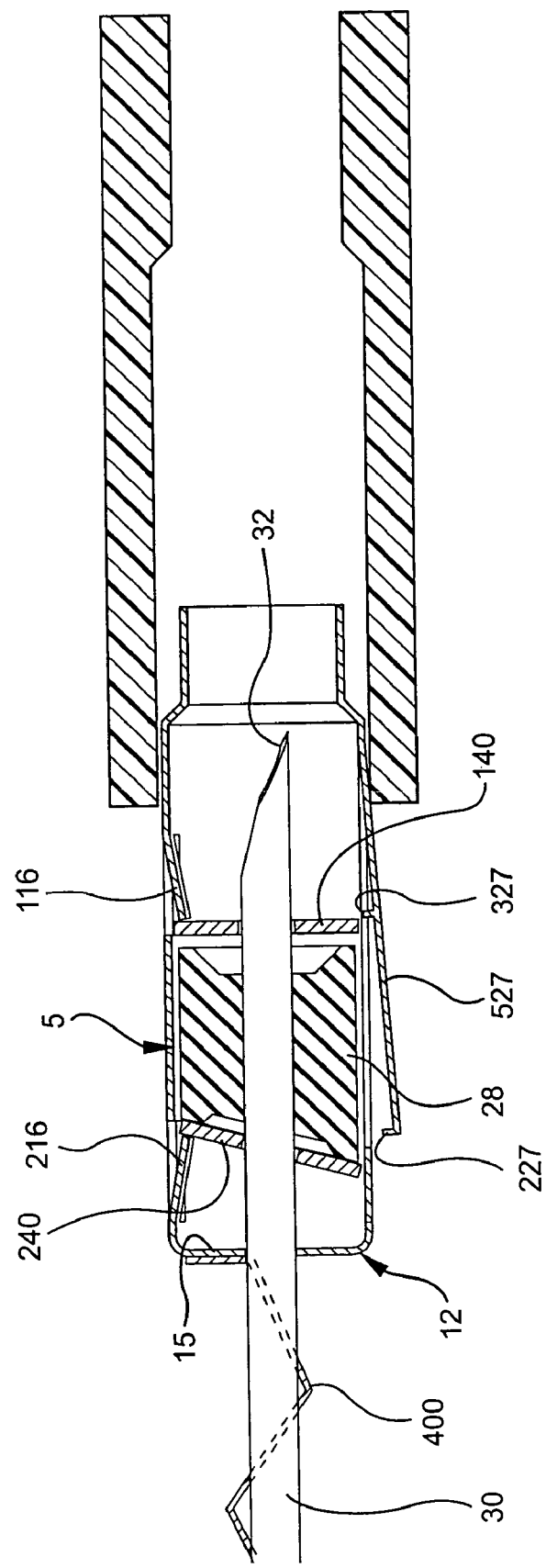
FIG. 15B is a cross-sectional view of the embodiment of FIG. 15A in which the sharp distal tip of the introducer needle has been withdrawn proximally into the needle shield assembly.
Figure 15C:
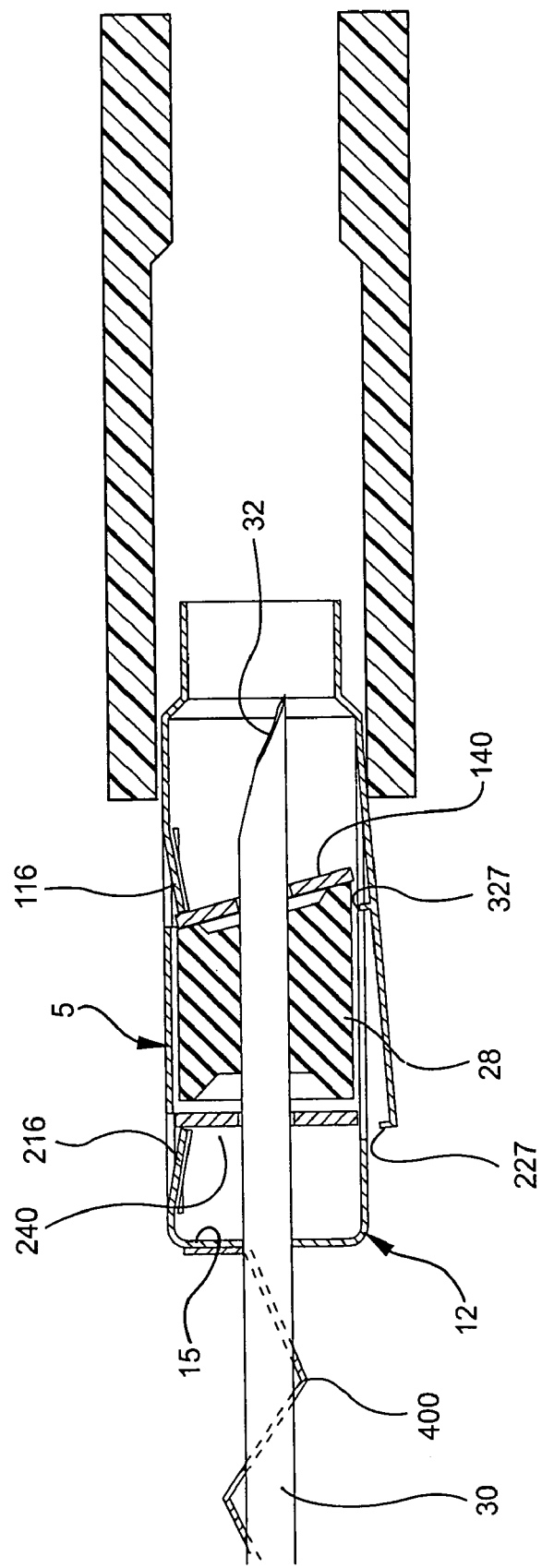
FIG. 15C is a cross-sectional view of the embodiment of FIG. 15B in which the sharp distal tip of the introducer needle is being urged distally and the canting plate is tilted to an actuated condition.

Referring to FIGS. 15A through C, an implementation of the invention is depicted which employs a tether 400 to extract the needle shield assembly 5 from the shield housing 6 of the catheter adapter 8. The tether is attached to the needle hub 110 and to the proximal end 12 of the needle shield assembly. As depicted in FIGS. 15A through C, the tether is attached to the retention washer 15. Because the tether extracts the needle shield assembly from the catheter adapter, no feature 35 on the needle is required. In use, the needle tip 32 is inserted into the patient's vein, delivering the tip of the catheter 108 to the vein as well. The caregiver then withdraws the needle hub 110 while holding the catheter adapter 8 in place. See FIG. 15B. As the needle hub is moved proximally, the tether 400 extends until it is at its full length. As the needle hub is moved further proximally, the needle shield assembly 5 is pulled out of the shield housing 6 in the catheter adapter 8. See FIG. 15B. The operation of this implementation is otherwise similar to the implementation depicted and described in connection with FIGS. 14A through 14C.

Single Canting Plate and Tether

Figure 16A:
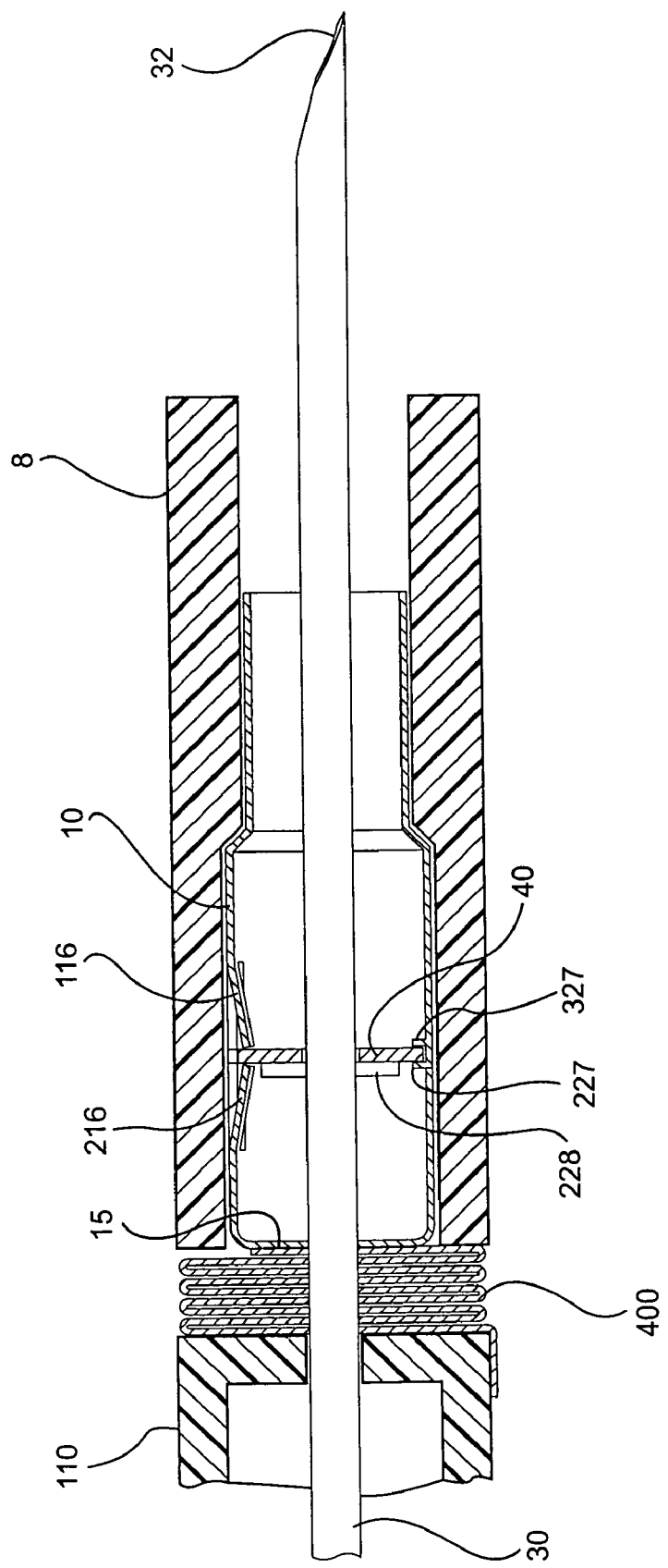
FIG. 16A is a perspective view of another embodiment of the invention in which the canting plate is actuated by friction on the needle, shown in an unactuated condition.
Figure 16C:
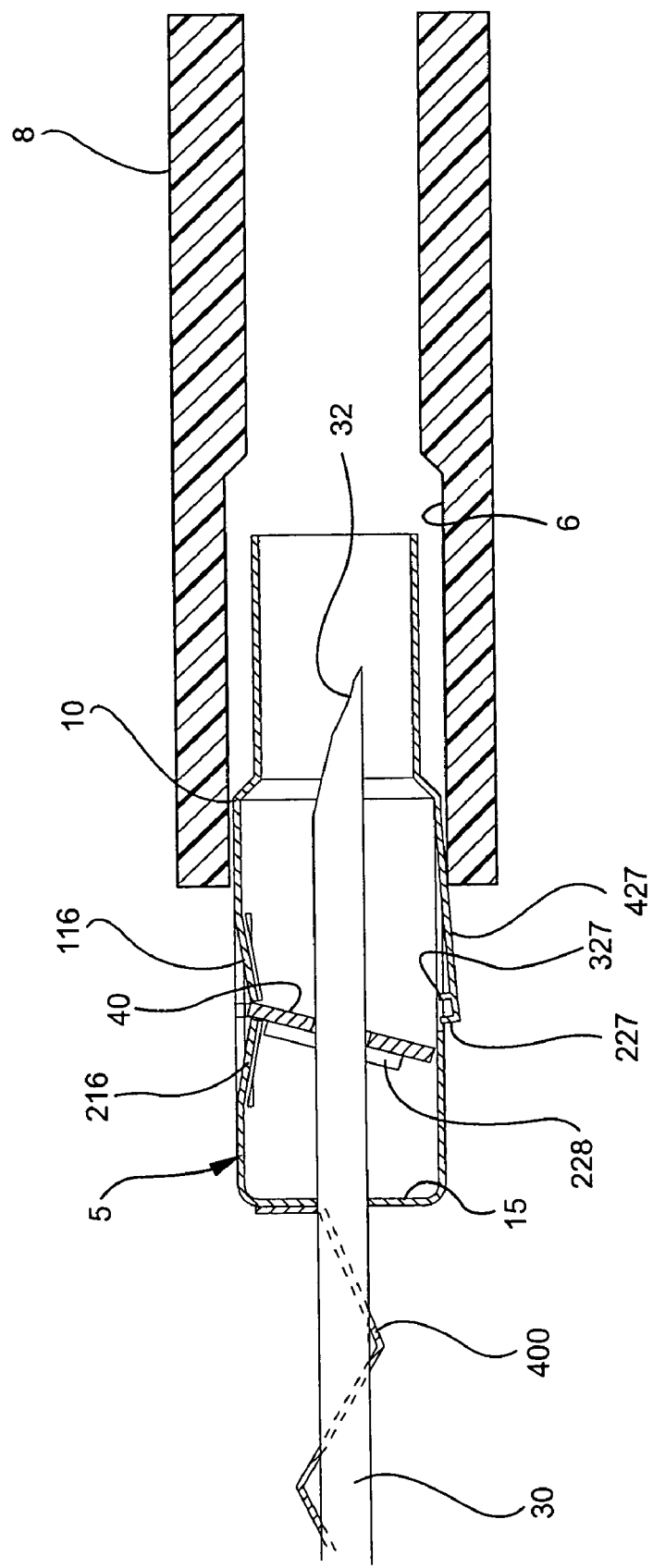
FIG. 16C is a cross-sectional view of the embodiment of FIG. 17A in which the sharp distal tip of the introducer needle has been withdrawn proximally into the needle shield assembly and the canting plate has been urged to engage the needle to prevent further proximal movement.
Figure 16D:
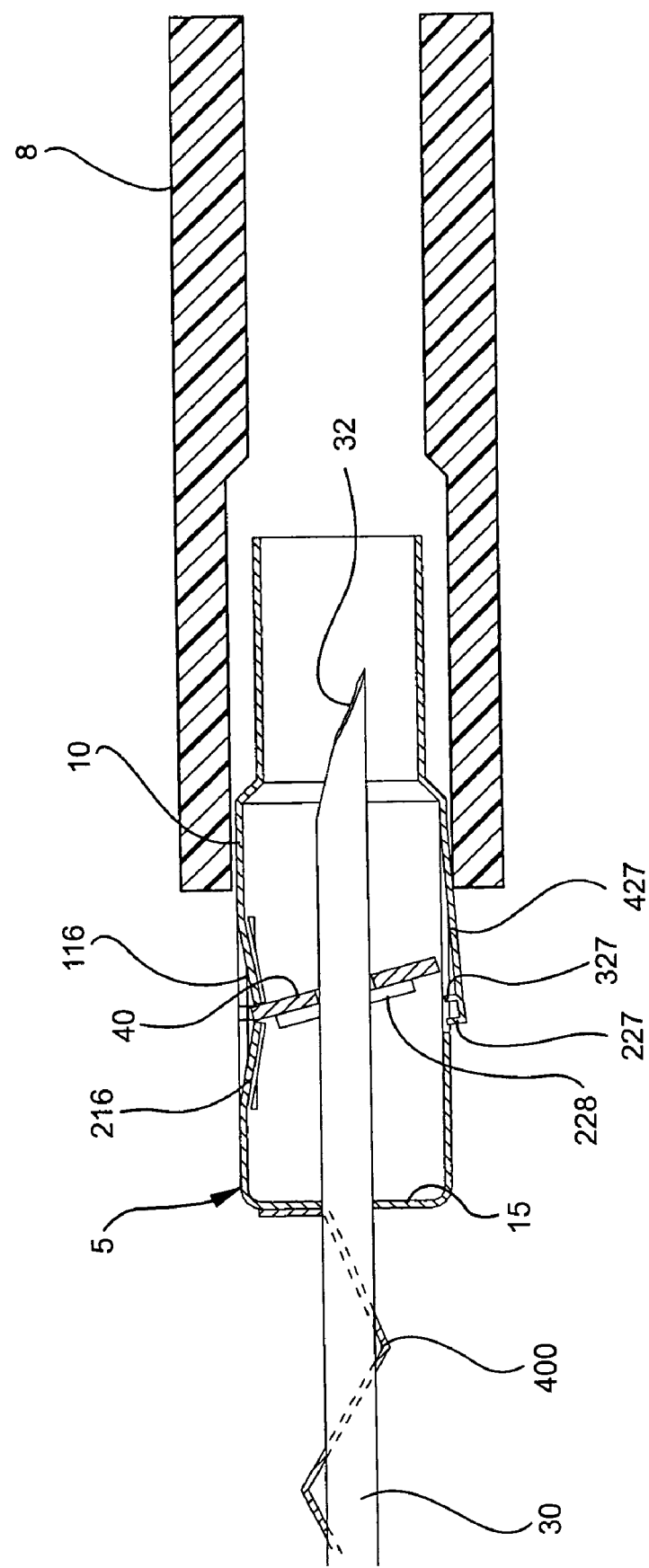
FIG. 16D is a cross-sectional view of the embodiment of FIG. 17A in which the sharp distal tip of the introducer needle is being urged distally and the canting plate is tilted to an actuated condition.

Referring now to FIGS. 16A through 16D, an implementation of the invention similar to that depicted in FIGS. 13A through 13C is depicted. However, a tether 400 is used to extract the needle shield assembly 5 from the shield housing 6 in the catheter adapter 8. Consequently, no feature 35 is required on the needle. A single canting plate 40 binds onto the needle 30 after actuation, thereby preventing movement of the needle with respect to the needle shield assembly in both the proximal and distal directions. The needle shield assembly 5 includes a proximal retention arm 216 and a distal retention arm 116 integrally formed with the shield body 10. A proximal ledge 227 and a distal ledge 327 are mounted on spring arm 427. As depicted in FIG. 16A, the shield housing 6 of the adapter 8 compresses or flexes the spring arm radially inwardly, and into engagement with the canting plate 40. An elastomeric washer 228 is attached to the canting plate and is frictionally engaged to the needle. A feature 35 is permanently attached to the needle.

In use, the user inserts the needle tip 32 of the over-the-needle catheter 100 into the patient's vein, thereby positioning the tip of the catheter 108 in the vein as well. Upon confirmation flashback, the user grasps the needle hub 110, pulling the needle hub away from the catheter adapter 8, thereby causing the needle 30 to be withdrawn through the catheter adapter 8 and the needle shield assembly 5. See FIG. 16B. When the tether 400 is extended to its full length, further proximal movement of the needle hub begins withdrawing the needle shield assembly from the catheter adapter. See FIG. 16B. As the needle shield assembly is fully withdrawn from the shield housing in the catheter adapter, the spring arm 427 is free to rotate radially outward from the needle shield assembly. Consequently, the proximal ledge 227 and the distal ledge 327 disengage the canting plate 40. See FIG. 16C. Consequently, the canting plate can be rotated. The upper edge of the canting plate is prevented from moving either distally or proximally by the retention arms 116, 216. Re-emergence of the needle is prevented by a binding force from the canting plate on the exterior wall of the needle 30, as discussed in connection with FIGS. 13A-C. See FIG. 16D.

Clip with Canting Slot

Figure 17A:
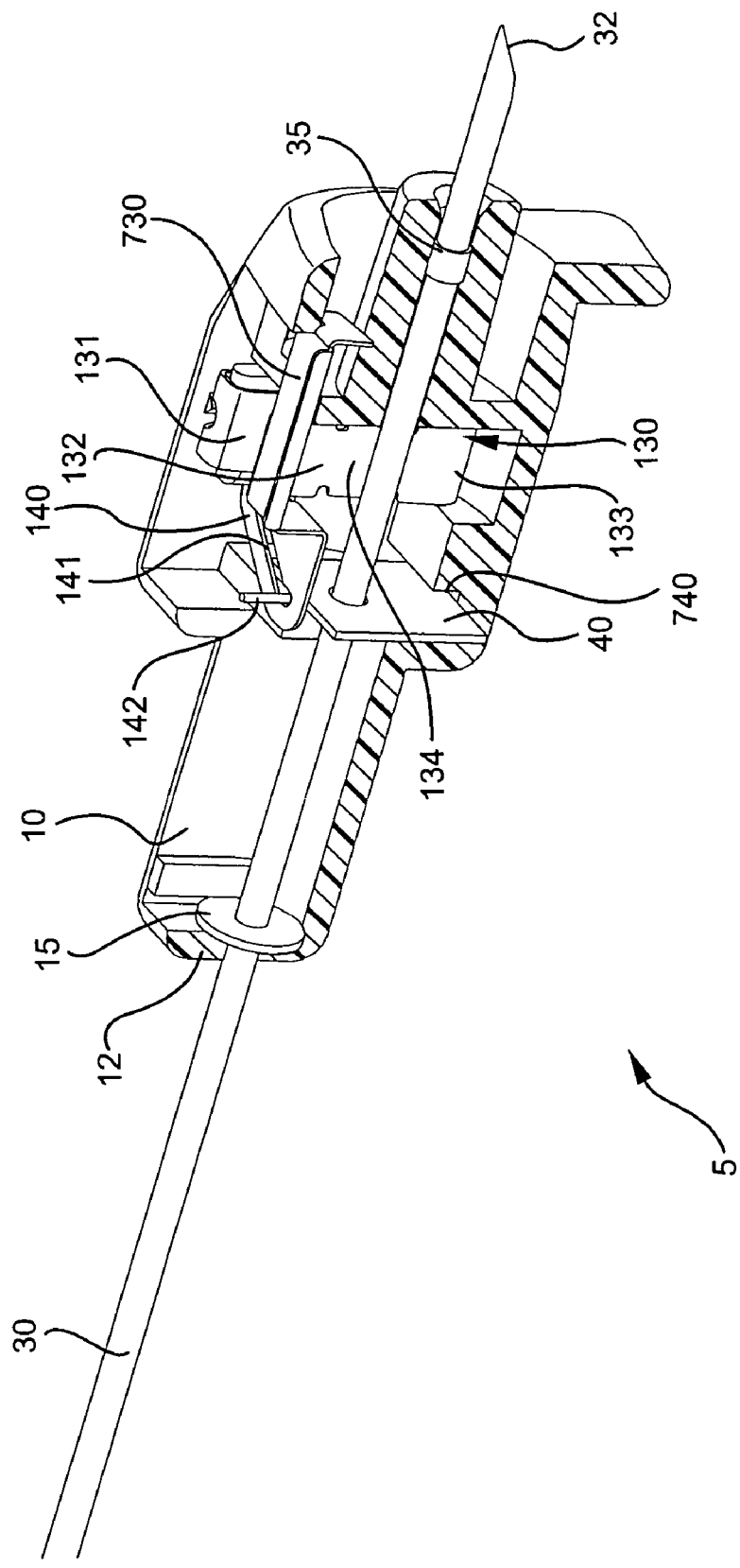
FIG. 17A is a perspective view in partial cross-section of another embodiment of the invention in which the canting plate is actuated by an angled guide on a clip, shown in an unactuated position.
Figure 17B:
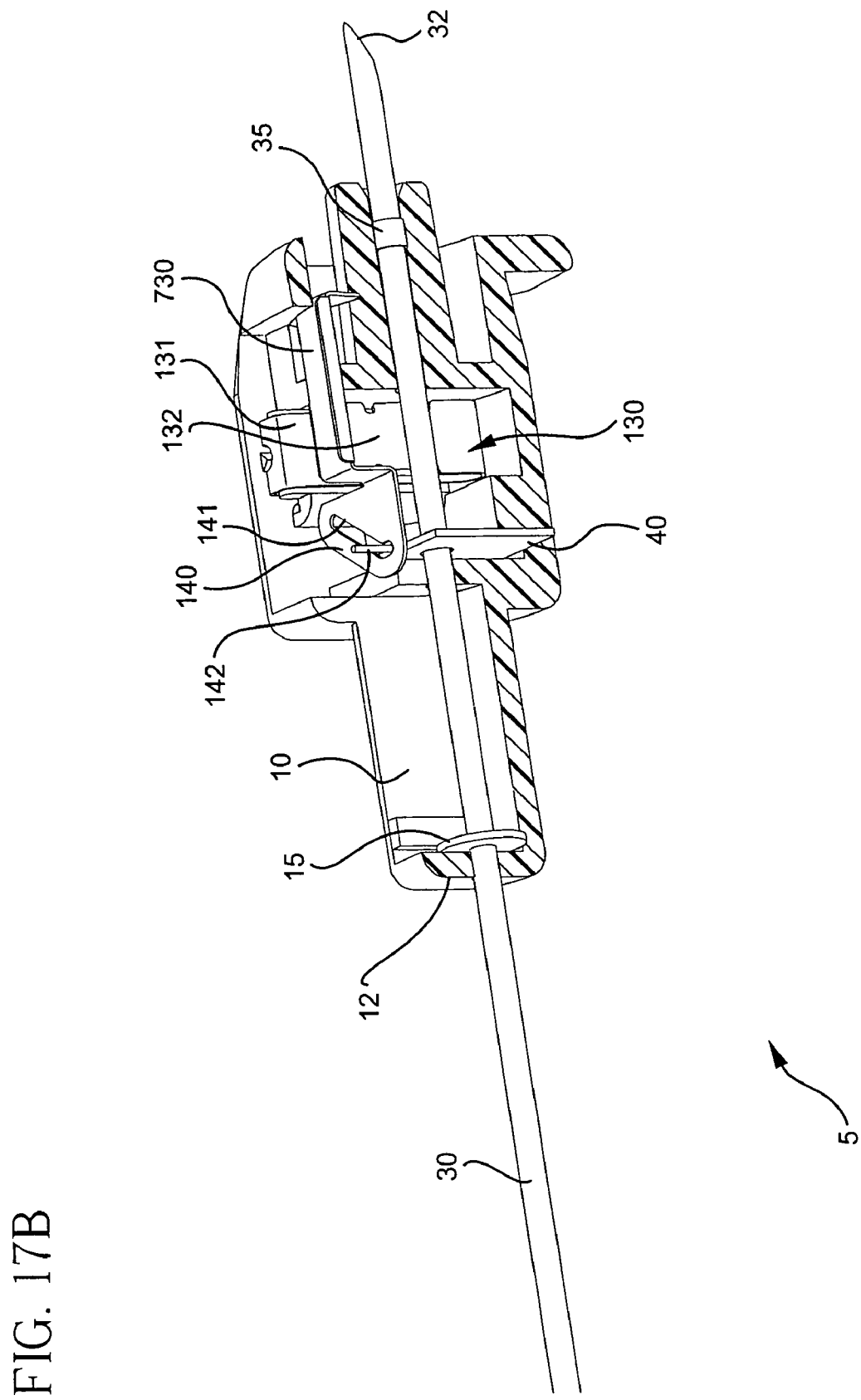
FIG. 17B is a rear perspective view of the embodiments depicted in FIG. 17A.
Figure 17C:
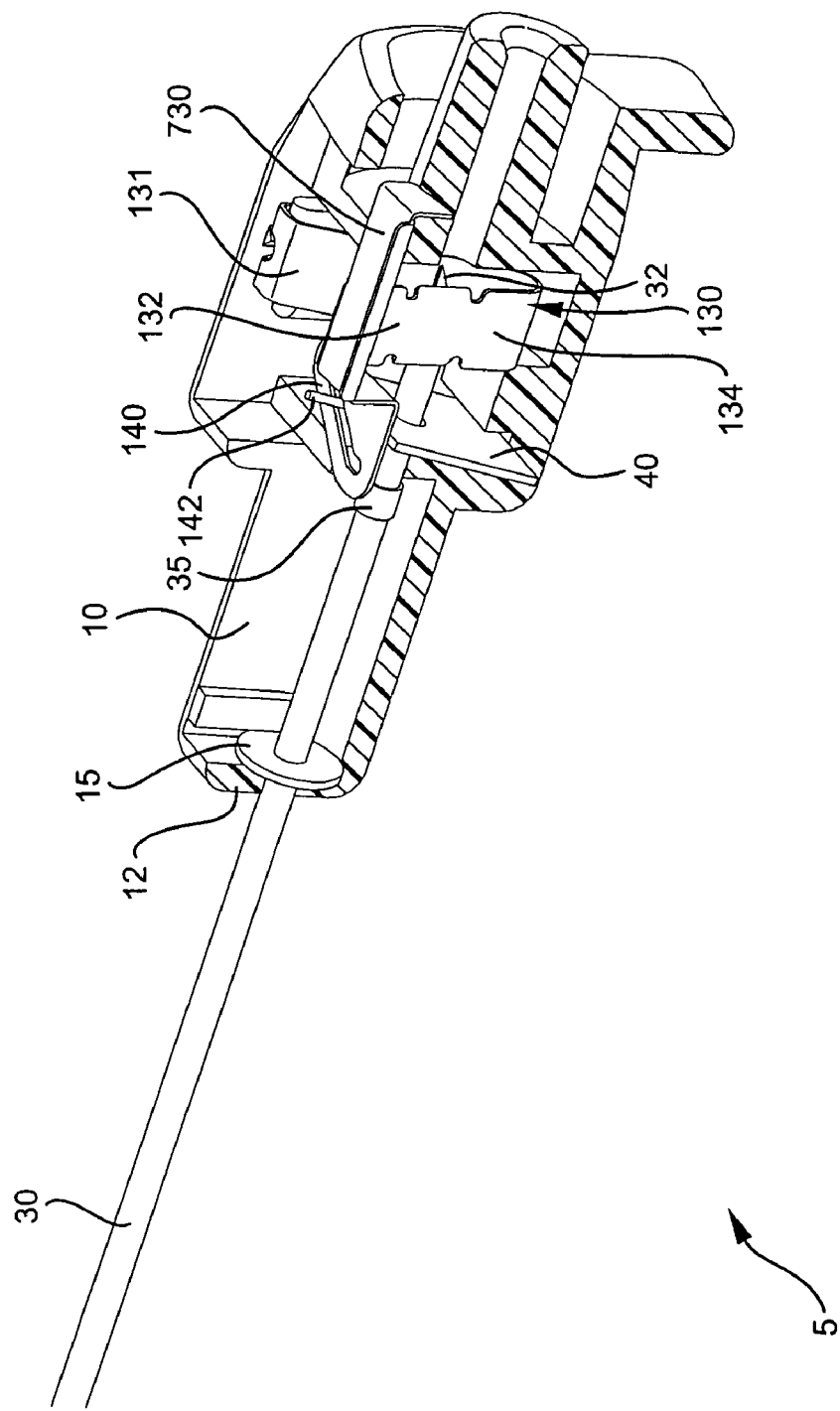
FIG. 17C is a front cross-sectional view of the embodiment in FIG. 17A shown in an actuated condition.
Figure 17D:
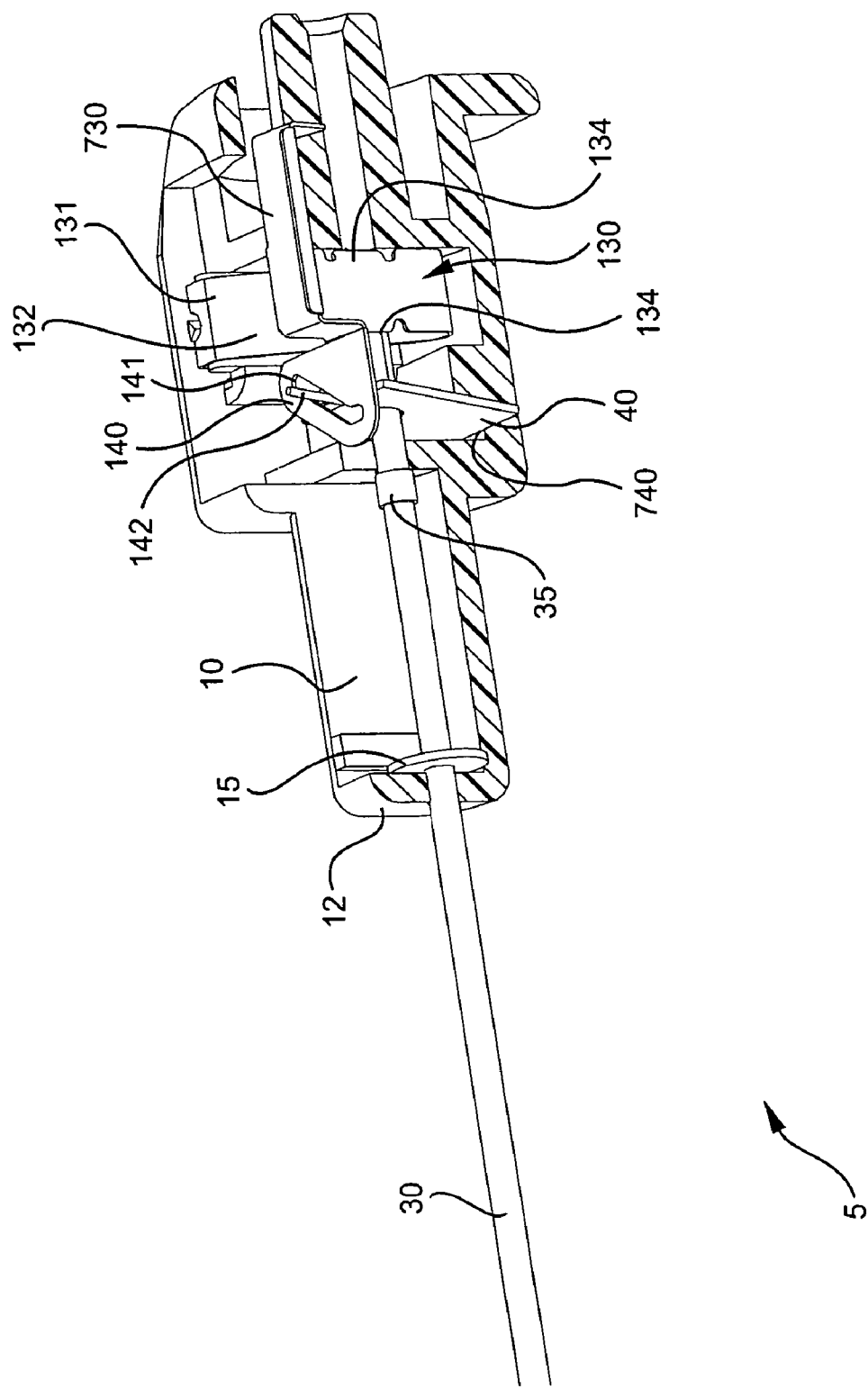
FIG. 17D is a rear perspective view of the embodiment depicted in FIG. 17A in an actuated condition.

Referring now to FIGS. 17A through 17D, an implementation of the invention is depicted in which a clip 130 is disposed within the housing of the needle shield assembly 5. The clip is a substantially v-shaped member with a first leg 131 securely mounted to the housing. The second leg 132 is mounted to the first leg via a flexural hinge 133. Slide tabs 134 are formed in the second leg to reduce the interference between the needle 30 and the second leg during actuation and slidingly engage the needle 30. As shown in FIGS. 17A and 17B, before actuation, the clip 130 is compressed and maintained in the compressed condition by the presence of the needle within the needle shield 5 at a point aligned with the clip. A trap arm 730 is attached to the second leg 132 and engages a catheter adapter (not shown), preventing its removal from the needle shield assembly. As the needle is withdrawn, it ceases to engage the second leg such that the flexural hinge 133 springs open. See FIGS. 17C and 17D. The trap arm then moves out of engagement with the catheter adapter so that it can be removed from the needle shield assembly.

A guide plate 140 is attached to the second leg 132 of the clip 130. The guide plate includes a guide slot 141. A canting pin 142 is attached to the canting plate 40. The canting pin may be integrally formed with the canting plate. The canting pin is disposed within the guide slot 141. In the unactuated condition, as shown in FIG. 17A, the position of the canting pin in the canting slot maintains the canting plate in an aligned condition with the needle 30. Consequently, the needle may be withdrawn through the opening in the canting plate without interference. As the needle is withdrawn beyond the clip, the clip springs open, causing the guide plate to move accordingly. See FIGS. 17C and 17D. The movement of the guide plate results in the pin 142 being displaced in a distal direction. The bottom edge of the canting plate is prevented from translating proximally or distally because it is retained within a groove 740 in the needle shield assembly housing. As the pin 142 is moved distally, the canting plate is rotated into binding engagement with the needle. As the needle is urged distally with respect to the needle shield assembly, the engagement of the canting plate prevents the needle from re-emerging out of the needle shield assembly. The retention washer 15 prevents movement of the feature 35 (and therefore movement of the needle tip 32) out of the proximal end of the needle shield assembly. It will be appreciated that the feature could be removed and a tether provided to prevent the needle shield assembly from sliding off the tip of the needle.

Integrated Washer and Floating Plate

Referring now to FIGS. 18A through 18D, an implementation of the invention is depicted including a retention washer 15 integrally formed with an actuator arm 150. An opening 14 is disposed in the retention washer. A lip may be formed about the opening 14 to ease the passage of the needle and to ensure relatively perpendicular alignment between the retention washer and the needle. The actuator arm includes a front wall 151 and a slide plate 152. An aperture 153 is disposed in the front wall but may be eliminated in certain implementations. The canting plate 40 is maintained in position about the needle by a pair of u-shaped sleeves 154. The sleeves are in a relatively close fit with the canting plate 40 but not so close that the canting plate cannot slide within the sleeves. Compare FIGS. 18B and 18D. The u-shaped sleeves are themselves attached to the arm 150. An aperture 155 is disposed in the arm directly above the canting plate.

Figure 18A:
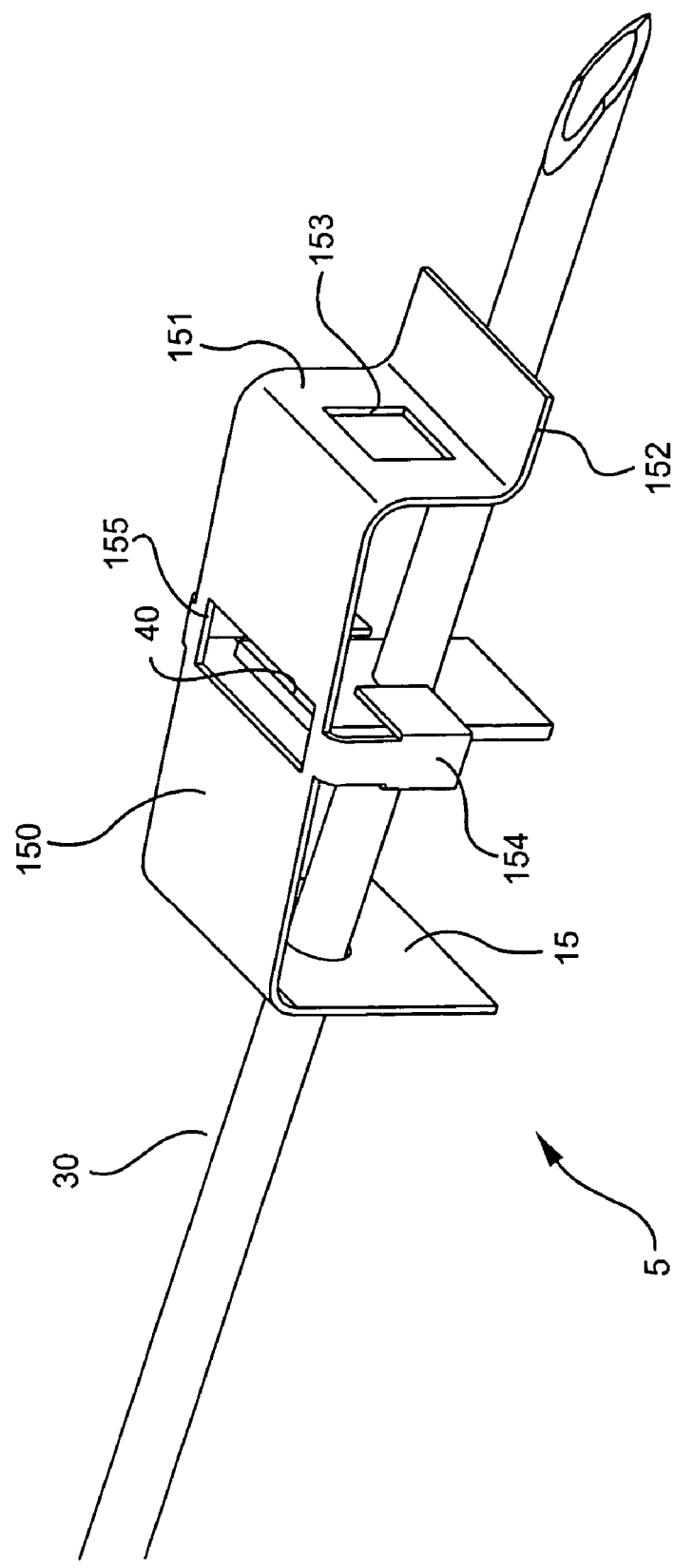
FIG. 18A is a front perspective view of another embodiment of the invention in which the canting plate is actuated by an integral spring member shown in an unactuated condition.
Figure 18B:
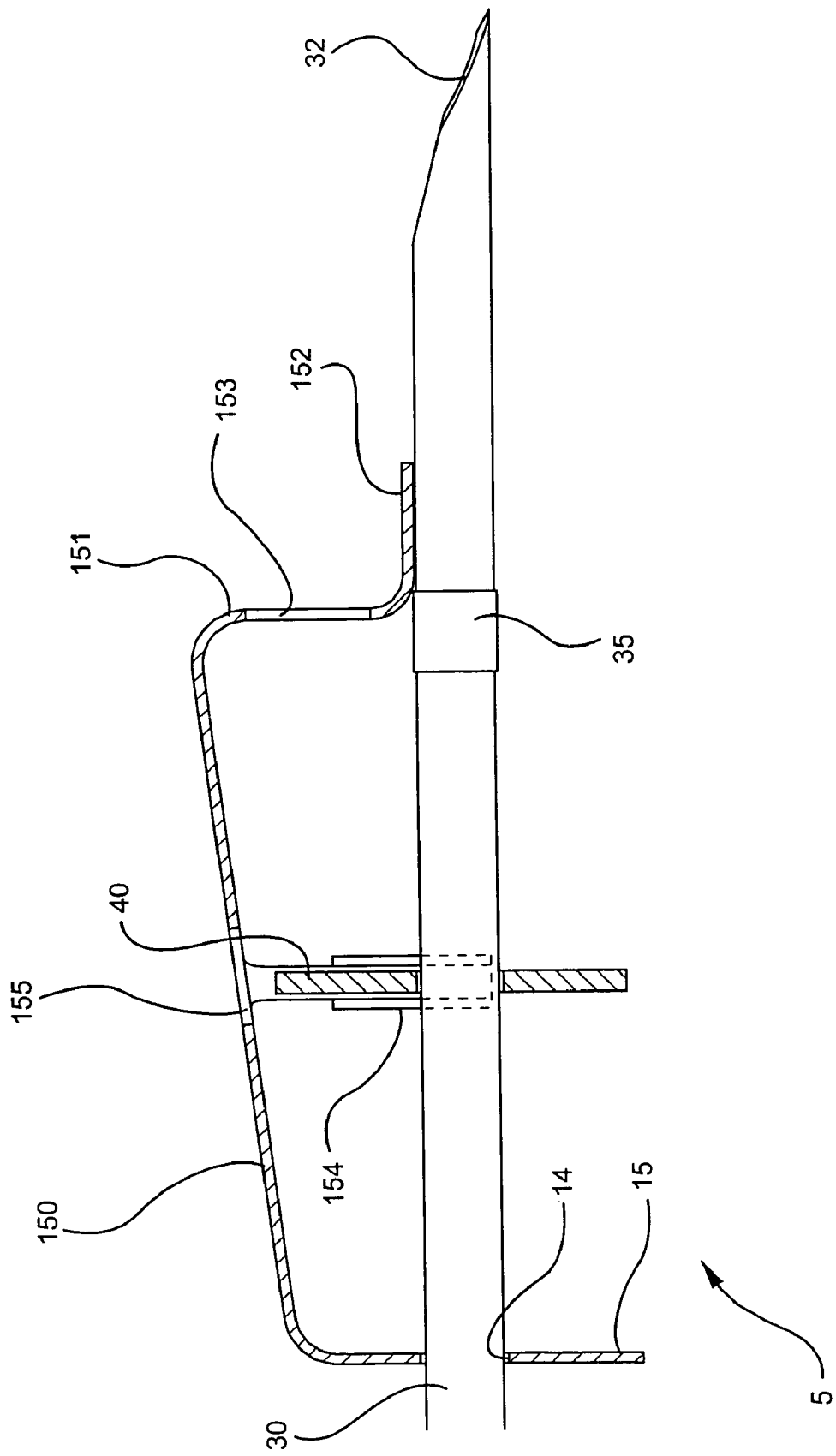
FIG. 18B is a side cross-sectional view of the embodiment shown in FIG. 18A in an unactuated condition.
Figure 18C:
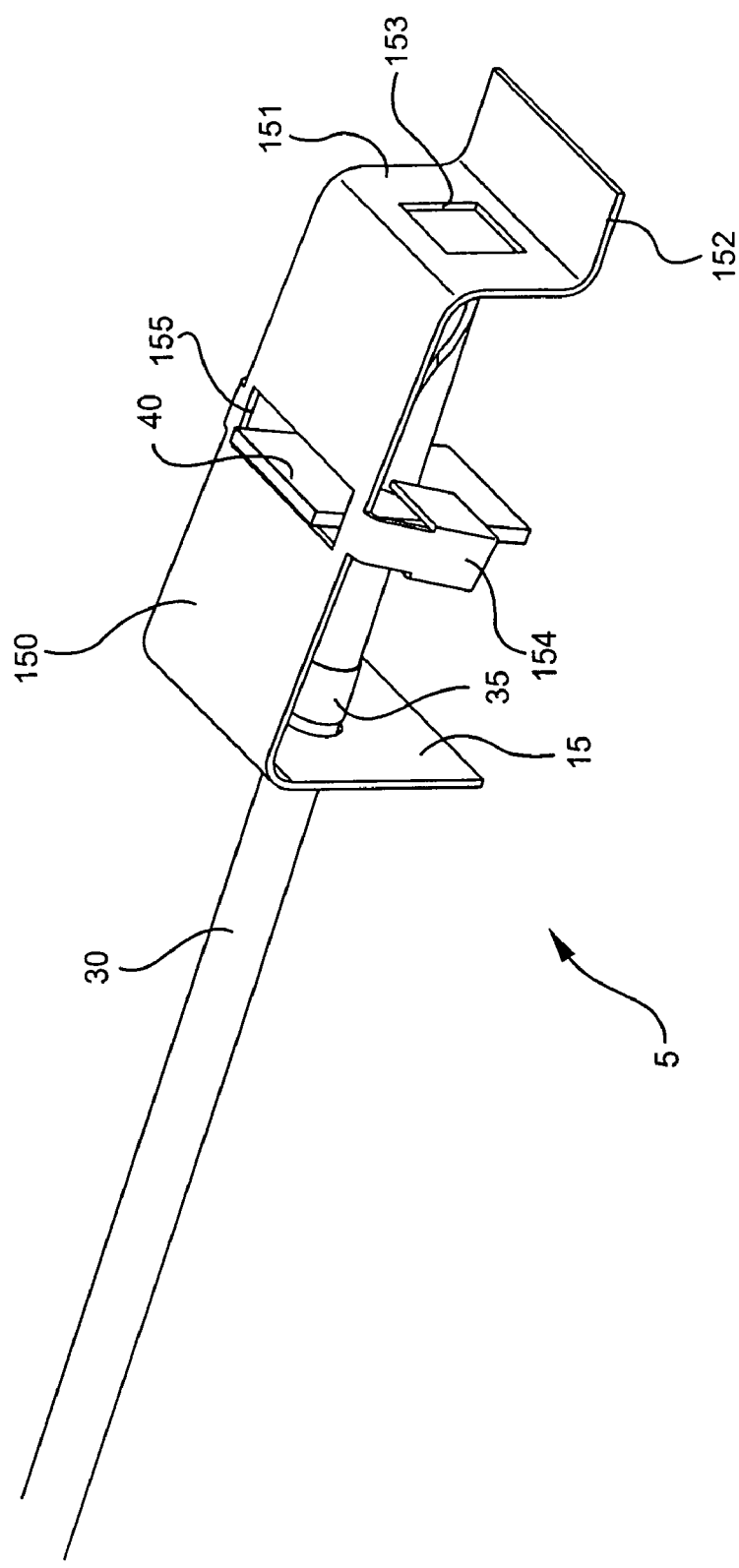
FIG. 18C is a front perspective view of the embodiment shown in FIG. 18A shown in an actuated condition.
Figure 18D:
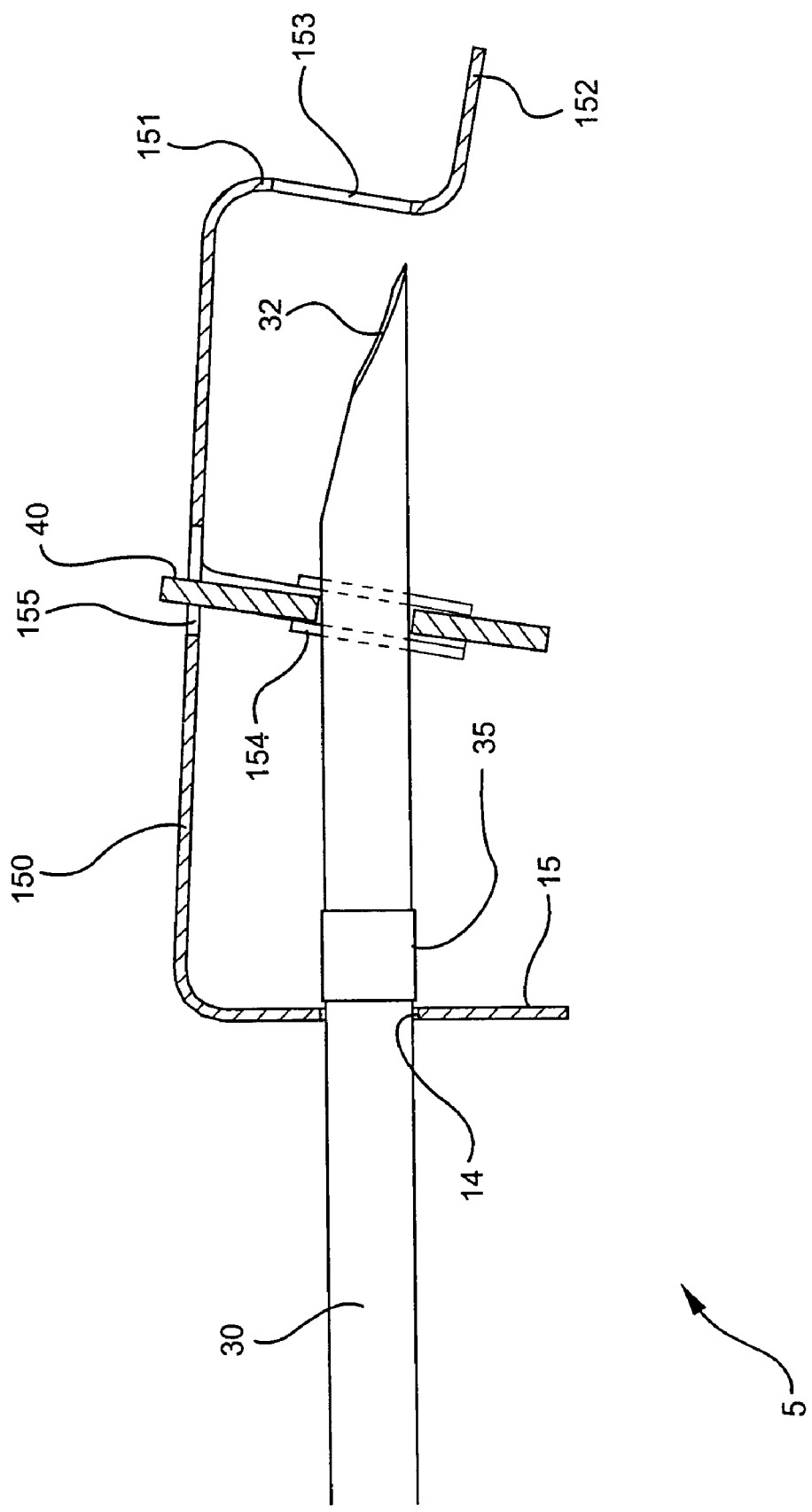
FIG. 18D is a cut-away side view of the embodiment shown in FIG. 18A in an actuated condition.

In the unactuated condition, as seen in FIGS. 18A and 18B, the retention plate 15 and the arm 150 are flexed away from each other (that is, biased open) and maintained in this flexed condition by the presence of the needle 30 in the opening 14 of the retention washer, and the engagement of the needle with the plate 152. After insertion of the catheter 108 into the patient's vein, the needle shield assembly 5 is moved toward the needle tip 32 (or, alternatively, the needle 30 is withdrawn through the needle shield assembly). As the needle moves proximally with respect to the needle shield assembly 5, the tip 32 of the needle passes beyond the slide plate 152 such that the arm 150 and retention plate 15 can return to their unbiased condition, rotating toward each other, as seen in FIGS. 18C and 18D. In this unbiased or actuated condition, the u-shaped members 154 are displaced with respect to the retention washer 15 (specifically, the u-shaped members are rotated with respect to the retention plate). Compare FIG. 18B with FIG. 18D. As such, the canting plate 40 is also displaced with respect to the retention washer (and thus the needle). Effectively, the canting plate is tilted with respect to the needle and thereby engages the exterior of the needle. In the actuated condition, the top of the canting plate protrudes through the aperture 155 in the arm 150. It will be appreciated that the arm 150 could be designed such that such an aperture 155 would not be required but this would result in a larger needle shield assembly 5.

Integrated Plate and Engagement Hooks

Figure 4A:
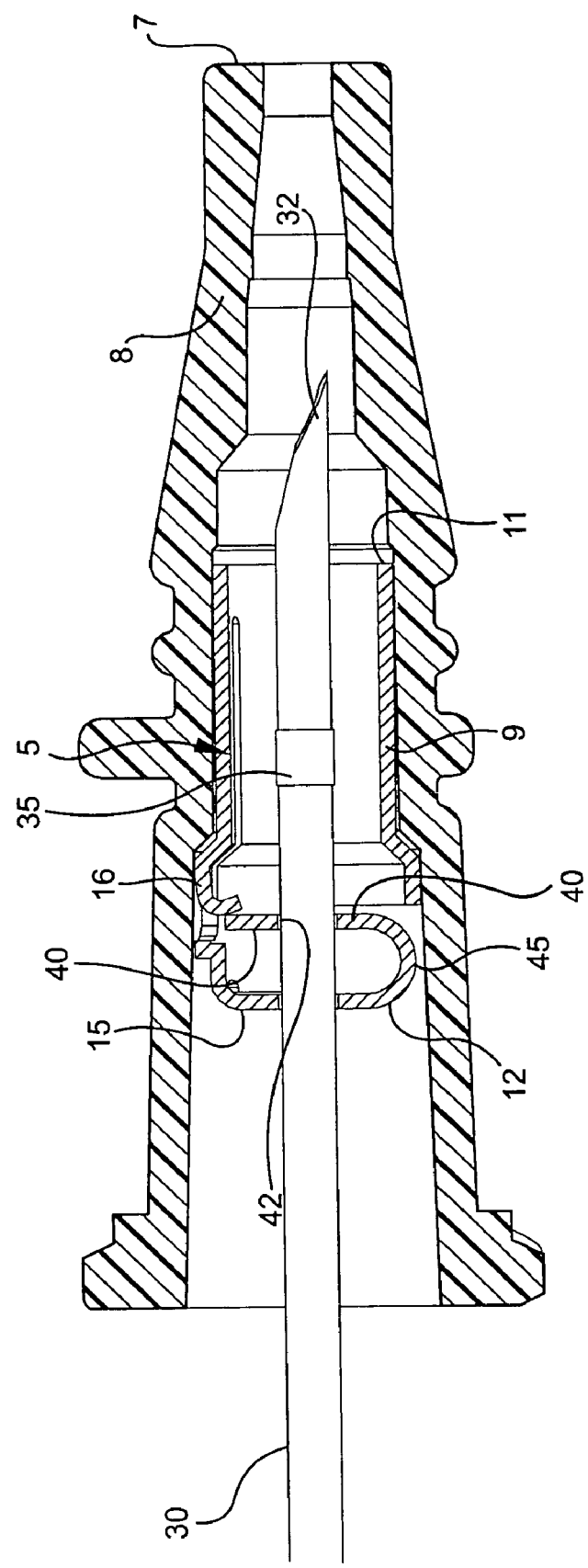
FIG. 4A is a cross-sectional view of another embodiment of the invention, with the canting plate and spring integral to the shield, shown in an unactuated condition, where the needle has been partly withdrawn through the catheter but the sharp distal tip of the introducer needle has yet to be withdrawn into the needle shield.
Figure 4B:
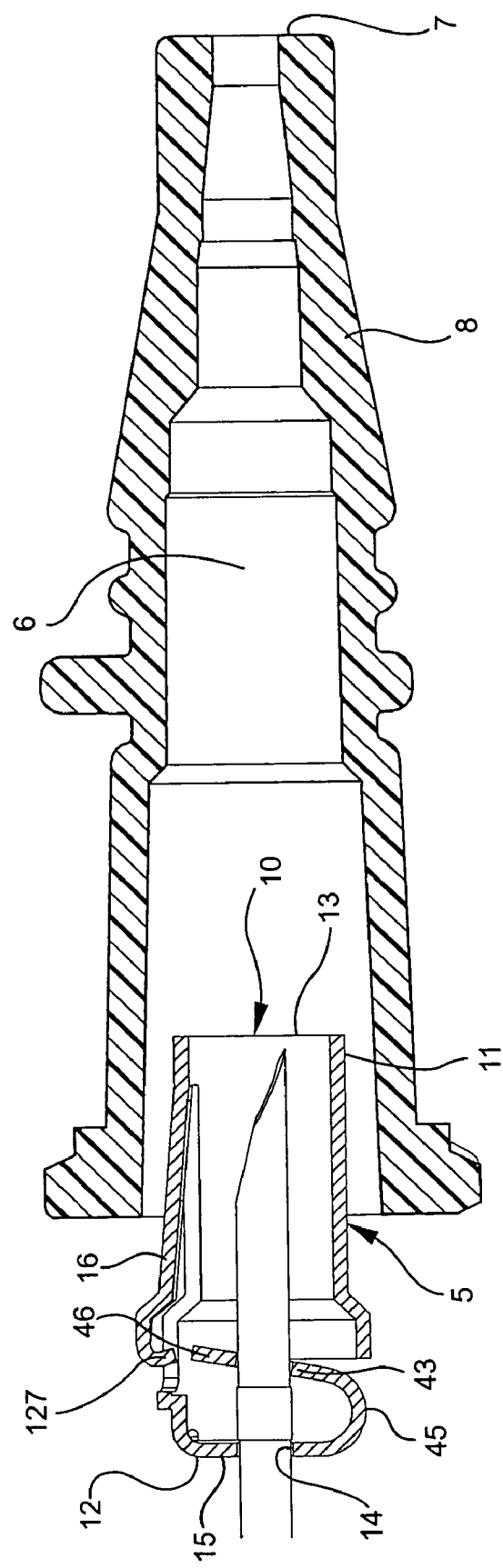
FIG. 4B is a cross-sectional view of the embodiment in FIG. 4A in an actuated condition where the sharp distal tip of the introducer needle has been withdrawn proximally into the needle shield assembly.
Figure 5A:
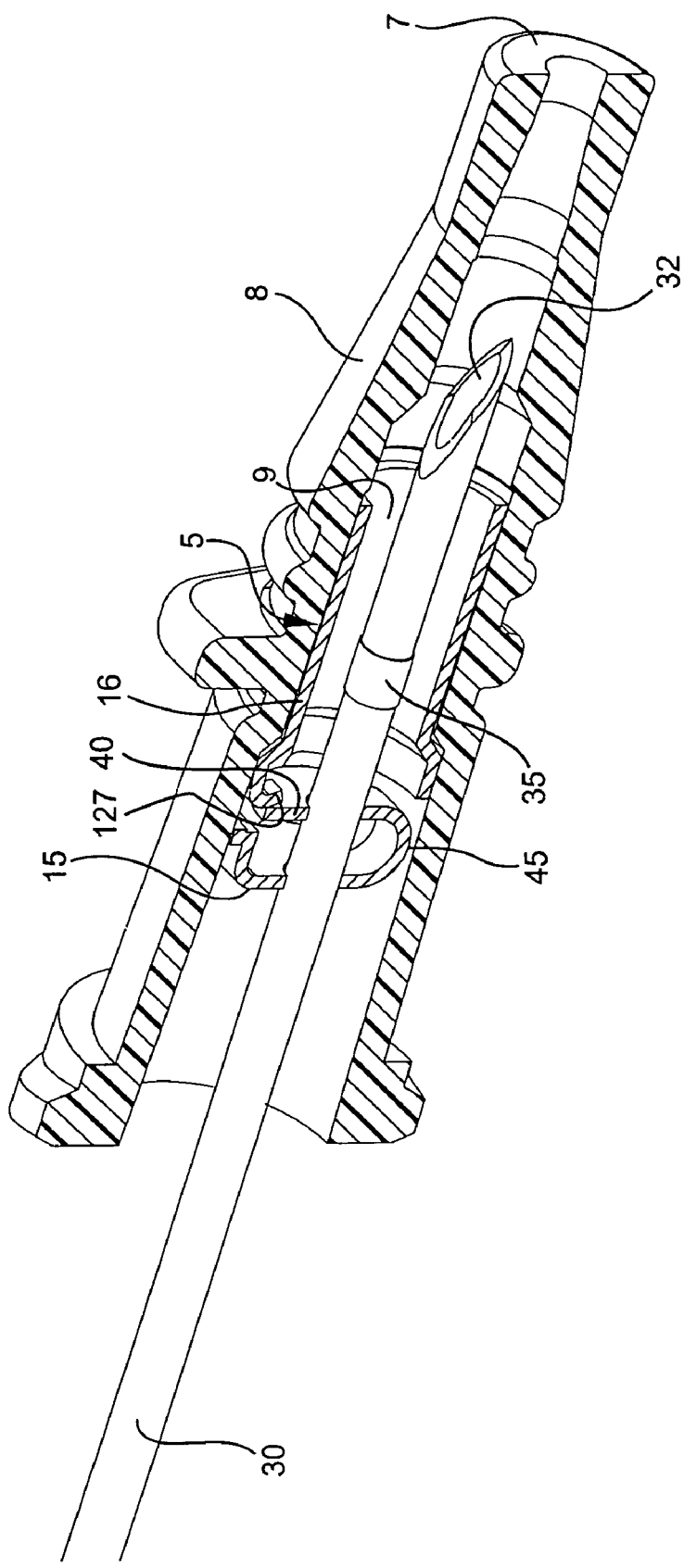
FIG. 5A is a cross-sectional perspective view of the needle shield of FIG. 4A.
Figure 5B:
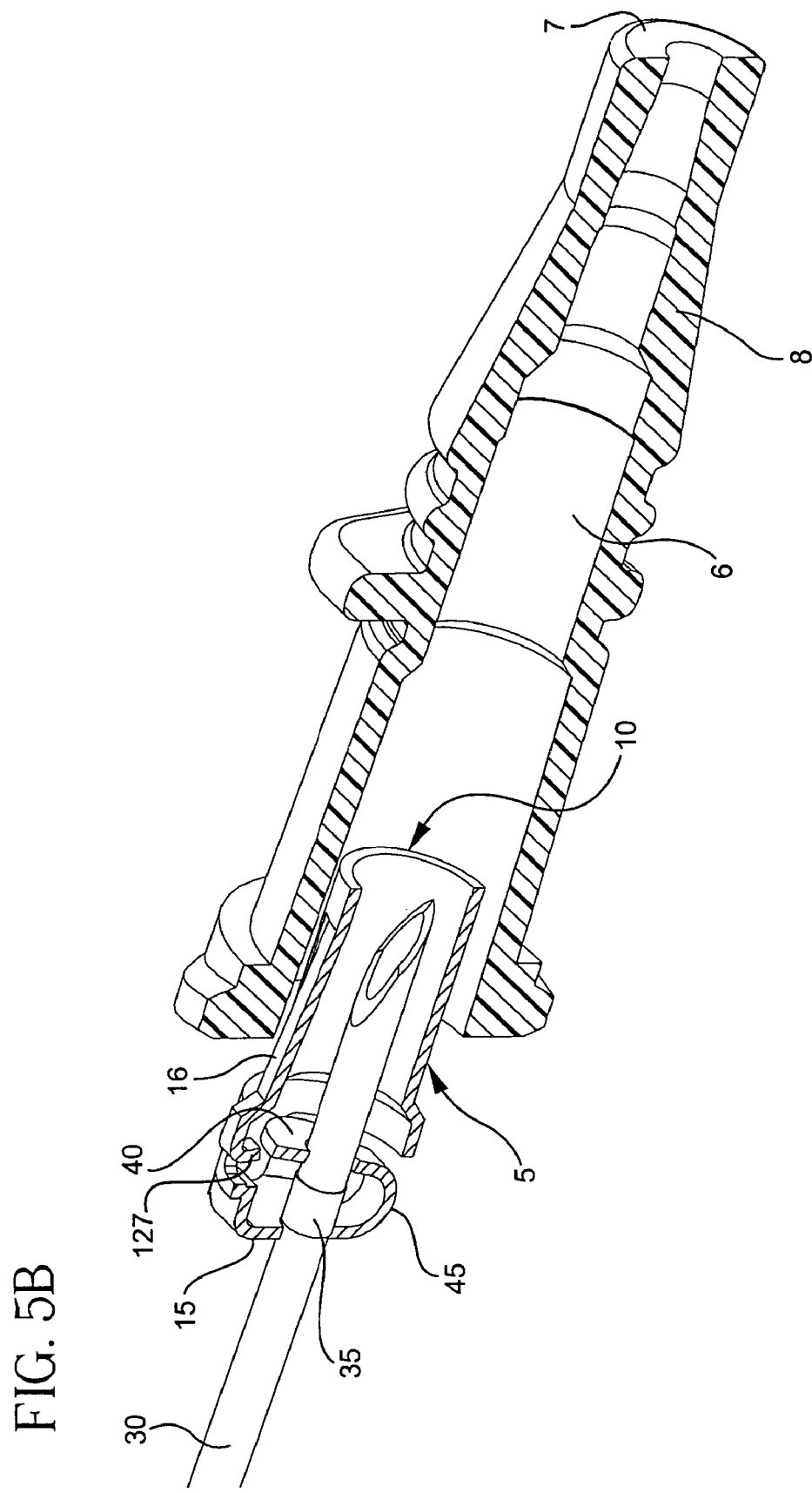
FIG. 5B is a cross-sectional perspective view of the needle shield assembly depicted in FIG. 4B.
Figure 6A:
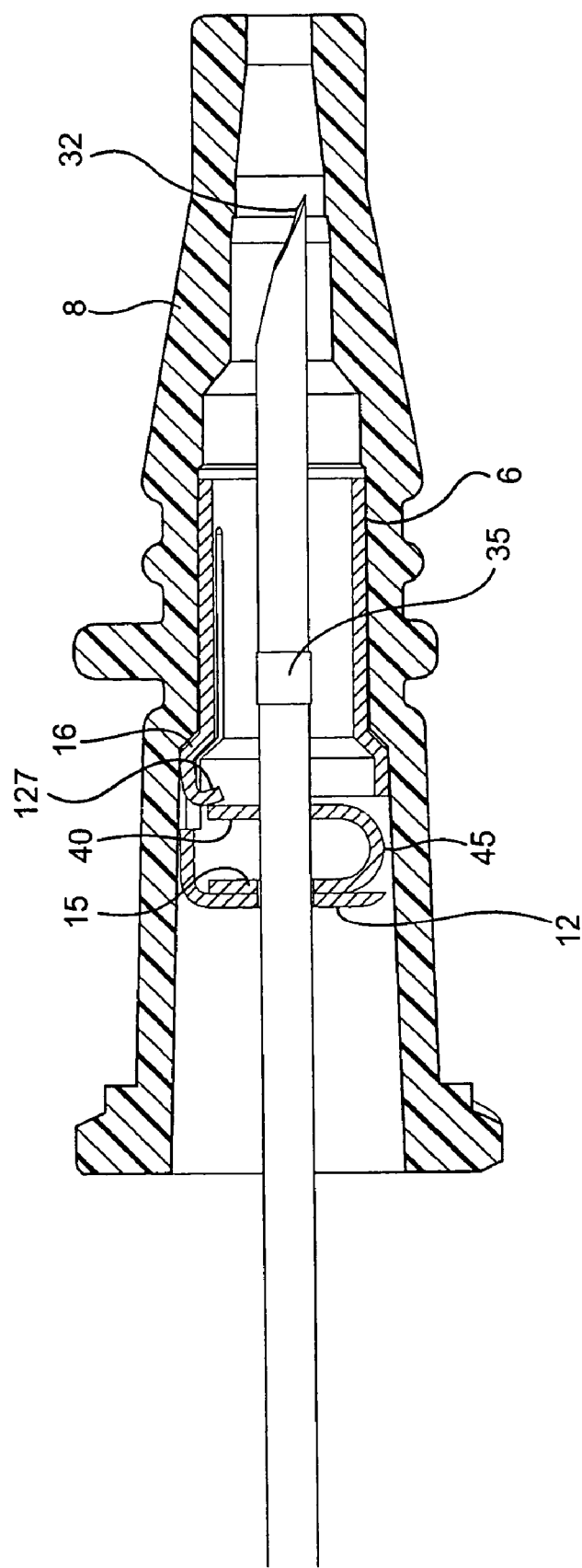
FIG. 6A is a cross-sectional view of another embodiment of the invention, with the canting plate, retention washer and spring integrally formed, shown in an unactuated condition, where the needle has been partly withdrawn through the catheter but the sharp distal tip of the introducer needle has yet to be withdrawn into the needle shield.
Figure 6B:
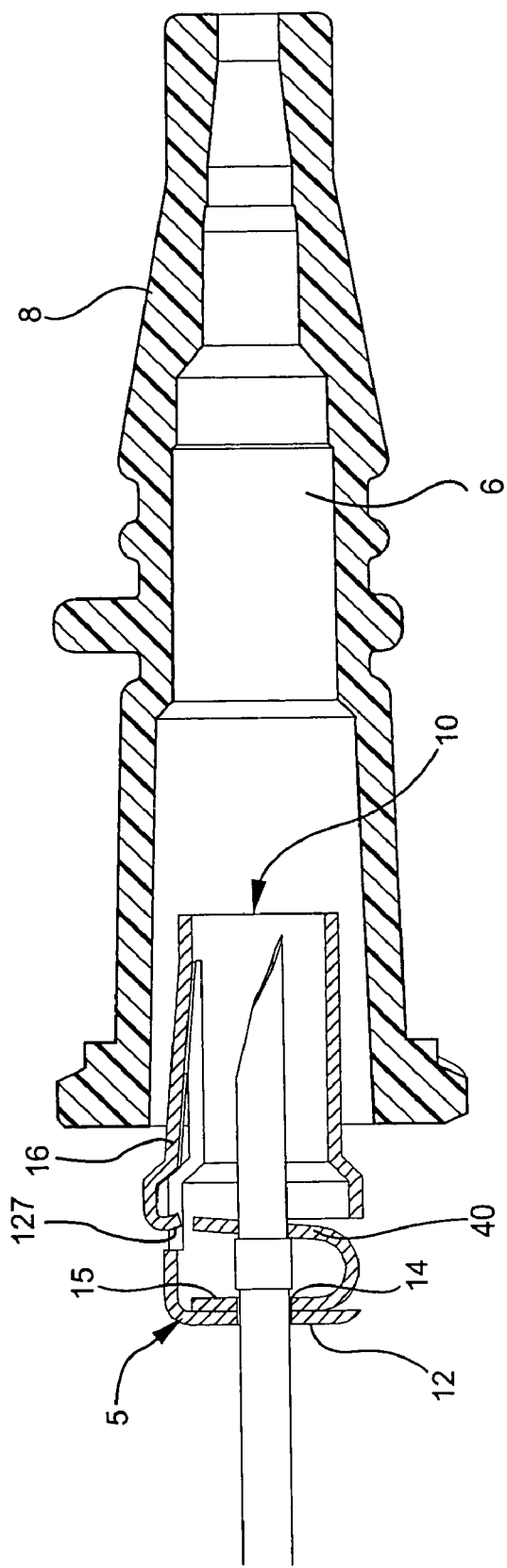
FIG. 6B is a cross-sectional view of the embodiment in FIG. 6A in an actuated condition where the sharp distal tip of the introducer needle has been withdrawn proximally into the needle shield assembly.
Figure 7A:
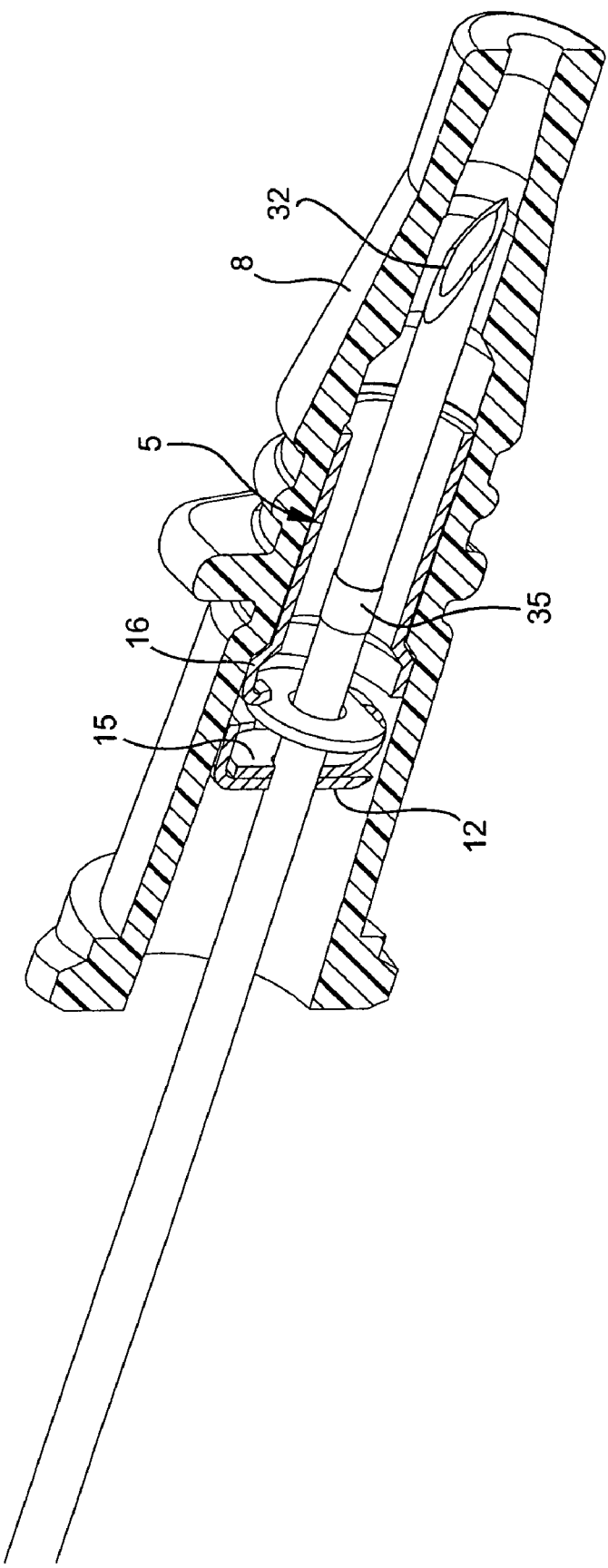
FIG. 7A is a cross-sectional perspective view of the needle shield of FIG. 6A.
Figure 7B:
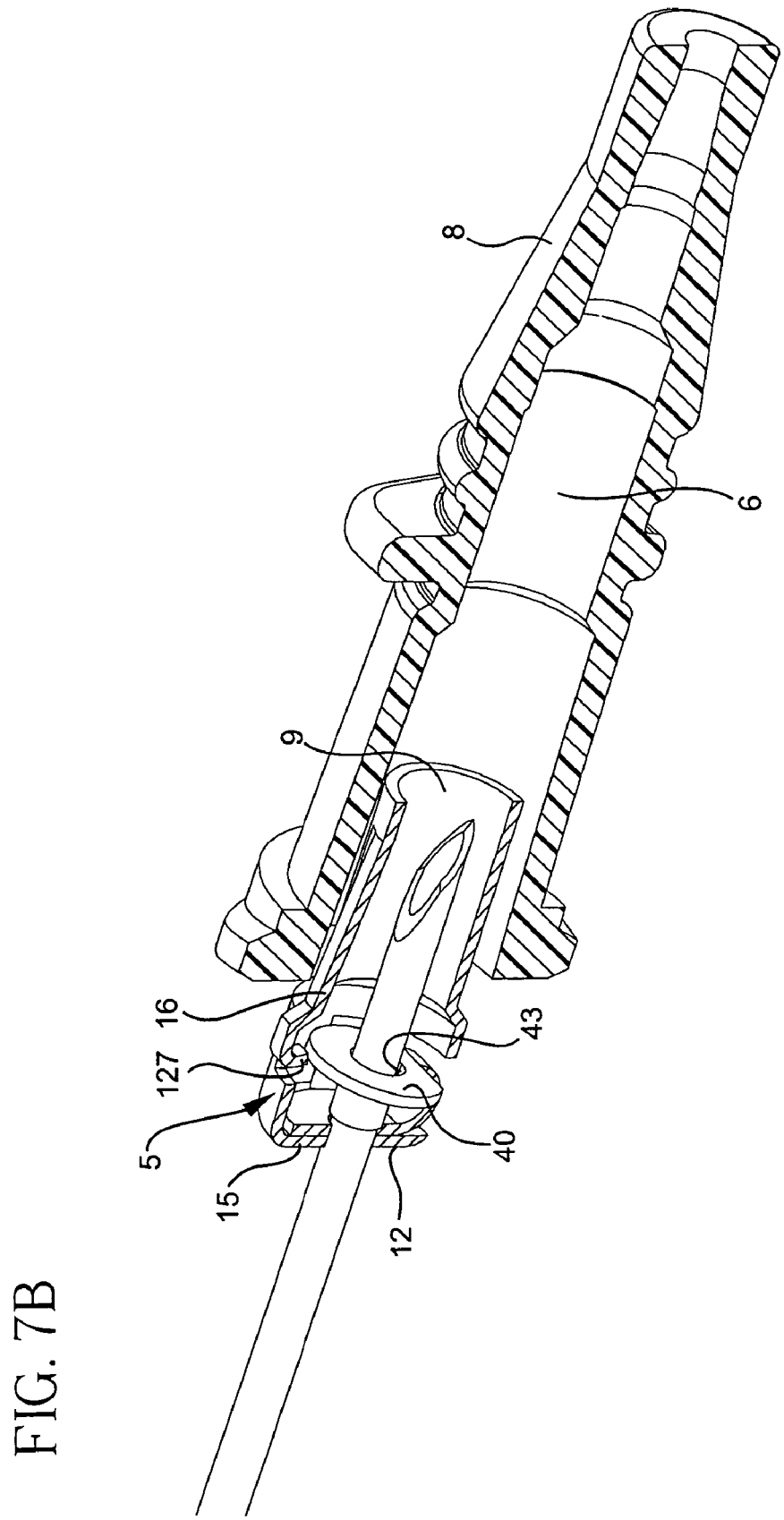
FIG. 7B is a perspective view of the needle shield assembly depicted in FIG. 6B in partial cross section.
Figure 19A:
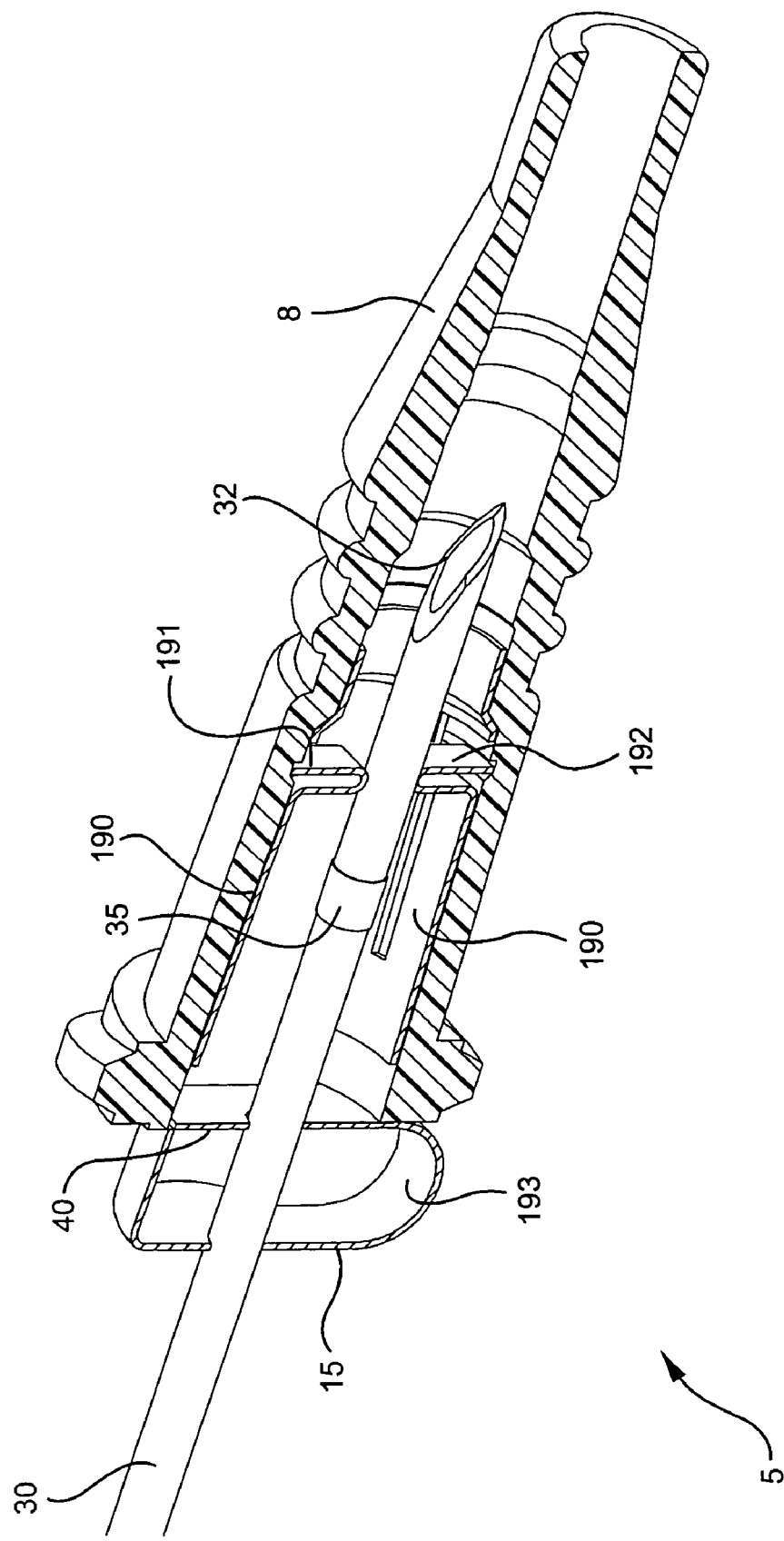
FIG. 19A is a front perspective view of another embodiment of the invention in which the needle shield assembly is engaged with a catheter hub until the needle tip is withdrawn into the needle shield assembly, shown in an unactuated condition.
Figure 19B:
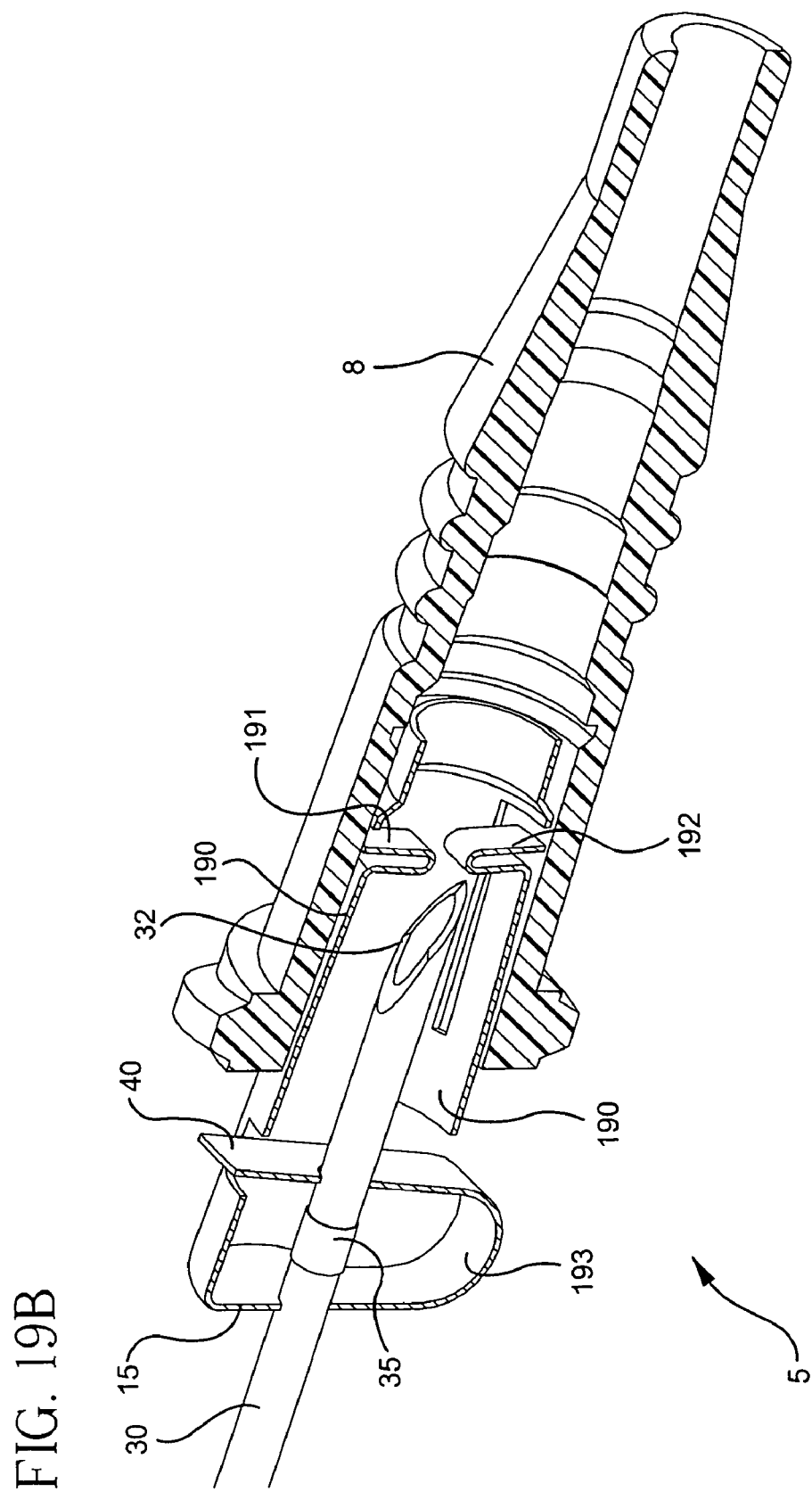
FIG. 19B is a front perspective view of the embodiment shown in FIG. 19A in an actuated condition.

Referring now to FIGS. 19A and 19B, an implementation of the invention is depicted that includes a mechanism for engaging a catheter adapter 8 until the needle tip 32 has been withdrawn into the needle shield assembly 5, somewhat similar to the implementation depicted in FIGS. 4A-B. The needle shield assembly includes two engagement arms 190 (preferably in the form of leaf springs integrally formed with the shield body 10) that are biased radially outwardly from the body of the needle shield assembly. Hooks 191 are attached to the distal end of the engagement arms 190. In the unactuated condition, the needle 30 is positioned between the hooks, thereby urging the hooks and the engagement arms radially outward. The hooks therefore are disposed within an annular groove 192 in the catheter adapter 8. Consequently, the catheter adapter may not be displaced off of the needle shield assembly. As the needle is withdrawn from between the hooks, the engagement arms flex radially inward to their unstressed condition as seen in FIG. 19B. As such, the hooks 191 disengage the annular groove 192. Consequently, the needle shield assembly 5 may now be removed from the catheter adapter 8.

The needle shield assembly 5 also includes a retention washer 15 integrally formed with a canting plate 40 and connected by a flexural hinge member 193. The hinge member is a spring which urges the canting plate 40 into a canted condition. When assembled and before actuation (see FIG. 19A), the canting plate is maintained in alignment with the needle by the cooperation of the force exerted by the flexural hinge 193 and interference with the proximal end of the catheter adapter 8. Consequently, the needle 30 is free to pass through the canting plate without interference. As the needle shield assembly is disengaged from the catheter adapter and moves proximally out of the catheter adapter, the canting plate is free to succumb to the bias of the flexural hinge 193 and thus engage the exterior of the needle 30 (see FIG. 19B).

Integral Washer, Hinge and Canting Plate with Actuation Arm

Figure 20A:
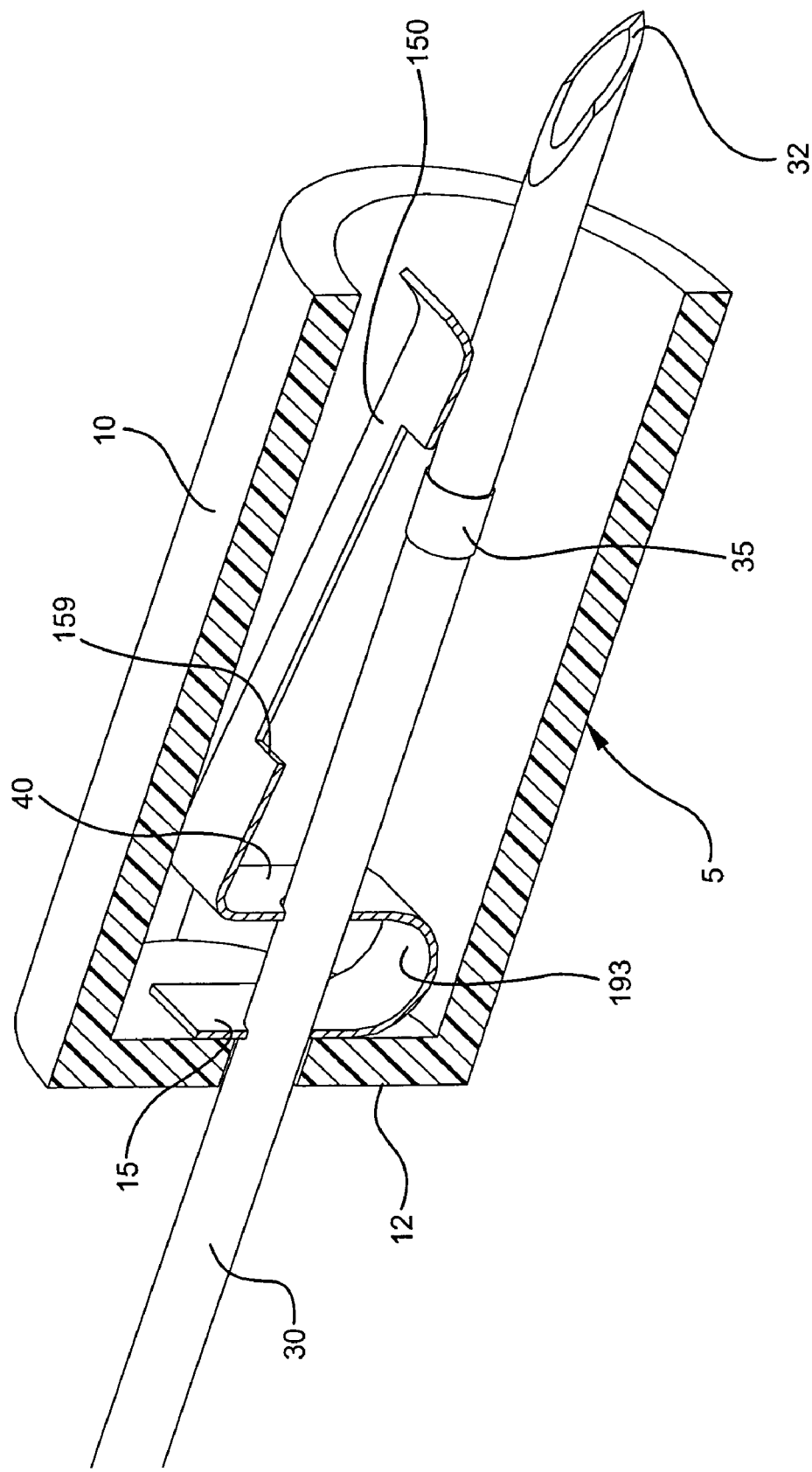
FIG. 20A is a front perspective view in partial cut-away of another embodiment of the invention in which the canting plate is integrally formed with a retention washer and a tip trigger, shown in an unactuated condition.
Figure 20B:
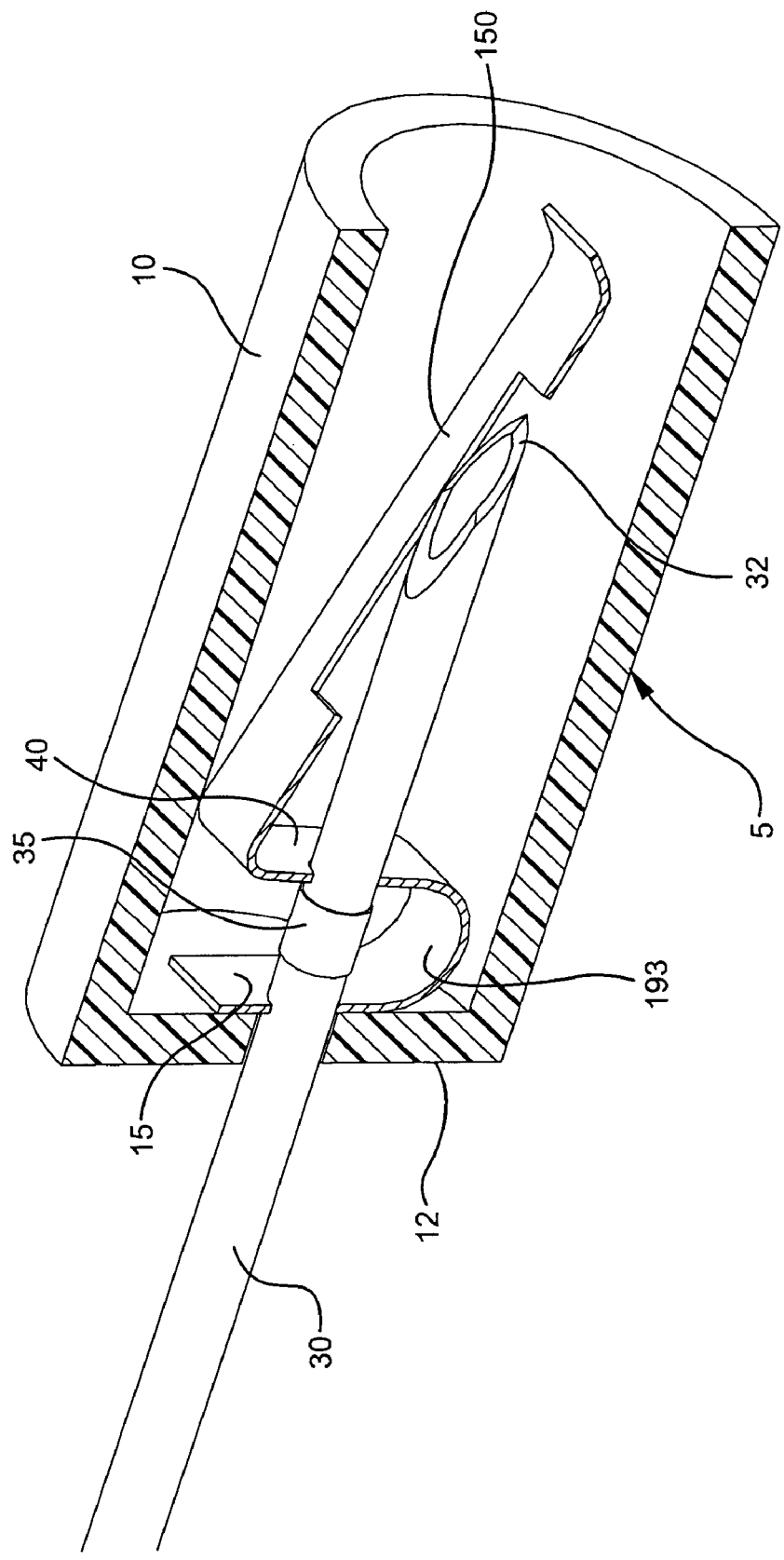
FIG. 20B is a front perspective view of the embodiment shown in FIG. 20A in an actuated condition.

Referring now to FIGS. 20A and 20B, an implementation of the invention is depicted including a retention washer 15 integrally formed with a flexural hinge 193 which in turn integrally formed with a canting plate 40 which is in turn integrally formed with an actuation arm 150. The retention washer is attached to the proximal end 12 of a shield body 10.

In the unactuated condition, the canting plate is maintained in alignment with the needle 30 by the cooperation of the force exerted by the flexural hinge 193 and the restraint exerted by actuation arm 150. Specifically, the flexural hinge 193 acts as a spring urging the canting plate into a canted or engaging condition. This movement of the canting plate is prevented by the actuation arm which itself is engaged to the needle. See FIG. 20A. As the needle tip 32 is withdrawn, the actuation arm 150 comes out of engagement with the needle tip and is therefore free to move within the shield body 10. Consequently, the canting plate 40 succumbs to the bias exerted by the flexural hinge 193. As the canting plate is tilted out of alignment with the needle, it bindingly engages to the exterior of the needle. A cutout 159 may be provided on the actuation arm to permit movement of the actuation arm after passage of the needle tip without interference from the needle.

As disclosed above, certain implementations of the invention employ a feature 35 on the needle 30 to limit motion of the needle shield assembly 5 with respect to the tip 32 of the needle. Other implementations employ a tether 400 to limit motion of the needle tip with respect to the needle shield assembly. It will be appreciated that in the various embodiments, the feature may be replaced with a tether (or the tether replaced with a feature) and still practice the invention. Further, the friction member is referred to, in certain implementations as an elastomeric washer. It will be appreciated that the friction member may be made of elastomers, or other materials having different properties and various shapes and still practice aspects of the invention.

The preceding description is exemplary rather than limiting in nature. Variations and modifications to the disclosed examples may become apparent to those skilled in the art that do not necessarily depart from the purview and spirit of this invention. For example, implementations of the invention may be employed with other needles, such as anesthesia needles or syringes or blood sample collection sets. The scope of legal protection given to this invention can only be determined by studying the following claims.

We claim:

1. An over-the-needle catheter assembly comprising:
   an adapter;
   a needle having a diameter and a distal tip, slidingly disposed within the adapter;
   a needle shield assembly slidably mounted on the needle, wherein the needle shield assembly has an open distal end and an open proximal end through which the needle passes;
   a plurality of canting plates disposed within the needle shield assembly and having an unactivated first position and an activated second position for restricting distal needle movement; and whereby
   an elastomeric member compressed between the canting plates for exerting a continuous biasing force on the canting plates while the canting plates are in the unactivated first position; and wherein
   the canting plates are responsive to proximal movement of the needle, such that when the needle tip is housed within the needle shield assembly, the canting plates are actuated, allowing movement of the canting plates from the unactivated first position to the activated second position,
   wherein the elastomeric member is a washer.

2. The needle shield assembly of claim 1 comprising at least one canting plate retention arm and a retention washer.

3. The needle shield assembly of claim 1 wherein the elastomeric member is a washer having a concave distal end.

4. The needle shield assembly of claim 1 wherein the adapter and the shield are held together by an interlock.

5. The needle shield assembly of claim 4 further comprising a static feature on the needle, wherein said interlock is released prior to the static feature on the needle contacting the shield proximal end.

6. The needle shield assembly of claim 5 wherein the length between the needle tip and the static feature is such that when said static feature contacts the shield proximal end said needle tip is housed within said shield.

7. The needle shield assembly of claim 1 wherein each of the canting plates contains a hole for passage of the needle and said canting plates are located distally of the proximal end of the shield.

8. The needle shield assembly of claim 1 wherein said canting plates are returned to an unactivated position when said needle is no longer urged in a distal direction.

9. An over-the-needle catheter assembly of claim 1, wherein the elastomeric member further comprises a central cavity, wherein the central cavity is sized to frictionally engage the needle.

10. An over-the-needle catheter assembly of claim 1, wherein the plurality of canting plates further comprises,
    a proximal canting plate disposed within the shield assembly and movable between an aligned condition and an off-alignment condition; and
    a distal canting plate disposed within the shield assembly and movable between an aligned condition and an off-alignment condition.

11. An over-the-needle catheter assembly of claim 1, further comprising
    an alignment means for maintaining the plurality of canting plates in an aligned condition;
    wherein the elastomeric member is selectively operable to at least one canting plate such that, as the needle is moved axially with respect to the shield assembly, the needle displaces the elastomeric member which, in turn, displaces at least one of the plurality of canting plates to an off-alignment condition.

12. The over-the-needle catheter assembly of claim 11 wherein the alignment means comprises a spring arm that is biased radial outward from the shield assembly.

13. The over-the-needle catheter assembly of claim 12 wherein the alignment means comprises at least one retention arm.

14. The over-the-needle catheter assembly of claim 1 further comprising a feature on the needle adapted to engage the shield assembly.

15. The over-the-needle catheter assembly of claim 1 further comprising a tether engaged to the shield assembly and to the needle, restricting the relative movement of the shield assembly and the needle.

* * * * *